:::

United States Patent [19]

Kathawala

[11] Patent Number: 5,354,772

[45] Date of Patent: Oct. 11, 1994

[54] INDOLE ANALOGS OF MEVALONOLACTONE AND DERIVATIVES THEREOF

[75] Inventor: Faizulla G. Kathawala, Mountain Lakes, N.J.

[73] Assignee: Sandoz Pharm. Corp., E. Hanover, N.J.

[21] Appl. No.: 157,595

[22] Filed: Nov. 24, 1993

Related U.S. Application Data

[60] Continuation of Ser. No. 722,288, Apr. 11, 1985, abandoned, which is a continuation-in-part of Ser. No. 707,854, Mar. 4, 1985, Pat. No. 4,739,073, which is a division of Ser. No. 548,850, Nov. 4, 1983, abandoned, which is a continuation-in-part of Ser. No. 443,668, Nov. 22, 1982, abandoned.

[51] Int. Cl.$^5$ .............................................. A61K 31/405
[52] U.S. Cl. ................................. 514/414; 514/415; 548/465; 548/467; 548/468; 548/494; 548/502; 548/414; 548/406
[58] Field of Search .............. 548/465, 467, 468, 494; 514/414, 415, 412

[56] References Cited

U.S. PATENT DOCUMENTS

| | | | |
|---|---|---|---|
| 3,983,140 | 9/1976 | Endo et al. . | |
| 4,198,425 | 4/1980 | Mitsui et al. . | |
| 4,248,889 | 2/1981 | Oka et al. | 560/56 |
| 4,255,444 | 3/1981 | Oka et al. . | |
| 4,308,378 | 12/1981 | Stokker . | |
| 4,351,844 | 9/1982 | Patchett et al. | 560/119 |
| 4,361,515 | 11/1982 | Terahara et al. | 549/292 |
| 4,375,475 | 3/1983 | Willard et al. | 549/292 |
| 4,376,683 | 3/1983 | Lam | 549/292 |
| 4,440,927 | 4/1984 | Prugh | 549/292 |
| 4,474,971 | 10/1984 | Wareing | 549/214 |
| 4,571,428 | 2/1986 | Kapa | 556/437 |
| 4,647,576 | 3/1987 | Hoefle | 548/465 |
| 5,032,590 | 7/1991 | Hübsch | 548/465 |
| 5,118,853 | 6/1992 | Lee et al. | 548/494 |

FOREIGN PATENT DOCUMENTS

| | | |
|---|---|---|
| 895445 | 4/1983 | Belgium . |
| 79042 | 10/1984 | Greece . |
| 84-02131 | 6/1984 | PCT Int'l Appl. . |
| 527428 | 1/1985 | Spain . |

OTHER PUBLICATIONS

Yang, Tetrahedron Letters 23, 4305–4308 (1982).
Hulcher, Arch. Biochem. Biophys 146, 422–427 (1971).
Sato et al., chem. Pharm. Bull. 28, 1509–1525 (1980).
Singer et al., Proc. Soc. Exp. Biol. Med. 102, 370–373 (1959).

*Primary Examiner*—Donald G. Daus
*Attorney, Agent, or Firm*—Robert S. Honor; Melvyn M. Kassenoff

[57] ABSTRACT

Compounds of the formula

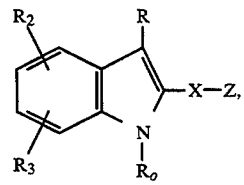

wherein one of R and $R_o$ is

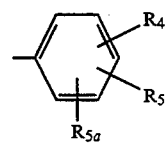

and the other is primary or secondary $C_{1-6}$alkyl not containing an asymmetric carbon atom, $C_{3-6}$cycloalkyl or phenyl-$(CH_2)_m$—, wherein $R_4$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy, $R_5$ is hydrogen, $C_{1-3}$alkyl, $C_{1-3}$alkoxy, trifluoromethyl, fluoro, chloro, phenoxy or benzyloxy, $R_{5a}$ is hydrogen, $C_{1-2}$alkyl, $C_{1-2}$alkoxy, fluoro or chloro, and (Abstract continued on next page.)

Abstract continued m is 1, 2 or 3, with the provisos that both $R_5$ and $R_{5a}$ must be hydrogen when $R_4$ is hydrogen, $R_{5a}$ must be hydrogen when $R_5$ is hydrogen, not more than one of $R_4$ and $R_5$ is trifluoromethyl, not more than one of $R_4$ and $R_5$ is phenoxy, and not more than one of $R_4$ and $R_5$ is benzyloxy, $R_2$ is hydrogen, $C_{1-3}$alkyl, n-butyl, i-butyl, t-butyl, $C_{3-6}$cycloalkyl, $C_{1-3}$alkoxy, n-butoxy, i-butoxy, trifluoromethyl, fluoro, chloro, phenoxy or benzyloxy, $R_3$ is hydrogen, $C_{1-3}$alkyl, $C_{1-3}$alkoxy, trifluoromethyl, fluoro, chloro, phenoxy or benzyloxy, with the provisos that $R_3$ must be hydrogen when $R_2$ is hydrogen, not more than one of $R_2$ and $R_3$ is trifluoromethyl, not more than one of $R_2$ and $R_3$ is phenoxy, and not more than one of $R_2$ and $R_3$ is benzyloxy, X is —(CH$_2$)$_n$— or —CH=CH—, wherein n is 0, 1, 2 or 3, and Z is

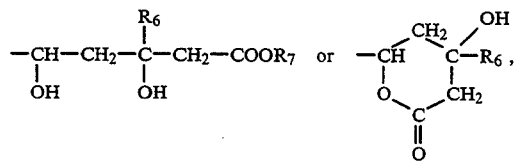

wherein
$R_6$ is hydrogen or $C_{1-3}$alkyl, and
$R_7$ is hydrogen, $R_{7b}$ or M, wherein
$R_{7b}$ is a physiologically acceptable and hydrolyzable ester group, and
M is a pharmaceutically acceptable cation, the use thereof for inhibiting cholesterol biosynthesis and lowering the blood cholesterol level, and therefore, in the treatment of hyperliopoproteinemia and atherosclerosis, pharmaceutical compositions comprising such compounds and processes for and intermediates in the synthesis of such compounds.

30 Claims, No Drawings

INDOLE ANALOGS OF MEVALONOLACTONE AND DERIVATIVES THEREOF

This is a continuation of application Ser. No. 06/722,288, filed Apr. 11, 1985 and now abandoned, which is a continuation-in-part of application Ser. No. 06/707,854, filed Mar. 4, 1985 and now U.S. Pat. No. 4,739,073, which in turn is a division of application Ser. No. 06/548,850, filed Nov. 4, 1983 and now abandoned, which in turn is a continuation-in-part of application Ser. No. 06/443,668, filed Nov. 22, 1982 and now abandoned.

This invention relates to compounds of the formula

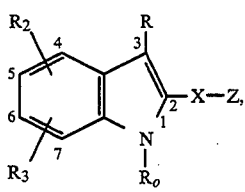

(I)

wherein one of R and $R_o$ is

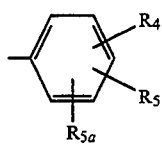

and the other is primary or secondary $C_{1-6}$alkyl not containing an asymmetric carbon atom, $C_{3-6}$cycloalkyl or phenyl-$(CH_2)_m$—,
wherein
$R_4$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy,
$R_5$ is hydrogen, $C_{1-3}$alkyl, $C_{1-3}$alkoxy, trifluoromethyl, fluoro, chloro, phenoxy or benzyloxy,
$R_{5a}$ is hydrogen, $C_{1-2}$alkyl, $C_{1-2}$alkoxy, fluoro or chloro, and
m is 1, 2 or 3, with the provisos that both $R_5$ and $R_{5a}$ must be hydrogen when $R_4$ is hydrogen, $R_{5a}$ must be hydrogen when $R_5$ is hydrogen, not more than one of $R_4$ and $R_5$ is trifluoromethyl, not more than one of $R_4$ and $R_5$ is phenoxy, and not more than one of $R_4$ and $R_5$ is benzyloxy,
$R_2$ is hydrogen, $C_{1-3}$alkyl, n-butyl, i-butyl, t-butyl, $C_{3-6}$cycloalkyl, $C_{1-3}$alkoxy, n-butoxy, i-butoxy, trifluoromethyl, fluoro, chloro, phenoxy or benzyloxy,
$R_3$ is hydrogen, $C_{1-3}$alkyl, $C_{1-3}$alkoxy, trifluoromethyl, fluoro, chloro, phenoxy or benzyloxy, with the provisos that $R_3$ must be hydrogen when $R_2$ is hydrogen, not more than one of $R_2$ and $R_3$ is trifluoromethyl, not more than one of $R_2$ and $R_3$ is phenoxy, and not more than one of $R_2$ and $R_3$ is benzyloxy,
X is —$(CH_2)_n$— or —CH=CH—, wherein n is 0, 1, 2 or 3, and
Z is

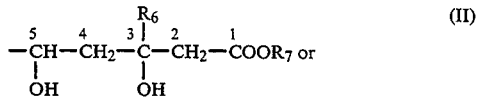

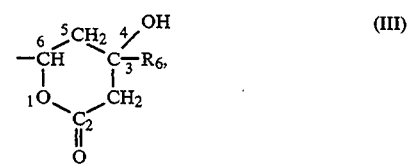

wherein
$R_6$ is hydrogen or $C_{1-3}$alkyl, and
$R_7$ is hydrogen, $R_{7b}$ or M,
wherein
$R_{7b}$ is a physiologically acceptable and hydrolyzable ester group, and
M is a pharmaceutically acceptable cation, processes for and intermediates in the synthesis thereof, pharmaceutical compositions comprising a compound of Formula I and the use of the compounds of Formula I for inhibiting cholesterol biosynthesis and lowering the blood cholesterol level and, therefore, in the treatment of hyperlipoproteinemia and atherosclerosis.

By the term "physiologically acceptable and hydrolyzable ester group" is meant a group which, together with the —COO— radical to which it is attached, forms an ester group which is physiologically acceptable and hydrolyzable under physiological conditions to yield a compound of Formula I wherein $R_7$ is hydrogen and an alcohol which itself is physiologically acceptable, i.e., non-toxic at the desired dosage level, and which, preferably, is free of centers of asymmetry. Examples of such groups are $C_{1-3}$alkyl, n-butyl, i-butyl, t-butyl and benzyl, collectively referred to as $R_{7a}$.

The compounds of Formula I may be divided into two groups, the compounds of Formula IA and those of Formula IB:

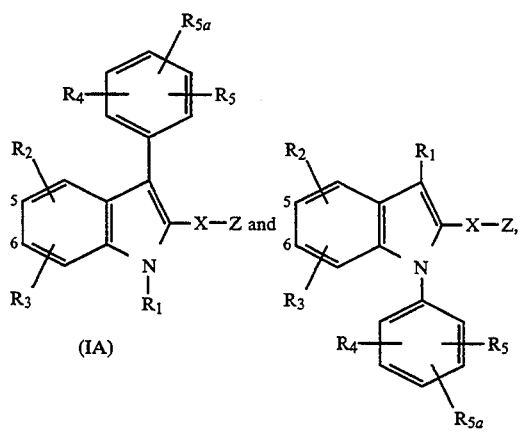

(IA)  (IB)

wherein
$R_1$ is primary or secondary $C_{1-6}$alkyl not containing an asymmetric carbon atom (e.g., methyl, ethyl, n-propyl, i-propyl, n-butyl, i-butyl, 1-ethylpropyl, neopentyl and n-hexyl), $C_{3-6}$cycloalkyl or phenyl-$(CH_2)_m$—, and
$R_2$-$R_{5a}$, X, Z and m are as defined above.

The compounds of Formula IA may be divided into two subgroups, the compounds wherein Z is a group of Formula II (Group IAa) and those wherein Z is a group of Formula III (Group IAb). Likewise, the compounds of Formula IB may be divided into two subgroups, the compounds wherein Z is a group of Formula II (Group IBa) and those wherein Z is a group of Formula III (Group IBb).

As is self-evident to those in the art, each compound of Formula I (and every subscope and species thereof) has two centers of asymmetry (the two carbon atoms bearing the hydroxy groups in the group of Formula II and the carbon atom bearing the hydroxy group and the carbon atom having the free valence in the group of Formula III) and, therefore, there are four stereoisomeric forms (enantiomers) of each compound (two racemates or pairs of diastereoisomers), provided that $R_7$ does not contain any center of asymmetry. The four stereoisomers may be designated as the R,R; R,S; S,R and S,S enantiomers, all four stereoisomers being within the scope of this invention. When $R_7$ contains one or more centers of asymmetry, there are eight or more stereoisomers. Since it is preferred that $R_7$ not contain a center of asymmetry and for reasons of simplicity, any additional stereoisomers resulting from the presence of one or more centers of asymmetry in $R_7$ will usually be ignored, it being assumed that $R_7$ is free of centers of asymmetry.

$R_1$ is preferably $R_1'$, where $R_1'$ is primary or secondary $C_{1-6}$alkyl not containing an asymmetric carbon atom, more preferably $R_1''$, where $R_1''$ is primary or secondary $C_{1-5}$alkyl not containing an asymmetric carbon atom, even more preferably $C_{1-3}$alkyl and most preferably methyl, ethyl or i-propyl, especially i-propyl.

$R_2$ is preferably $R_2'$, where $R_2'$ is hydrogen, $C_{1-3}$alkyl, $C_{1-3}$alkoxy, trifluoromethyl, fluoro, chloro, phenoxy or benzyloxy, more preferably $R_2''$, where $R_2''$ is hydrogen, $C_{1-3}$alkyl, methoxy, fluoro, chloro or 4-, 5- or 6-benzyloxy, even more preferably $R_2'''$, where $R_2'''$ is hydrogen, $C_{1-3}$alkyl or 4- or 6-benzyloxy, and most preferably $R_2''''$, where $R_2''''$ is hydrogen or $C_{1-3}$alkyl, especially hydrogen or methyl and most especially hydrogen.

$R_3$ is preferably $R_3'$, where $R_3'$ is hydrogen, $C_{1-3}$alkyl, $C_{1-2}$alkoxy, fluoro or chloro, more preferably $R_3''$, where $R_3''$ is hydrogen or $C_{1-3}$alkyl, and most preferably $R_3'''$, where $R_3'''$ is hydrogen or methyl, especially hydrogen. $R_3$ ($R_3'$, etc.) must be hydrogen when $R_2$ ($R_2'$, etc.) is hydrogen.

Preferably, when $R_2$ ($R_2'$, $R_2''$, etc.) is other than hydrogen and $R_3$ ($R_3'$, $R_3''$, etc.) is hydrogen, $R_2$ ($R_2'$, etc.) is in the 4-, 5- or 6-position.

Preferably, when both $R_2$($R_2'$, $R_2''$, etc.) and $R_3$ ($R^{3'}$, $R_3''$, etc.) are other than hydrogen, at least one of them is in the 5- or 6-position, neither of them is in the 7-position, and not more than one of them is a member of the group consisting of t-butyl, $C_{3-6}$cycloalkyl, trifluoromethyl, phenoxy and benzyloxy; more preferably, they are not ortho to each other when neither of them is a member of the group consisting of methyl, methoxy, fluoro and chloro. Most preferably, one is in the 4-position and the other is in the 6-position.

Except where otherwise indicated: (a) Any $C_{1-3}$alkyl, n-butyl, i-butyl, t-butyl or $C_{3-6}$cycloalkyl group as $R_2$, $R_2'$, $R_3$, $R_3'$, etc. is more preferably in the 4- or 6-position. (b) Any $C_{1-3}$alkoxy, n-butoxy, i-butoxy, fluoro or chloro substituent as $R_2$, $R_2'$, $R_3$, $R_3'$, etc. is more preferably in the 5-position. (c) Any benzyloxy as $R_2$, $R_2'$, $R_3$, $R_3'$, etc. is more preferably in the 4-, 5- or 6-position and most preferably in the 4- or 6-position, especially the 6-position.

$R_4$ is preferably $R_4'$, where $R_4'$ is hydrogen, $C_{1-3}$alkyl, $C_{1-3}$alkoxy, trifluoromethyl, fluoro, chloro, phenoxy or benzyloxy, more preferably $R_4''$, where $R_4''$ is hydrogen, methyl, methoxy, fluoro or chloro, and most preferably $R_4'''$, where $R_4'''$ is hydrogen, methyl or fluoro, especially $R_4''''$, where $R_4''''$ is hydrogen, 3- or 4-methyl or 4-fluoro, and most especially 4-fluoro. $R_4''$ is also preferably $R_{4a}$, where $R_{4a}$ is hydrogen, $C_{1-2}$alkyl, trifluoromethyl or fluoro.

$R_5$ is preferably $R_5'$, where $R_5'$ is hydrogen, $C_{1-2}$alkyl, $C_{1-2}$alkoxy, fluoro or chloro, more preferably $R_5''$, where $R_5''$ is hydrogen, methyl, methoxy, fluoro or chloro, and most preferably $R_5'''$, where $R_5'''$ is hydrogen or methyl, especially hydrogen. $R_5$ ($R_5'$, $R_5''$, etc.) must be hydrogen when $R_4$ ($R_4'$, $R_4''$, etc.) is hydrogen.

$R_{5a}$ is preferably $R_{5a}'$, where $R_{5a}'$ is hydrogen or methyl, and most preferably hydrogen. $R_{5a}$ ($R_{5a}'$, etc.) must be hydrogen when at least one of $R_4$ ($R_4'$, $R_4''$, etc.) and $R_5$ ($R_5'$, $R_5''$, etc.) is hydrogen.

Preferably, when $R_4$ ($R_4'$, $R_4''$, etc.) is other than hydrogen and $R_5$ ($R_5'$, $R_5''$, etc.) and $R_{5a}$ ($R_{5a}'$, etc.) are both hydrogen, $R_4$ ($R_4'$, etc.) is in a meta or para position, more preferably the para position. The most preferred monosubstituted phenyl group is 4-fluorophenyl.

Preferably, when both $R_4$ ($R_4'$, $R_4''$, etc.) and $R_5$ ($R_5'$, $R_5''$, etc.) are other than hydrogen and $R_{5a}$ ($R_{5a}'$, etc.) is hydrogen, at least one of $R_4$ ($R_4'$, etc.) and $R_5$ ($R_5'$, etc.) is in a meta or para position (more preferably both are), and not more than one of them is a member of the group consisting of t-butyl, trifluoromethyl, phenoxy and benzyloxy; more preferably, $R_4$ ($R_4'$, etc.) and $R_5$ ($R_5'$, etc.) are not ortho to each other when neither of them is a member of the group consisting of methyl, methoxy, fluoro and chloro. The most preferred disubstituted phenyl groups are 3,4- and 3,5-dimethylphenyl and 4-fluoro-3-methylphenyl, especially 3,5-dimethylphenyl and 4-fluoro-3-methylphenyl.

Preferably, when each of $R_4$ ($R_4'$, etc.), $R_5$ ($R_5'$, etc.) and $R_{5a}$ ($R_{5a}'$, etc.) is other than hydrogen, at least two of them (more preferably all three) are in meta or para positions, and not more than one of them is a member of the group consisting of t-butyl, trifluoromethyl, phenoxy and benzyloxy; more preferably, no two of them are ortho to each other unless at least one member of the or each pair of substituents that are ortho to each other is a member of the group consisting of methyl, methoxy, fluoro and chloro. The most preferred trisubstituted phenyl group is 3,5-dimethyl-4-fluorophenyl.

$R_6$ is preferably $R_6'$, where $R_6'$ is hydrogen or $C_{1-2}$alkyl, more preferably $R_6''$, where $R_6''$ is hydrogen or methyl, and most preferably hydrogen.

$R_7$ is preferably $R_7'$, where $R_7'$ is hydrogen, $C_{1-3}$alkyl or M, more preferably $R_7''$, where $R_7''$ is hydrogen, $C_{1-2}$alkyl or M, and most preferably M, especially sodium. M is preferably M' and more preferably sodium.

Representative significances of X are

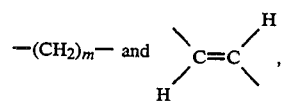

referred to collectively as X'. X' is preferably X'', where X'' is

—CH$_2$CH$_2$— or 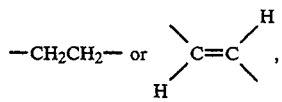, and most preferably

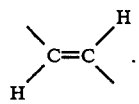.

X is preferably X$_a$, where X$_a$ is —CH$_2$CH$_2$—, —CH$_2$CH$_2$CH$_2$— or —CH=CH—, more preferably X$_a'$, where X$_a'$ is —CH$_2$CH$_2$— or —CH=CH—, even more preferably X" and most preferably

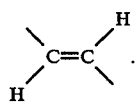.

Z is preferably a group of Formula II wherein R$_6$ is R$_6'$ and R$_7$ is R$_7'$ or a group of Formula III wherein R$_6$ is R$_6'$, more preferably a group of Formula II wherein R$_6$ is R$_6''$ and R$_7$ is R$_7''$ or a group of Formula III wherein R$_6$ is R$_6''$ and most preferably a group of Formula II wherein R$_6$ is hydrogen and R$_7$ is R$_7''$ or a group of Formula III wherein R$_6$ is hydrogen, especially a group of Formula II wherein R$_6$ is hydrogen and R$_7$ is M, especially M' and most especially sodium, or a group of Formula III wherein R$_6$ is hydrogen.

n is preferably m, where m is 1, 2 or 3, preferably 2 or 3 and most preferably 2.

M is usually free from centers of asymmetry and is preferably M', i.e., sodium, potassium or ammonium, and most preferably sodium. For simplicity, each of the formulae in which M appears has been written as if M were monovalent and, preferably, it is. However, it may also be divalent or trivalent and, when it is, it balances the charge of two or three carboxy groups, respectively. Thus, Formula I and every other formula containing an M embraces compounds wherein M is divalent or trivalent, i.e., which contains two or three carboxylate-containing anions per cation M.

Insofar as the compounds of Groups IAa and IBa are concerned, the erythro isomers are generally preferred over the threo isomers, erythro and threo referring to the relative positions of the hydroxy groups in the 3- and 5-positions (of the group of Formula II).

As between compounds of Formula I having identical R, R$_o$, R$_2$, R$_3$, R$_6$ and X groups, those wherein Z is a group of Formula II are generally preferred over those wherein Z is a group of Formula III.

The preferences set forth in the following two paragraphs apply to the compounds of Formula I wherein R$_7$ is free of centers of asymmetry as well as the compounds of Formula I wherein R$_7$ contains one or more centers of asymmetry. In the latter case they represent the preferred configurations of the indicated positions.

The preferred stereoisomers of the compounds of Formula I wherein X is a direct bond or —CH=CH—, and Z is a group of Formula II are the 3R,5S and 3R,5R isomers and the racemate of which each is a constituent, i.e., the 3R,5S-3S,5R (erythro) and 3R,5R-3S,5S (threo) racemates, with the 3R,5S isomer and the racemate of which it is a constituent being more preferred and the 3R,5S isomer being most preferred.

The preferred stereoisomers of the compounds of Formula I wherein X is —(CH$_2$)$_m$—, and Z is a group of Formula II are the 3R,5R and 3R,5S isomers and the racemate of which each is a constituent, i.e., the 3R,5R-3S,5S (erythro) and 3R,5S-3S,5R (threo) racemates, with the 3R,5R isomer and the racemate of which it is a constituent being more preferred and the 3R,5R isomer being most preferred.

The preferred stereoisomers of the compounds of Formula I wherein X is a direct bond or —CH=CH—, and Z is a group of Formula III are the 4R,6S and 4R,6R isomers and the racemate of which each is a constituent, i.e., the 4R,6S-4S,6R (trans lactone) and 4R,6R-4S,6S (cis lactone) racemates, with the 4R,6S isomer and the racemate of which it is a constituent being more preferred and the 4R,6S isomer being most preferred.

The preferred stereoisomers of the compounds of Formula I wherein X is —(CH$_2$)$_m$—, and Z is a group of Formula III are the 4R,6R and 4R,6S isomers and the racemate of which each is a constituent, i.e., the 4R,6R-4S,6S (trans lactone) and 4R,6S-4S,6R (cis lactone) racemates, with the 4R,6R isomer and the racemate of which it is a constituent being more preferred and the 4R,6R isomer being most preferred.

Each of the preferences set forth above applies, not only to the compounds of Formula I, but also to the compounds of Formulae IA and IB and those of Groups IAa, IAb, IBa and IBb as well as to every other subgroup thereof set forth infra, e.g., Groups (i)–(cxcviii) unless otherwise indicated. When any preference contains a variable, the preferred significances of that variable apply to the preference in question, unless otherwise indicated.

Representative groups of compounds of Formulae I, Ia and Ib and of Groups IAa, IAb, IBa and IBb include those of each of these seven groups wherein one of R and R$_o$ is

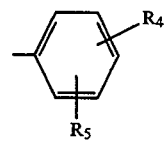

and the other is C$_{1-3}$alkyl, n-butyl or i-butyl, R$_1$ is C$_{1-3}$alkyl, n-butyl or i-butyl, R$_2$ is hydrogen, C$_{1-3}$alkyl, n-butyl, i-butyl, C$_{1-3}$alkoxy, n-butoxy, i-butoxy, trifluoromethyl, fluoro, chloro, phenoxy or benzyloxy, R$_4$ is other than t-butyl, R$_{5a}$ is hydrogen, and X is —(CH$_2$)$_n$— or

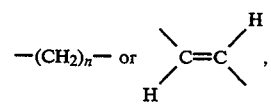, each of the other variables being as defined above.

Preferred groups of compounds of Formula I include the compounds (i) of Group IAa wherein R$_1$ is R$_1'$, R$_2$ is R$_2'$, R$_3$ is R$_3'$, R$_4$ is R$_4'$, R$_5$ is R$_5'$, R$_{5a}$ is R$_{5a}'$, R$_6$ is R$_6'$, R$_7$ is R$_7'$, and X is X', (ii) of (i) wherein when R$_2'$ is other than hydrogen and R$_3'$ is hydrogen, R$_2'$ is in the 4-, 5- or 6-position; when both $R_2'$ and $R_3'$ are other than hydrogen, at least one of them is in the 5- or 6-position and neither of them is in the 7-position; when both $R_4'$ and $R_5'$ are other than hydrogen and $R_{5a}'$ is hydrogen, at least one of $R_4'$ and $R_5'$ is in a meta or para position; and when each of $R_4'$, $R_5'$ and $R_{5a}'$ is other than hydrogen, at least two of them are in meta or para positions, (iii)–(iv) of (i) and (ii) wherein $R_6$ is $R_6'$, especially hydrogen, (v)–(vi) of (i) and (ii) wherein $R_1$ is $C_{1-3}$alkyl, $R_2$ is $R_2''$, $R_3$ is $R_3''$, $R_4$ is $R_4''$, $R_5$ is $R_5''$, $R_6$ is $R_6''$, especially hydrogen, $R_7$ is $R_7''$, and X is X'', (vii) of (i) wherein $R_1$ is $C_{1-3}$alkyl, $R_2$ is $R_2'''$, $R_3$ is $R_3'''$, $R_4$ is $R_4'''$, $R_5$ is $R_5'''$, $R_{5a}$ is hydrogen, $R_6$ is hydrogen, $R_7$ is $R_7''$, and X is

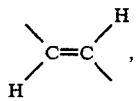

(viii)–(xiii) of (i)–(vi) wherein any M is M', (xiv) of Group IAb wherein $R_1$ is $R_1'$, $R_2$ is $R_2'$, $R_3$ is $R_3'$, $R_4$ is $R_4'$, $R_5$ is $R_5'$, $R_{5a}$ is $R_{5a}'$, $R_6$ is $R_6'$, and X is X', (xv) of (xiv) wherein when $R_2'$ is other than hydrogen and $R_3'$ is hydrogen, $R_2'$ is in the 4-, 5- or 6-position; when both $R_2'$ and $R_3'$ are other than hydrogen, at least one of them is in the 5- or 6-position and neither of them is in the 7-position; when both $R_4'$ and $R_5'$ are other than hydrogen and $R_{5a}'$ is hydrogen, at least one of $R_4'$ and $R_5'$ is in a meta or para position; and when each of $R_4'$, $R_5'$, and $R_{5a}'$ is other than hydrogen, at least two of them are in meta or para positions, (xvi)–(xvii) of (xiv) and (xv) wherein $R_6$ is $R_6''$, especially hydrogen, (xviii)–(xix) of (xiv) and (xv) wherein $R_1$ is $C_{1-3}$alkyl, $R_2$ is $R_2''$, $R_3$ is $R_3''$, $R_4$ is $R_4''$, $R_5$ is $R_5''$, $R_6$ is $R_6''$, especially hydrogen, and X is X'', (xx) of (xiv) wherein $R_1$ is $C_{1-3}$alkyl, $R_2$ is $R_2'''$, $R_3$ is $R_3'''$, $R_4$ is $R_4'''$, $R_5$ is $R_5'''$, $R_{5a}$ is hydrogen, $R_6$ is hydrogen, and X is

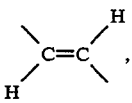

(xxi) of Group IBa wherein $R_1$ is $R_1'$, $R_2$ is $R_2'$, $R_3$ is $R_3'$, $R_4$ is $R_4'$, $R_5$ is $R_5'$, $R_{5a}$ is $R_{5a}'$, $R_6$ is $R_6'$, $R_7$ is $R_7'$, and X is X', (xxii) of (xxi) wherein when $R_2'$ is other than hydrogen and $R_3'$ is hydrogen, $R_2'$ is in the 4-, 5- or 6-position; when both $R_2'$ and $R_3'$ are other than hydrogen, at least one of them is in the 5- or 6-position and neither of them is in the 7-position; when both $R_4'$ and $R_5'$ are other than hydrogen and $R_{5a}'$ is hydrogen, at least one of $R_4'$ and $R_5'$ is in a meta or para position; and when each of $R_4'$, $R_5'$ and $R_{5a}'$ is other than hydrogen, at least two of them are in meta or para positions, (xxiii)–(xxiv) of (xxi) and (xxii) wherein $R_6$ is $R_6''$, especially hydrogen, (xxv)–(xxvi) of (xxi) and (xxii) wherein $R_1$ is $C_{1-3}$alkyl, $R_2$ is $R_2''$, $R_3$ is $R_3''$, $R_4$ is $R_4''$, $R_5$ is $R_5''$, $R_6$ is $R_6''$, especially hydrogen, $R_7$ is $R_7''$, and X is X'', (xxvii)–(xxxii) of (xxi)–(xxvi) wherein any M is M', (xxxiii) of Group IBb wherein $R_1$ is $R_1'$, $R_2$ is $R_2'$, $R_3$ is $R_3'$, $R_4$ is $R_4'$, $R_5$ is $R_5'$, $R_{5a}$ is $R_{5a}'$, $R_6$ is $R_6'$, and X is X', (xxxiv) of (xxxiii) wherein when $R_2'$ is other than hydrogen and $R_3'$ is hydrogen, $R_2'$ is in the 4-, 5- or 6-position; when both $R_2'$ and $R_3'$ are other than hydrogen, at least one of them is in the 5- or 6-position and neither of them is in the 7-position; when both $R_4'$ and $R_5'$ are other than hydrogen and $R_{5a}'$ is hydrogen, at least one of $R_4'$ and $R_5'$ is in a meta or para position; and when each of $R_4'$, $R_5'$ and $R_{5a}'$ is other than hydrogen, at least two of them are in meta or para positions, (xxxv)–(xxxvi) of (xxxiii) and (xxxiv) wherein $R_6$ is $R_6''$, especially hydrogen, (xxxvii)–(xxxviii) of (xxxiii) and (xxxiv) wherein $R_1$ is $C_{1-3}$alkyl, $R_2$ is $R_2''$, $R_3$ is $R_3''$, $R_4$ is $R_4''$, $R_5$ is $R_5''$, $R_6$ is $R_6''$, especially hydrogen, and X is X'', (xxxix)–(xl) of Groups IAa and IBa wherein $R_1$ is $R_1''$, $R_2$ is $R_2''''$, $R_3$ is $R_3''$, $R_4$ is $R_{4a}$, $R_5$ is $R_5'''$, $R_{5a}$ is $R_{5a}'$, $R_6$ is $R_6''$, especially hydrogen, $R_7$ is $R_7''$ and X is $X_a'$, (xli)–(xlii) of (xxxix) and (xl) wherein when $R_2''''$ is other than hydrogen and $R_3''$ is hydrogen, $R_2''''$ is in the 4-, 5- or 6-position; when both $R_2''''$ and $R_3''$ are other than hydrogen, neither of them is in the 7-position; when both $R_{4a}$ and $R_5'''$ are other than hydrogen and $R_{5a}'$ is hydrogen, at least one of $R_{4a}$ and $R_5'''$ is in a meta or para position; and when each of $R_{4a}$, $R_5'''$ and $R_{5a}'$ is other than hydrogen, at least two of them are in meta or para positions, (xliii)–(xlvi) of (xxxix)–(xlii) wherein $R_6$ is hydrogen, and X is

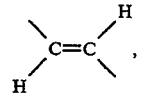

(xlvii)–(l) of (xliii)–(xlvi) wherein $R_1$ is $C_{1-3}$alkyl, $R_2$ is hydrogen, $R_3$ is hydrogen, and $R_4$ is $R_4'''$, (li)–(liv) of (xlvii)–(l) wherein $R_7$ is M, especially M' and most especially sodium, (lv)–(lvi) of Groups IAb and IBb wherein $R_1$ is $R_1''$, $R_2$ is $R_2''''$, $R_3$ is $R_3''$, $R_4$ is $R_{4a}$, $R_5$ is $R_5'''$, $R_{5a}$ is $R_{5a}'$, $R_6$ is $R_6''$, especially hydrogen, and X is $X_a'$, (lvii)–(lviii) of (lv) and (lvi) wherein when $R_2''''$ is other than hydrogen and $R_3''$ is hydrogen, $R_2''''$ is in the 4-, 5- or 6- position; when both $R_2''''$ and $R_3''$ are other than hydrogen, neither of them is in the 7-position; when both $R_{4a}$ and $R_5'''$ are other than hydrogen and $R_{5a}'$ is hydrogen, at least one of $R_{4a}$ and $R_5'''$ is in a meta or para position; and when each of $R_{4a}$, $R_5'''$ and $R_{5a}'$ is other than hydrogen, at least two of them are in meta or para positions, (lix)–(lxii) of (lv)–(lviii) wherein $R_6$ is hydrogen, and X is

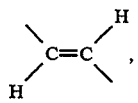

(lxiii)–(lxvi) of (lix)–(lxii) wherein $R_1$ is $C_{1-3}$alkyl, $R_2$ is hydrogen, $R_3$ is hydrogen, and $R_4$ is $R_4'''$, (lxvii)–(cvii) of (i)–(xiii), (xxi)–(xxxii) and (xxxix)–(liv) wherein the hydroxy groups in the 3- and 5-positions (of the group of Formula II) have the erythro configuration, (cviii)–(cxlviii) the 3R,5S enantiomers of the compounds of (lxvii)–(cvii) wherein X is —CH=CH— and the 3R,5R enantiomers of the compounds of these groups wherein X is —(CH$_2$)$_m$—, (cxlix)–(clxxiii) of (xiv)–(xx), (xxxiii)–(xxxviii) and (lv)–(lxvi) wherein the hydroxy group on the lactone ring is trans to X (i.e., the trans lactones), and (clxxiv)–(cxcviii) the 4R,6S enantiomers of the compounds of (cxlix)–(clxxiii) wherein X is —CH=CH— and the 4R,6R enantiomers of the compounds of these groups wherein X is —(CH$_2$)$_m$—.

Groups (lxvii)–(cvii) embrace the 3R,5S-3S,5R racemate and the 3R,5S and 3S,5R enantiomers of the compounds wherein X is —CH=CH— (the 3S,5R enantiomer being least preferred) and the 3R,5R-3S,5S racemate and the 3R,5R and 3S,5S enantiomers of the compounds wherein X is —(CH$_2$)$_m$— (the 3S,5S enantiomer being least preferred).

Groups (cxlix)–(clxxiii) embrace the 4R,6S-4S,6R racemate and the 4R,6S and 4S,6R enantiomers of the compounds wherein X is —CH=CH— (the 4S,6R enantiomer being least preferred) and the 4R,6R-4S,6S racemate and the 4R,6R and 4S,6S enantiomers of the compounds wherein X is —(CH$_2$)$_m$— (the 4S,6S enantiomer being least preferred).

The compounds of Formula I may be synthesized as follows:

Reaction Scheme I

The compounds of Formula I wherein $R_6$ is hydrogen may be synthesized by the following series of reactions:

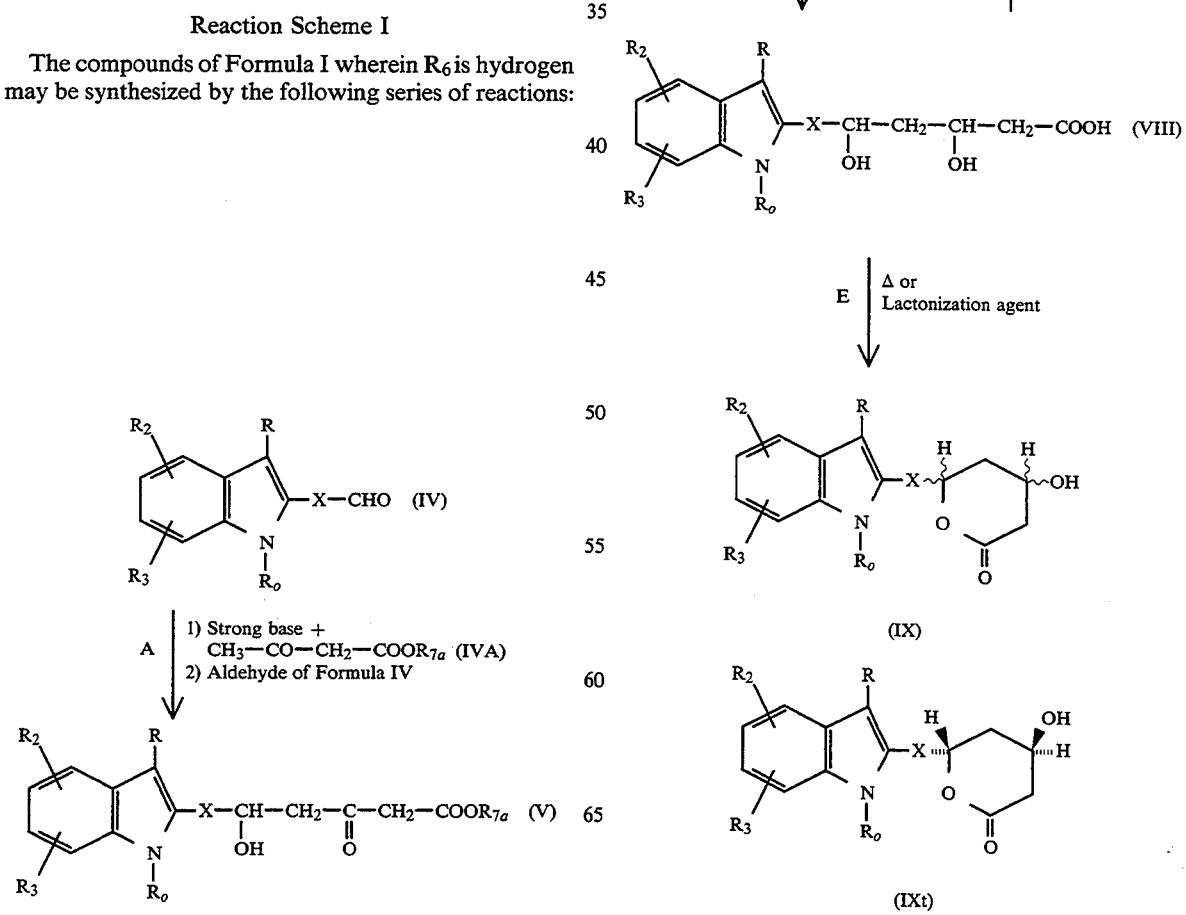

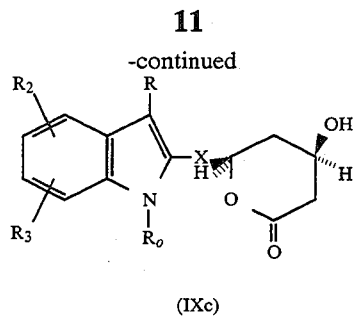
(IXc)
Reaction Scheme II
The compounds of Formula I wherein $R_6$ is $C_{1-3}$ alkyl may be synthesized by the following series of reactions:
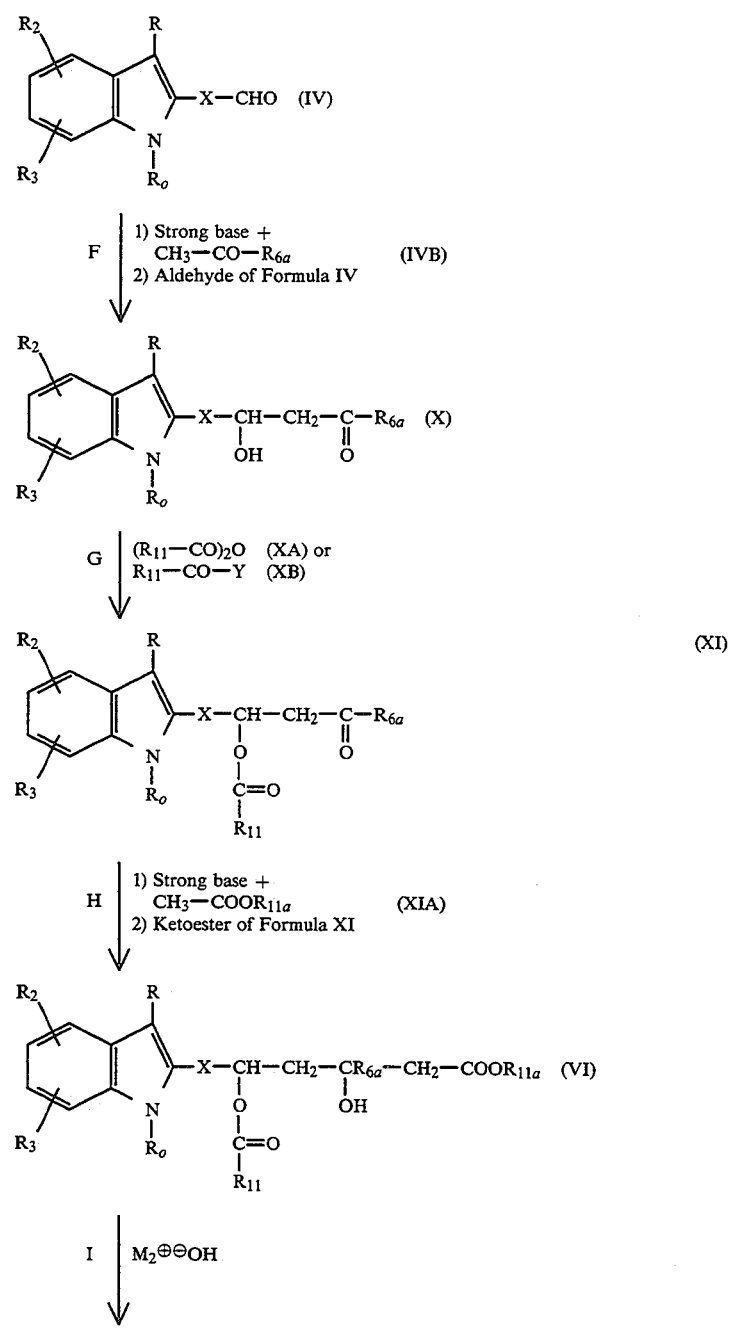

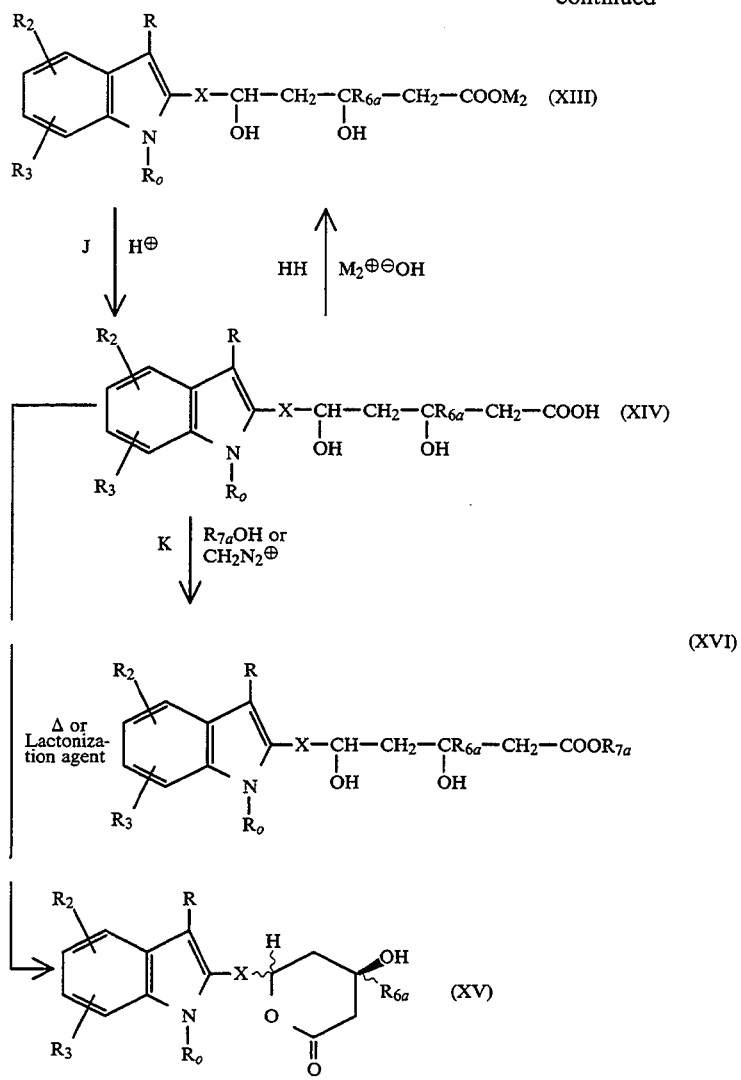
Reaction Scheme III
The compounds of Formula IV wherein X is a direct bond and those wherein X is
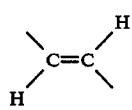
may be synthesized by the following series of reactions:
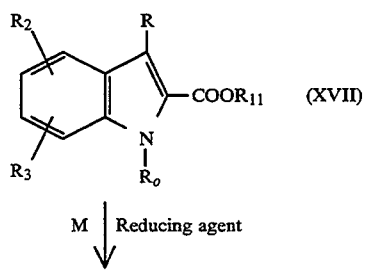
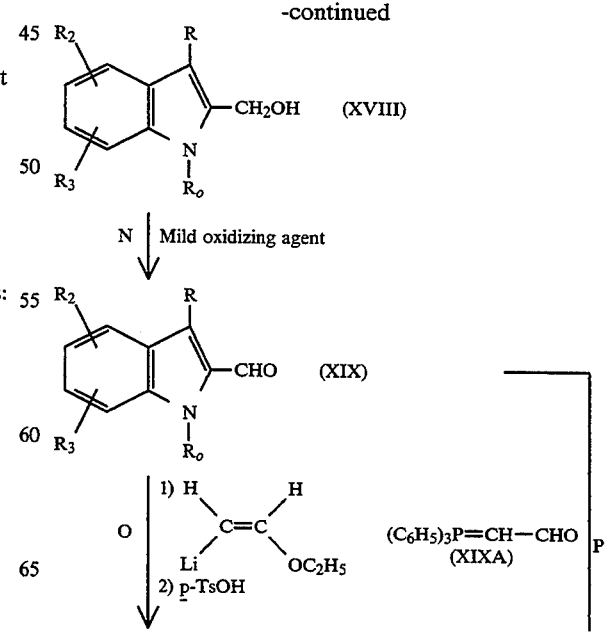

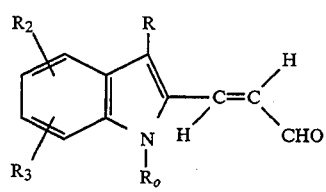 (XX)

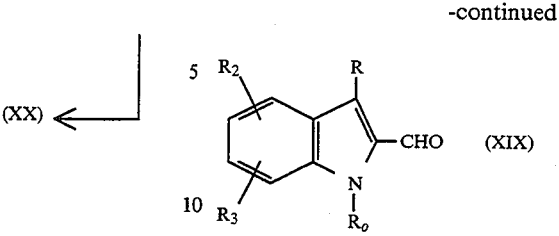 (XIX)

S | Reducing agent

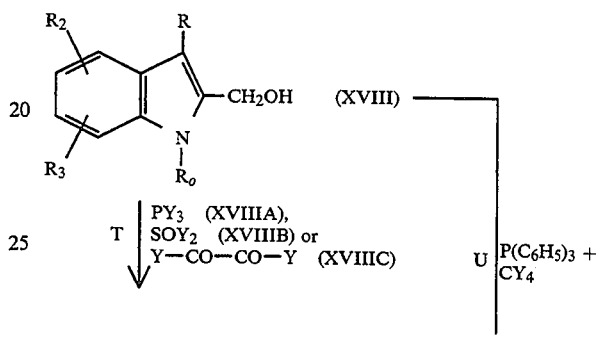

Reaction Scheme IV

The compounds of Formula XVII wherein $R_o$ is $R_1$ may be synthesized as follows:

T | PY$_3$ (XVIIIA), SOY$_2$ (XVIIIB) or Y—CO—CO—Y (XVIIIC)

U | P(C$_6$H$_5$)$_3$ + CY$_4$

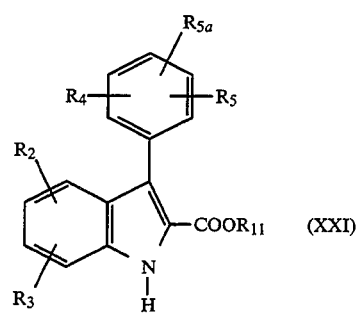 (XXI)

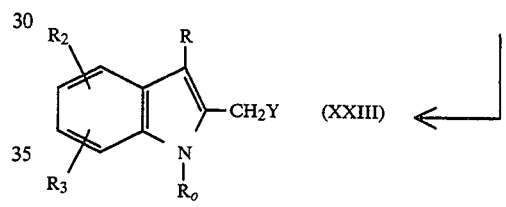 (XXIII)

Q | 1) Strong base
2) R$_1$—I

V | P(C$_6$H$_5$)$_3$

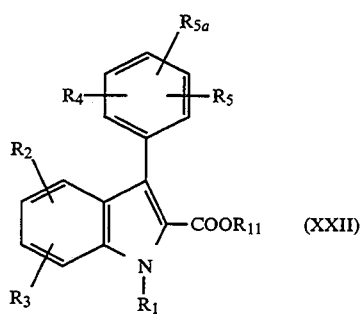 (XXII)

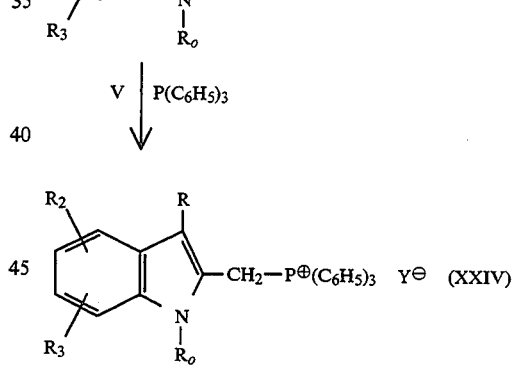 (XXIV)

Reaction Scheme V

The compounds of Formula IX wherein X is —CH═CH— may also be synthesized by the following series of reactions:

W | 1) Strong base
2)  (XXV)

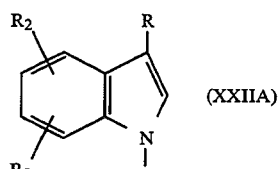 (XXIIA)

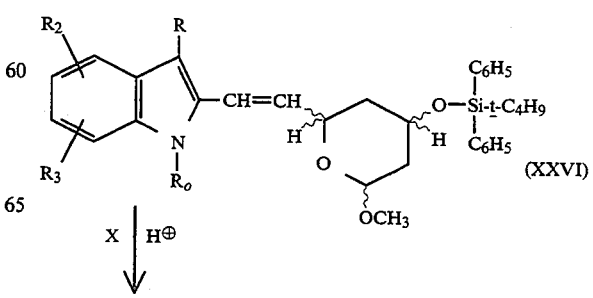 (XXVI)

R | 1) POY$_3$ (XXIIB) + (R$_{12}$)$_2$N—CHO (XXIIC)
2) Compound of Formula XXIIA
3) ⊖OH

X | H⊕

-continued

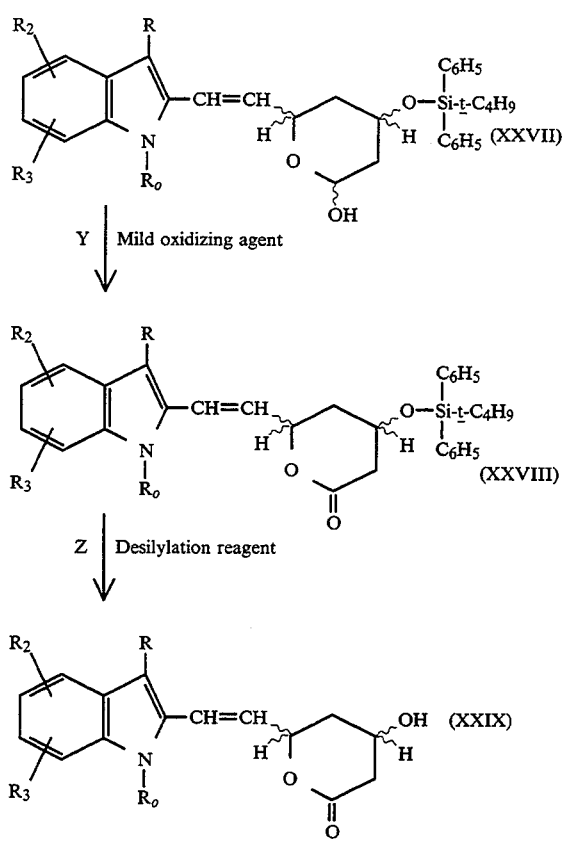

Reaction Scheme VI

The compounds of Formula XX are preferably synthesized by the following reaction:

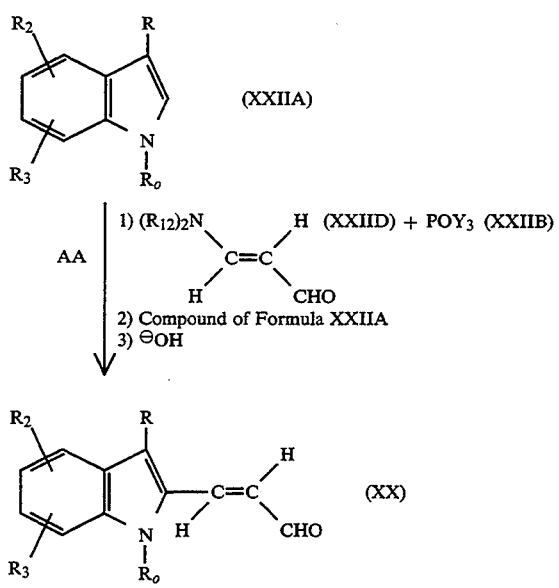

Reaction Scheme VII

The compounds of Formula IV wherein X is —(CH$_2$)$_m$— may be synthesized by the following series of reactions:

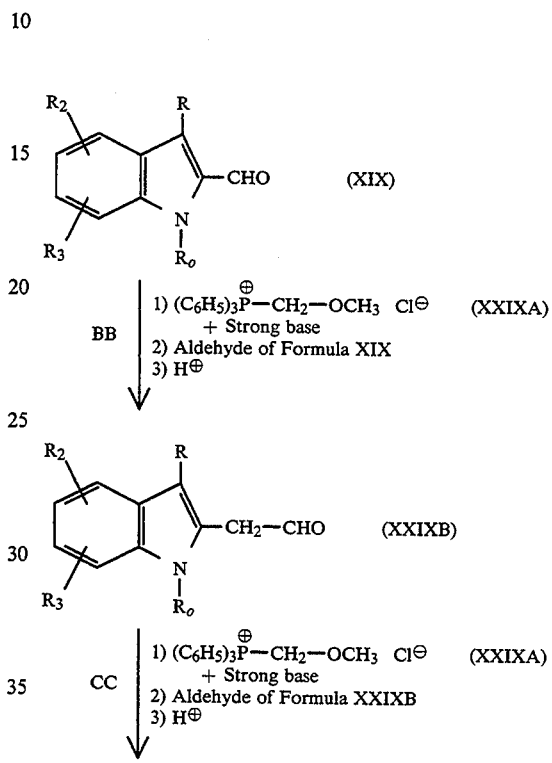

Reaction Scheme VIII

The compounds of Formula I wherein Z is a group of Formula II wherein R$_7$ is R$_{7b}$ or M$_2$ may also be synthesized as follows:

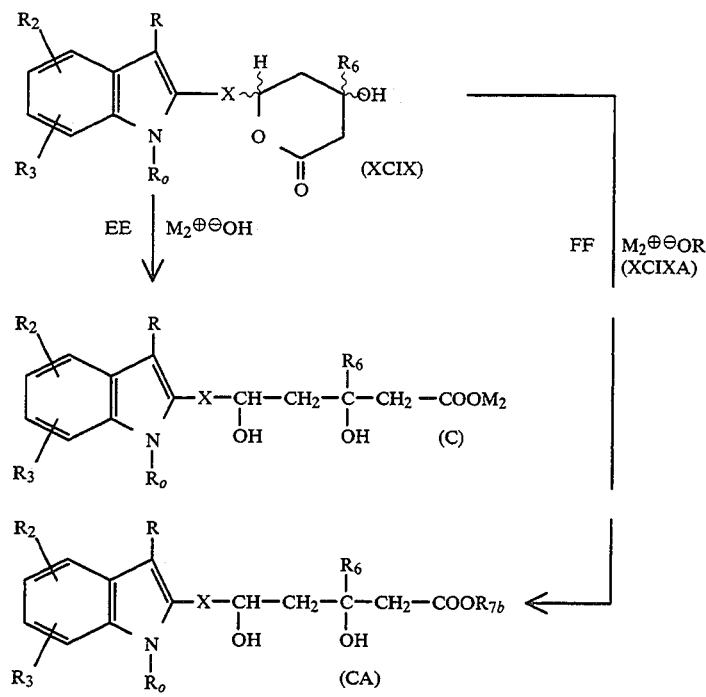
Reaction Scheme IX
Two isomers of the compound of Formula XXV may be synthesized by the following series of reactions:
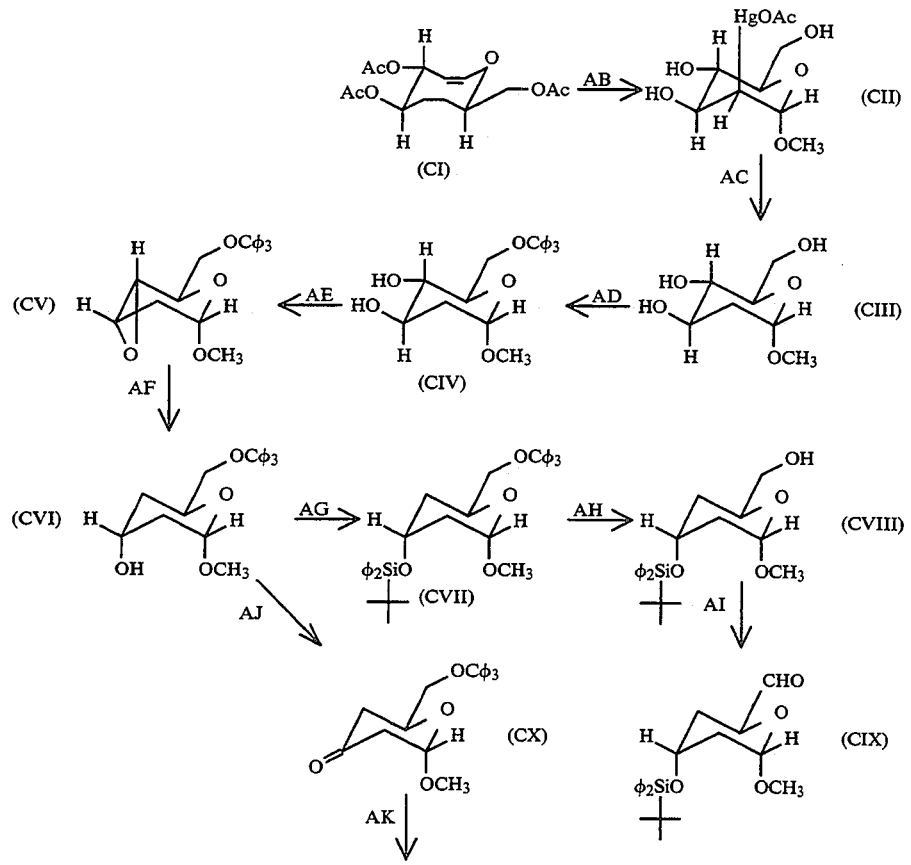

-continued

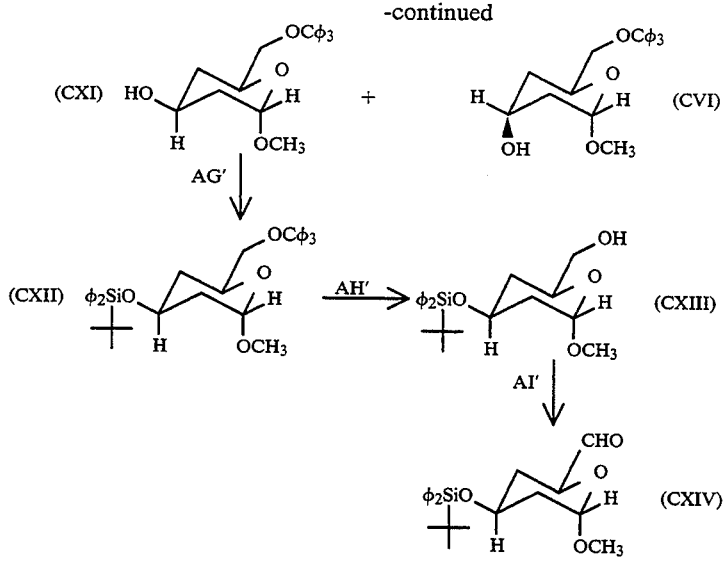

In the above formulae, $R_{6a}$ is $C_{1-3}$alkyl, preferably $C_{1-2}$alkyl and most preferably methyl, $R_{7a}$ is $C_{1-3}$alkyl, n-butyl, i-butyl, t-butyl or benzyl, preferably $C_{1-3}$alkyl and most preferably $C_{1-2}$alkyl, $R_{11}$ is $C_{1-2}$alkyl, preferably methyl, $R_{11a}$ is $C_{1-3}$alkyl, n-butyl or t-butyl, preferably ethyl or t-butyl, each $R_{12}$ is independently $C_{1-3}$alkyl, preferably $C_{1-2}$alkyl and more preferably methyl, each Y is chloro or bromo, preferably chloro, $M_2$ is M, preferably sodium or potassium, and each of the other variables is as set forth above.

In Reaction Scheme IX,

Ac is acetyl,

Φ is phenyl, and

⊥ is t-butyl.

As utilized herein, terms such as "solvent" and "solvent system" embrace mixtures of solvents and imply that the reaction medium is a liquid at the desired reaction temperature. It should, therefore, be understood that not all of the solvents listed for a particular reaction may be utilized for the entire recited temperature range. It should also be understood that the solvent must be at least substantially inert to the reactants employed, intermediates generated and end products under the reaction conditions utilized.

The term "an inert atmosphere", as utilized herein, means an atmosphere that does not react with any of the reactants, intermediates or end products or otherwise interfere with the reaction. While a carbon dioxide atmosphere is suitable for some reactions, the inert atmosphere is usually nitrogen, helium, neon, argon or krypton, or a mixture thereof, and preferably is nitrogen. Most reactions, including those where the use of an inert atmosphere is not specified, are carried out under such an atmosphere for convenience. Usually, the inert atmosphere is dry nitrogen in order to maintain anhydrous conditions.

In Reaction A, the dianion of the acetoacetic acid ester of Formula IVA is generated with 2-2.2 equivalents of a strong base per mole of said ester, and the resulting dianion is reacted with the compound of Formula IV. Among the strong bases that may be employed are n-butyllithium, lithium diisopropylamide and sodium hydride. However, sodium hydride can be used only to generate a monoanion; it cannot be used to generate a dianion. Consequently, when sodium hydride is used to generate the monoanion, 1-1.1 equivalents thereof are utilized and then 1-1.1 equivalents of n-butyllithium or lithium diisopropylamide are utilized to generate the dianion from the monoanion. The molar ratio of the acetoacetic acid ester of Formula IVA to the compound of Formula IV is preferably 1-2:1, more preferably 1.4-1.8:1. The temperature for both steps is conveniently $-80°$-$10°$ C., preferably $-20°$-$5°$ C. Both steps of the reaction are relatively rapid; the dianion is typically generated over the course of 20-90 minutes while the reaction of the dianion with the compound of Formula IV is generally run for 20-120 minutes. The reaction is carried out under an inert atmosphere in an anhydrous inert organic solvent, for example an ether solvent such as tetrahydrofuran, diethyl ether, 1,2-dimethoxyethane or 1,2-diethoxyethane, or a mixture thereof. The resulting compound of Formula V is a racemate.

The initial step of Reaction A is preferably carried out by generating the monoanion of the acetoacetic acid ester of Formula IVA with 1-1.05 equivalents of sodium hydride which is then treated with 1-1.05 equivalents of n-butyllithium, per mole of said acetoacetic acid ester in each case, at a temperature of about $-15°$ C.-$10°$ C.

In Reaction B, the keto group of the compound of Formula V is reduced to a hydroxy group with a mild reducing agent such as sodium borohydride or, preferably, a complex of t-butylamine and borane in an inert organic solvent such as a lower alkanol, preferably ethanol, conveniently at a temperature of $-25°$-$30°$ C., utilizing at least 1, for example 2-8, equivalents of transferable hydride per mole of compound of Formula V, under an inert atmosphere. The reaction time is suitably 1-8 hours. The compounds of Formula VI exist in four stereoisomeric forms; however, if an optically pure starting material of Formula V is utilized, only two optical isomers (diastereoisomers) of the resulting compound of Formula VI are obtained. The ratio of the erythro isomer(s) to the threo isomer(s) is generally about 3:2-2:3.

It is often possible to separate the erythro racemate from the threo racemate by formation of a cyclic borate ester, separation of the borate ester derived from the erythro racemate by fractional crystallization and cleavage of the cyclic borate ester by methanolysis. Conveniently, the compound of Formula VI is reacted with 0.97–1 mole of boric acid per mole of the compound of Formula VI (assuming 100% yield of said compound) in a large excess of isopropanol (e.g., 5–8 liters per mole of said compound) at 70° C.-reflux, preferably at reflux, for 5–30 minutes to form the cyclic isopropyl borate ester. By repeated fractional crystallization from isopropanol (e.g., three to five times), the pure or virtually pure crystalline erythro cyclic isopropyl borate ester is obtained, with each mother liquor being enriched with the threo compound, the threo:erythro ratio generally decreasing with each successive mother liquor. The pure or nearly pure erythro cyclic borate ester is then cleaved by methanolysis. Conveniently, the erythro cyclic borate ester is treated in a large excess of methanol (e.g., 4–8 liters per mole of the erythro cyclic borate ester) at 55° C.-reflux, preferably at reflux for 0.5–1.5 hours, preferably 0.75–1 hour, to obtain the pure or nearly pure erythro racemate of the compound of Formula VI. The threo racemate may be isolated from the recrystallization mother liquors, purified, if necessary, and similarly cleaved to obtain the pure or nearly pure threo racemate of the compound of Formula VI. This procedure is also applicable to the compounds of Formula XVI. It constitutes the invention of Bernhard Prager.

However, it is preferred to utilize a stereoselective reduction in order to maximize production of a mixture of the erythro stereoisomers (racemate) of which the preferred stereoisomer (as set forth above) is a constituent. Stereoselective Reaction B is preferably carried out in three steps. In the first step, the ketoester of Formula V is treated with a tri(primary or secondary $C_{2-4}$alkyl) borane, preferably triethylborane or tri-n-butylborane, and air to form a complex. The molar ratio of the trialkylborane to the ketoester of Formula V is preferably 1–1.25:1, more preferably 1.02–1.2:1, and 0.5–8 liters, preferably 0.75–6.5 liters, of air (at 25° C. and 760 mm. Hg) per mole of the ketoester of Formula V are typically used. The reaction temperature is suitably 0°–50° C., preferably 20°–30° C. and the reaction time is suitably 0.5–6 hours, preferably 0.5–3.5 hours. The first step is carried out in an anhydrous inert organic solvent, preferably an ether solvent such as tetrahydrofuran, diethyl ether, 1,2-dimethoxyethane or 1,2-diethoxyethane, with tetrahydrofuran being the most preferred solvent. In the second step, the complex is reduced with sodium borohydride, preferably in the same solvent as utilized for the first step, at $-100°$ to $-40°$ C., preferably $-90°$ to $-70°$ C., for 1–24 hours, preferably 2.5–18 hours. Preferably, 0.4–1.6, more preferably 1.0–1.5, moles of sodium borohydride per mole of the ketoester of Formula V are utilized. In the third step, the product of the second step is treated with, preferably, anhydrous methanol at 20°–40° C., preferably 20°–30° C., preferably for 0.7–5, more preferably 2–4, hours, to obtain the compound of Formula VI. The amount of methanol is not critical. However, a large excess, e.g., 50–500 moles per mole of ketoester of Formula V, is typically utilized.

Reactions C and I are conventional basic hydrolyses of esters. The ester of Formula VI or diester of Formula XII is treated with at least one equivalent of an inorganic hydroxide per mole of ester group to be hydrolyzed. Preferably, each mole of ester of Formula VI is treated with 1–1.2, preferably 1–1.1, and each mole of diester of Formula XII is treated with 2–2.3, preferably 2–2.2, equivalents of sodium hydroxide or potassium hydroxide in a mixture of water and a water-miscible organic solvent such as a lower alkanol, preferably a $C_{1-2}$alkanol, at a temperature of 20° C. to reflux, more preferably not in excess of 80° C. As is well-known, the reaction time is inversely related to the reaction temperature; however, a reaction time of 1–4 hours is generally acceptable. For example, a reaction time of 2–4 hours is particularly useful when the reaction is run at 20°–30° C. When it is desired to isolate the salt of Formula VII or XIII, it is preferable to utilize slightly less than one equivalent of the inorganic hydroxide, e.g., 0.95–0.98 equivalents per mole of ester group to be hydrolyzed.

Reactions D and J are conventional acidifications of a carboxylate salt to the corresponding carboxylic acid. The reactions are effected by treating the salt of Formula VII or XIII with a molar excess (e.g., 10–20%) of a dilute aqueous acid, e.g., 2N. hydrochloric acid, the pH of the reaction medium typically being 2–6, at, for example, 20°–25° C. for 1–10 minutes.

In Reactions E and L the 3,5-dihydroxycarboxylic acid of Formula VIII or XIV is cyclized to form a lactone of Formula IX or XV, respectively. The reaction may be carried out by heating the 3,5-dihydroxycarboxylic acid in an anhydrous inert organic solvent, for example a hydrocarbon such as benzene, toluene or a xylene, or a mixture thereof, preferably at 75° C.-reflux, more preferably not in excess of 150° C., for 3–18 hours, optionally using a Dean-Stark apparatus if the solvent forms an azeotrope with water. The reaction is conveniently run by refluxing the 3,5-dihydroxycarboxylic acid of Formula VIII or XIV in benzene for 8 hours. Preferably, however, the dihydroxycarboxylic acid of Formula VIII or XIV is treated with a lactonization agent, e.g., a carbodiimide, preferably a water-soluble carbodiimide such as N-cyclohexyl-N'-[2-(N''-methylmorpholinium)ethyl]carbodiimide p-toluenesulfonate, in an anhydrous inert organic solvent, e.g., a halogenated lower alkane, preferably methylene chloride. When a carbodiimide, such as the aforementioned carbodiimide, is utilized, 1–1.2, preferably 1–1.1, moles thereof per mole of the dihydroxycarboxylic acid are conventionally utilized, the reaction temperature is typically 10°–35° C., preferably 20°–30° C., and the reaction time is conveniently 2–8 hours, preferably 3–4 hours, especially when the reaction temperature is 20°–30° C. The latter procedure often results in higher yields than the former. As is evident to those in the art, a racemic threo 3,5-dihydroxycarboxylic acid yields a racemic cis lactone and a racemic erythro 3,5-dihydroxycarboxylic acid yields a racemic trans lactone. Use of a mixture of threo and erythro 3,5-dihydroxycarboxylic acids yields a mixture of cis and trans lactones (all four possible diastereoisomers). Likewise if a single enantiomer of the 3,5-dihydroxycarboxylic acid is utilized, a single enantiomer of the lactone is obtained. For example, lactonization of a 3R,5S erythro dihydroxycarboxylic acid of Formula VIII yields a 4R,6S lactone of Formula IXt.

In Reaction F, a monoanion of the ketone of Formula IVB is generated by treating a solution of the ketone in an anhydrous inert organic solvent, such as those utilized for Reaction A, with 1–1.1 equivalents of a strong base such as lithium diisopropylamide per mole of said ketone followed by reaction of the monoanion with the aldehyde of Formula IV in the same solvent. The molar ratio of the ketone of Formula IVB to the aldehyde of Formula IV is preferably 3:1. The reaction is carried out under an inert atmosphere. The reaction temperature is suitably $-80°--40°$ C., preferably $-80°--75°$ C., and each of the two steps is generally carried out over a 15–90 minute period. If the product contains, in addition to the compound of Formula X, a compound not of said formula, the compound of Formula X is separated therefrom by conventional techniques, e.g., column chromatography or high pressure liquid chromatography.

In Reaction G the compound of Formula X is acylated with, for example, an acid anhydride of Formula XA or an acyl halide of Formula XB in the presence of a base such as pyridine or triethylamine. Conveniently, the compound of Formula X is treated with 1–3, preferably 2, moles of said acid anhydride or acyl halide per mole of the compound of Formula X in an excess of pyridine or preferably in an ether solvent such as tetrahydrofuran containing 1–4, preferably 2.5–3, moles of a tertiary amine base such as pyridine or, preferably, 4-dimethylaminopyridine per mole of the compound of Formula X at 10°–50° C., preferably 20°–30° C., for 2–18, preferably 4–12, hours.

Reaction H is also a two-step reaction. First, the ester of Formula XIA is treated with a strong base such as lithium diisopropylamide to form a monoanion, the molar ratio of the latter to the former being 1–1.1:1. The reaction is carried out in an anhydrous inert organic solvent, for example an ether such as diethyl ether, 1,2-dimethoxyethane, 1,2-diethoxyethane or, preferably, tetrahydrofuran, under an inert atmosphere. The reaction temperature is conveniently $-80°-0°$ C., and the reaction time is usually 15–60 minutes. In the second step, said monoanion is reacted with the ester of Formula XI under an inert atmosphere in the same solvent system as utilized. for the first step, the molar ratio of the compound of Formula XIA to the compound of Formula XI preferably being 3:1. The reaction temperature is conveniently $-80°--40°$ C., preferably $-80°--70°$ C., and the reaction time is typically 15–90 minutes.

Reaction K is a conventional acid catalyzed esterification. Conveniently, the compound of Formula XIV is treated with a large excess of an alcohol of the formula $R_{7a}$—OH at 20°–40° C. for 2–12 hours in the presence of a catalytic amount of an acid such as p-toluenesulfonic acid. The excess alcohol serves as the solvent. However, it is preferred to synthesize the compounds of Formula XVI wherein $R_{7a}$ is methyl by reacting the compound of Formula XIV with diazomethane in, preferably, an anhydrous inert ether solvent such as diethyl ether, tetrahydrofuran 1,2-dimethoxyethane or 1,2-diethoxyethane, more preferably diethyl ether, at, for example, 0°–30° C., preferably 20°–25° C., for, typically, 10–30 minutes, preferably under an inert atmosphere. Generally, 1–4 moles, preferably 2–3 moles, of diazomethane per mole of the compound of Formula XIV are utilized.

Reaction M is a conventional reduction of a lower alkyl ester to the corresponding primary alcohol utilizing a metal hydride reducing agent such as lithium aluminum hydride or, preferably, diisobutylaluminum hydride in an anhydrous inert organic solvent, for example, an ether such as tetrahydrofuran, diethyl ether, 1,2-dimethoxyethane or 1,2-diethoxyethane, preferably tetrahydrofuran. The reaction is preferably carried out under an inert atmosphere. The reaction temperature is suitably $-80°$ C.-reflux, preferably not in excess of 70° C., more preferably $-80°-25°$ C., and the reaction time is suitably 3–12 hours. At least two equivalents of transferable hydride, preferably 4–4.4 equivalents, per mole of the compound of Formula XVII are used.

In Reaction N the alcohol of Formula XVIII is oxidized under mild conditions to the aldehyde of Formula XIX. Preferably, the alcohol of Formula XVIII is treated with a large molar excess, e.g., 10–30 moles, of manganese dioxide per mole of said alcohol in an inert anhydrous organic solvent, for example, an ether such as diethyl ether, tetrahydrofuran, 1,2-dimethoxyethane or 1,2-diethoxyethane, at a temperature of 20° C.-reflux (but not in excess of 80° C.). While the reaction time is inversely related to the reaction temperature, a reaction time of 4–24 hours, preferably 10–18 hours, when the reaction temperature is 20°–30° C., is generally suitable.

Reaction 0 is a three-step reaction. In the first step, cis-1-ethoxy-2-tri-n-butylstannylethylene (prepared by adding 1 equivalent of ethoxyacetylene to tri-n-butyltin hydride at 50° C. over a period of 1 hour and heating under an inert atmosphere at 50°–55° C. for 3 hours and at 60°–70° C. for 1 hour) is reacted for 1–3, preferably 2, hours with 1–1.05 equivalents of n-butyllithium per mole of the tin compound at $-78°$ C. in anhydrous tetrahydrofuran under an inert atmosphere, the n-butyllithium/n-hexane solution being added dropwise, to form cis-1-lithium-2-ethoxyethylene. In the second step, said lithium compound is reacted with the compound of Formula XIX in the same solvent at $-80°--40°$ C., preferably at $-80°--70°$ C., under an inert atmosphere for 2–8, preferably 3–5, hours to form an intermediate compound. The molar ratio of the starting ethoxyethenyltin compound to the compound of Formula XIX is 1–1.15:1. In the third step, said intermediate compound is treated with a catalytic amount of p-toluenesulfonic acid (e.g., 0.5–2 g. of said acid per mole of the compound of Formula XIX) in an inert aqueous organic solvent, e.g., a mixture of water and tetrahydrofuran, for 1–5, preferably 1.5–2.5, hours, preferably at 20°–25° C.

Reaction P is a Wittig reaction and is carried out under conventional Wittig reaction conditions. The compound of Formula XIX is treated with 1–1.2 moles of the compound of Formula XIXA (per mole of the former) in an inert organic solvent, for example an anhydrous ether or hydrocarbon such as diethyl ether, 1,2-dimethoxyethane, 1,2-diethoxyethane, benzene or toluene, at 20° C.-reflux, preferably not in excess of 140° C. for 2–18 hours. It is preferable to carry out the reaction under an inert atmosphere.

In Reaction Q, the indole of Formula XXI is N-alkylated with an alkyl iodide of the formula $R_1$-I in a two-step reaction. In the first step, the indole of Formula XXI is treated with a strong base such as n-butyllithium or, preferably, sodium hydride, to generate an anion which, in the second step, is reacted with the alkyl iodide. Both steps are carried out in an anhydrous inert organic solvent such as tetrahydrofuran, diethyl ether, 1,2-dimethoxyethane, 1,2-diethoxyethane, diethylacetamide or, preferably, dimethylacetamide, the first step at $-20°-30°$ C. and the second step at $-15°$ C.-reflux, preferably not in excess of 80° C. most preferably 20°–30° C. The first step generally takes 15–60 minutes while the second step generally takes 1–5, usually 2–4, hours. 1–1.2 moles of the strong base per mole of the indole of Formula XXI are utilized in the first step, and 1-1.2 moles of the alkyl iodide per mole of said indole are utilized in the second step. An inert atmosphere is used for each step.

Reaction R is a three-step Vilsmeier-Haack reaction. In the exothermic initial step, the phosphorus oxyhalide of Formula XXIIB, preferably phosphorus oxychloride, and the N,N-dialkylformamide of Formula XXIIC, preferably dimethylformamide, are reacted to form an iminium salt. The reaction temperature is suitably 0°–35° C., preferably 0°–15° C., and the reaction time is suitably 5–60 minutes, preferably 10–20 minutes. Typically, 1–5 moles of the phosphorus oxyhalide and at least 1 mole of the N,N-dialkylformamide of Formula XXIIC, per mole of the indole of Formula XXIIA to be utilized in the second step, are used; preferably, however, 1.2–5 moles of the phosphorus oxyhalide and at least 1.5 moles of the N,N-dialkylformamide per mole of the indole of Formula XXIIA are used. If the N,N-dialkylformamide is a liquid, a large molar excess of it is utilized, the excess serving as the solvent. Alternatively, the reaction may be run in a liquid lower alkyl nitrile, such as acetonitrile, or a mixture thereof with the excess N,N-dialkylformamide. In the second step, the iminium salt is reacted with the indole of Formula XXIIA. The reaction temperature is suitably 60°–120° C., preferably 80°–105° C. (not in excess of reflux in each case) and while the reaction time is inversely related to the reaction temperature, it is suitably 3–18 hours, preferably 4–16 hours. The second step is carried out in the same solvent as the first step, both steps being carried out under anhydrous conditions and an inert atmosphere. In the third step, the adduct produced in the second step is decomposed with, for example, at least 4, preferably 4–6, more preferably 4, equivalents of an aqueous base, preferably aqueous sodium or potassium hydroxide, per mole of the phosphorus oxyhalide to liberate the aldehyde of Formula XIX. Preferably, the exothermic third step is carried out at −10°–45° C. The third step is conveniently carried out by slowly adding 4–6 equivalents (per mole of the phosphorus oxyhalide) of, for example, 15% sodium hydroxide solution to the adduct of the second step stirred at 10°–25° C., the rate of the addition being such that the temperature of the reaction mixture does not exceed 45° C. This reaction and Reaction AA are described in greater detail in application Ser. No. 06/635,304, filed on Jul. 27, 1984 by Robert E. Walkup and entitled Process For The Preparation of 2-Formyl-Indoles and now abandoned.

The aldehyde of Formula XIX is reduced to the alcohol of Formula XVIII in Reaction S with, preferably, a metal hydride reducing agent such as lithium aluminum hydride, diisobutylaluminum hydride or, preferably, sodium borohydride in an anhydrous inert organic solvent, e.g., an ether such as tetrahydrofuran, diethyl ether, 1,2-dimethoxyethane or 1,2-diethoxyethane or, when sodium borohydride is utilized, a mixture of such an ether and a lower alkanol, preferably a 9-15:1 mixture of tetrahydrofuran and methanol (by volume). The reaction temperature is suitably −5°–35° C., preferably 0°–25° C. At least one equivalent of transferable hydride per mole of the aldehyde of Formula XIX is utilized. When sodium borohydride is the reducing agent, preferably 0.25-1, more preferably 0.35-0.5, moles thereof per mole of the aldehyde of Formula XIX is utilized. The reaction is preferably carried out under an inert atmosphere for, for example, 0.5-3 hours.

Reaction T is a conventional phosphorus trihalide, thionyl halide or oxalyl halide halogenation reaction. It is conveniently carried out by reacting the alcohol of Formula XVIII with an excess of a phosphorus trihalide of Formula XVIIIA (e.g., one mole of phosphorus trihalide), 1-2, preferably 1.2-2, more preferably 1.5-1.8, moles of a thionyl halide of Formula XVIIIB or 1-1.2, preferably 1.05-1.1, moles of an oxalyl halide of Formula XVIIIC (per mole of the alcohol of Formula XVIII in each case) in an anhydrous inert organic solvent, preferably an ether such as diethyl ether or tetrahydrofuran, optionally containing a trace of dimethylformamide, at a temperature of 20°–35° C. for 4–25 hours when a phosphorus trihalide is utilized or a temperature of −10°–20° C., preferably −10°–10° C., more preferably −10°–5° C., for 2–4 hours when a thionyl halide or oxalyl halide is utilized.

In Reaction U the alcohol of Formula XVIII is reacted with 1-2, preferably 1-1.2, moles of triphenylphosphine and at least one mole of carbon tetrachloride or carbon tetrabromide (per mole of said alcohol in each case) at a temperature of −10° C.-reflux, preferably no higher than 120° C., for 4-18 hours. The reaction may be run neat (i.e., using an excess of carbon tetrachloride or carbon tetrabromide as the solvent) or in an ether or hydrocarbon solvent, for example, diethyl ether, tetrahydrofuran, benzene or toluene. When the reaction is run neat, the preferred temperature range is 25° C.-reflux, more preferably no higher than 100° C.

In Reaction V, the halomethylindole of Formula XXIII is reacted in an anhydrous inert organic solvent, for example a hydrocarbon such as benzene, toluene or xylene, or a mixture thereof, with 1-1.25 moles of triphenylphosphine per mole of the halomethylindole. The reaction temperature is conveniently 60° C.-reflux, preferably not in excess of 150° C., more preferably 100°–110° C., and, while the reaction time is inversely related to the reaction temperature, it is conveniently 1-8 hours, preferably 3-6 hours. The reaction is run under an inert atmosphere.

Reaction W is a two-step reaction. First, the phosphonium compound of Formula XXIV is treated with 1-1.1 moles of a strong base such as sodium hydride or n-butyllithium per mole of phosphonium compound in an anhydrous inert organic solvent, for example an ether or hydrocarbon such as tetrahydrofuran, benzene or toluene, under an inert atmosphere at a temperature of 0°–25° C. for 5-60 minutes. The resulting intermediate is, in the second step, reacted with an aldehyde of Formula XXV. The reaction temperature for the second step is conveniently −10° C.-reflux, preferably no higher than 80° C., more preferably 20°–30° C., the initial reaction temperature preferably being −10°–0° C., e.g., 0° C., the reaction time conveniently being 2-24 hours. The reaction solvent is conveniently the same as that utilized in the first step. The molar ratio of the aldehyde of Formula XXV to the phosphonium compound of Formula XXIV is conveniently 1-1.1:1. The product is a mixture of the compound having a trans double bond (the (E) compound) and the compound having a cis double bond (the (Z) compound), of which the former predominates. The (E) and (Z) compounds may be separated by conventional means and separately employed in the succeeding reactions or the mixture may be carried through the remaining reactions of Reaction Scheme V to obtain a mixture of the (E) and (Z) compounds of Formula XXIX which may be separated by conventional means, e.g., column chromatography or high pressure liquid chromatography. Alternatively, the (E) and (Z) compounds may be separated after Reaction X or Reaction Y.

The methoxy group on the tetrahydropyran ring of the compound of Formula XXVI is hydrolyzed to a hydroxy group with acid in Reaction X. The hydrolysis is conveniently carried out in an aqueous inert organic solvent containing an organic or mineral acid, e.g., a mixture of 10% hydrochloric acid and tetrahydrofuran or, preferably, 3:2:1 (by volume) glacial acetic acid/tetrahydrofuran/water at a temperature of 10°-100° C., preferably 60° C. with the latter acid system. While the reaction time is inversely related to the reaction temperature, a reaction time of 8-24 hours is generally acceptable, for example 18-19 hours when the reaction temperature is 60° C. This reaction is accompanied by some epimerization at the 6-carbon atom of the lactone ring. The use of aqueous hydrochloric acid results in more epimerization than does the use of a mixture of acetic acid, tetrahydrofuran and water.

In Reaction Y the hydroxypyran of Formula XXVII is oxidized to the lactone of Formula XXVIII under very mild conditions as is known in the art. For example, the compound of Formula XXVII is treated with 1-6, preferably 2-6, especially 2-5, moles of anhydrous N-methylmorpholine-N-oxide per mole of the compound of Formula XXVII and a catalytic amount of dichlorotris(triphenylphosphine)ruthenium II (e.g., 0.01-0.1, preferably 0.05-0.07, moles per mole of the compound of Formula XXVII) at 0°-40° C., preferably 20°-30° C., in an anhydrous inert organic solvent, e.g., dimethylformamide or, preferably, acetone, for 5-60 minutes, preferably under an inert atmosphere. (See Sharpless et al., Tetrahedron Letters 1976, 2503-2506.) Alternatively, an excess of silver carbonate on Celite ® may be utilized. Suitable solvents include hydrocarbons such as benzene, toluene and the xylenes. The reaction temperature is conveniently 0° C.-reflux, preferably no higher than 150° C., more preferably 100° C.-reflux, and the reaction time is conveniently 1-18 hours.

In Reaction Z, the silyl group of the compound of Formula XXVIII is cleaved under mild conditions with, for example, a fluoride reagent such as tetra-n-butylammonium fluoride in an anhydrous inert organic medium containing glacial acetic acid, preferably tetrahydrofuran containing 1.2-1.8 moles of glacial acetic acid per mole of the fluoride compound. The reaction temperature is suitably 20°-60° C., preferably 20°-30° C., and the reaction time is suitably 2-24 hours, particularly when the reaction temperature is 20°-30° C. Conveniently, 1-4 moles of fluoride reagent per mole of compound of Formula XXVIII are utilized.

Reaction AA is also a three-step Vilsmeier-Haack reaction. In the exothermic initial step, the phosphorus oxyhalide of Formula XXIIB, preferably phosphorus oxychloride, is reacted with the 3-dialkylaminoacrolein of Formula XXIID, preferably 3-dimethylaminoacrolein, to form an iminium salt. The reaction temperature is suitably $-10°-25°$ C., preferably $-10°-5°$ C., and the reaction time is suitably 5-40 minutes, preferably 10-30 minutes. The reaction is carried out in a lower alkyl nitrile, preferably acetonitrile. Suitably, 1-5 moles, preferably 2-4 moles, of the phosphorus oxyhalide and the 3-dialkylaminoacrolein per mole of the indole of Formula XXIIA to be utilized in the second step are utilized. In the second step, the iminium salt of the first step is reacted with the indole of Formula XXIIA at, preferably, a temperature of 60°-100° C., more preferably 65°-85° C., for, preferably, 5-30 hours, more preferably 6-24 hours. The second step is carried out in the same solvent as the first step, both steps being carried out under anhydrous conditions and an inert atmosphere. In the third step, which is very exothermic, the adduct produced in the second step is decomposed with, for example, an aqueous base, preferably aqueous sodium or potassium hydroxide, preferably at $-15°-45°$ C., more preferably $-10°-25°$ C., in a manner similar to the third step of Reaction R. As in the case of Reaction R it is preferable to employ at least 4, more preferably 4-6, and most preferably 4, equivalents of the base per mole of the phosphorus oxyhalide.

Reactions BB, CC and DD are three-step reactions for converting the aldehyde of Formula XIX, XXIXB or XXIXC to the aldehyde of Formula XXIXB, XXIXC or XXIXD, respectively. In the first step, the compound of Formula XXIXA is reacted with a strong base such as phenyllithium, n-butyllithium, sodium hydride or potassium t-butoxide to form $(C_6H_5)_3P=CH-OCH_3$ in an anhydrous inert organic solvent, for example, tetrahydrofuran, diethyl ether or bis-(2-methoxyethyl) ether under an inert atmosphere at $-40°-0°$ C. for 1.5-4 hours. 1-1.03 moles of the strong base per mole of the compound of Formula XXIXA are conveniently utilized. The obtained $(C_6H_5)_3P=CH-OCH_3$ is reacted with the aldehyde of Formula XIX, XXIXB or XXIXC, as the case may be, in the second step (to obtain an enol ether) in an anhydrous inert organic solvent, conveniently the solvent utilized in the first step at $-50°-25°$ C., preferably $-20°-10°$ C., for 10-24 hours. Conveniently, 1-1.05 moles of $(C_6H_5)_3P=CH-OCH_3$ per mole of the aldehyde of Formula XIX, XXIXB or XXIXC are utilized. The enol ether product of the second step is hydrolyzed with an acid to obtain the aldehyde of the Formula XXIXB, XXIXC or XXIXD in the third step. Suitable acids include strong inorganic acids such as 70% aqueous perchloric acid or concentrated hydrochloric acid; a large molar excess of the acid is usually employed. The hydrolysis temperature is conveniently 0°-30° C., the hydrolysis time is conveniently 8-24 hours, and the solvent is conveniently a mixture of the excess aqueous acid and an inert organic solvent, e.g., diethyl ether or tetrahydrofuran.

In Reaction EE the lactone of Formula XCIX is hydrolyzed to the carboxylate salt of Formula C. It is convenient to react the lactone of Formula XCIX with 0.95-1, preferably 0.97-0.99, equivalent of an inorganic base of the formula $M_2^{\oplus}{}^{\ominus}OH$, preferably sodium hydroxide or potassium hydroxide, per mole of the lactone in an inert aqueous organic solvent, preferably a mixture of water and a lower alkanol, e.g., methanol or, preferably, ethanol, at, preferably, 20°-75° C., more preferably 20°-70° C., for, preferably, 1-6 hours, more preferably 1-4 hours, to obtain the carboxylate salt. As is evident to those in the art, a racemic cis lactone of Formula XCIX yields a racemic threo carboxylate salt of Formula C and a racemic trans lactone of Formula XCIX yields a racemic erythro carboxylate salt of Formula C. Likewise, if a single enantiomer of the lactone of Formula XCIX is utilized, a single enantiomer of the carboxylate salt of Formula C is obtained. For example, if a 4R,6S lactone is utilized, the product is the 3R,5S carboxylate salt.

Reaction FF is conveniently carried out by reacting the compound of Formula XCIXA with the lactone of Formula XCIX at 0°-70° C., preferably 0°-25° C. when $R_{7b}$ is primary alkyl, for 1-12 hours, preferably 1-3 hours when $R_{7b}$ is primary alkyl, in an anhydrous inert organic solvent, for example an ether such as tetrahydrofuran or, if a liquid, the alcohol of the formula $R_{7b}$—OH ($R_{7b}$ must be the same as in the compound of Formula XCIXA). Generally, at least 2, preferably 2-10, more preferably 2.05-2.5, moles of the compound of Formula XCIXA per mole of the lactone of Formula XCIX are employed. A racemic trans lactone of Formula XCIX yields a racemic erythro ester of Formula CA, a racemic cis lactone of Formula XCIX yields a racemic threo ester of Formula CA, and a chiral lactone of Formula XCIX yield a chiral ester of Formula CA, e.g., a 4R,6S lactone yields a 3R,5S ester.

Reactions GG and HH are conventional neutralizations. Typically, the carboxylic acid of Formula VIII or XIV is reacted with 0.95-1, preferably 0.96-0.98, equivalent of the base of the formula $M_2^{\oplus}{}^{\ominus}OH$ at 0°-25° C., preferably 20°-25° C., for 2-10 minutes, in an inert aqueous organic solvent, e.g., a mixture of water and a lower alkanol such as methanol or, preferably, ethanol.

Reactions AB-AG are carried out essentially as described in detail in U.S. Pat. 4,474,971 and Reactions AH and AI may be carried out as described in detail therein.

However, it is preferable to utilize 70% aqueous trifluoroacetic acid for Reaction AH, the cleavage of the trityl group. This reaction is preferably carried out in methylene chloride under an inert atmosphere utilizing 1-1.25, more preferably 1.1-1.2, moles of trifluoroacetic acid per mole of the compound of Formula CVII. The reaction is commenced at −80°-−50° C., preferably −55° C., the temperature is allowed to rise to −10°−0° C. over a period of 1 hour, and the reaction mixture is stirred at 0°-10° C. for 3 hours. It is preferred to terminate the reaction when only about 80% of the compound of Formula CVII has reacted in order to minimize byproduct formation.

It is preferred to carry out Reaction AI, the oxidation of the hydroxymethyl group to the formyl group, with pyridinium chlorochromate or, especially, chromium trioxide. When pyridinium chlorochromate is utilized, it is preferable to utilize 1.5-2.5, more preferably 2, moles thereof per mole of the compound of Formula CVIII, and the reaction is preferably carried out in an anhydrous halogenated lower alkane such as methylene chloride under an inert atmosphere, a suitable reaction temperature being 20°-30° C. and a suitable reaction time being 2.5-3.5 hours. When chromium trioxide is utilized, the reaction is carried out under Collins oxidation conditions. It is preferable to utilize 5-10, more preferably 8, moles of chromium trioxide (preferably complexed with pyridine, more preferably 2 moles of pyridine is complexed with one mole of chromium trioxide) per mole of the compound of Formula CVIII, and the reaction is run in an anhydrous halogenated lower alkane, such as methylene chloride, optionally containing some (e.g., 1 mole per mole of chromium trioxide) pyridine. A suitable reaction time is 2-3.5 hours, preferably 2 hours, and a suitable reaction temperature is 20°-30° C.

The preferred reaction conditions for Reactions AB-AI are:

AB: (1) sodium, methanol, 20° C., 15 minutes; (2) mercuric acetate, 25° C., 4 hours.

AC: sodium chloride, sodium borohydride, methanol+isopropanol, 20° C., 4 hours.

AD: triphenylmethyl chloride, pyridine, 35° C., 30 hours.

AE: (1) sodium hydride, tetrahydrofuran, 20° C., 3 hours; (2) 1-(2′,4′,6′-triisopropylphenylsulfonyl)imidazole, −30°→20° C., 2 hours.

AF: lithium aluminum hydride, methyl t-butyl ether, −10° C., 16 hours.

AG: t-butyldiphenylchlorosilane, imidazole, N,N-dimethylformamide, 20° C., 18 hours.

AH: 70% aqueous trifluoroacetic acid, methylene chloride, −55°→0°-10° C., 4 hours.

AI: chromium trioxide/pyridine, pyridine, methylene chloride, 20°-25° C., 2 hours.

The reaction conditions set forth above for Reactions AB-AG should be read in conjunction with Steps A-F of Example 1 of U.S. Pat. No. 4,474,971. Steps A-H of said Example 1 in columns 9-14 of said patent are hereby incorporated by reference.

Reaction AJ is a conventional oxidation of an alcohol to a ketone. Suitable oxidants and reaction conditions include those set forth above for Reaction AI.

Reaction AK is a conventional reduction of a ketone to an alcohol. Suitable reducing agents and conditions include those set forth above for Reactions B (non-stereoselective) and S, sodium borohydride being a preferred reducing agent. A mixture of the alcohols of Formulae CVI and CXI is produced. The mixture may be separated by conventional means, e.g., high pressure liquid chromatography or column chromatography, or the mixture may be utilized in the succeeding reactions (Reactions AG/AG′, AH/AH′, AJ/AJ′, W, X, etc.) to obtain a mixture of products, with the products separated by conventional techniques after any reaction, as may be desired or convenient.

Reactions AG′-AI′ may be carried out as described above and in U.S. Pat. No. 4,474,971 for Reactions AG-AI, respectively.

Most of the molar amounts (ratios) set forth above are merely exemplary and may be varied, as is evident to one of ordinary skill in the art. For example, in a reaction of two compounds one of which is readily available and one of which isn't, an excess of the readily available compound may be used to drive the reaction further towards completion (unless the use of an excess would increase the synthesis of an undesired compound).

Likewise, most of the temperature ranges and reaction times set forth above are merely exemplary, and it is within the ability of one of ordinary skill in the art to vary those that are not critical. As is well-known, the reaction time is often inversely related to the reaction temperature. Generally, each reaction is monitored by, for example, thin layer chromatography and is terminated when at least one starting material is no longer present, when it appears that no more of the desired product is being formed, etc.

Conventional work-up procedures have generally been omitted from the preceding discussion, e.g., the work-up procedure for Reaction FF involves the use of water.

An alternate process for the synthesis of certain compounds of Formulae VI and IXt wherein X is —CH═CH— involves the reaction of a compound of Formula XXIV with methyl 3,5-di-(t-butyldiphenylsilyloxy)-6-oxohexanoate (Compound 8 of Kapa, Tetrahedron Letters 25, 2435-2438 (1984)), the corresponding ethyl ester or another corresponding ester. The synthesis of said compound is disclosed therein, and the corresponding esters may be synthesized analogously. Also set forth therein are reaction conditions for reacting said deprotected aldehyde ester (Compound 8) with a Wittig reagent and for deprotecting the resulting olefin. The reaction conditions set forth in said publication as well as those set forth above for Reactions W and Z may be utilized to obtain racemic compounds of Formula IXt wherein X is —CH=CH— as well as racemic erythro compounds of Formula VI wherein X is —CH=CH— (if the desilylation reaction is carried out at 20°-25° C.). In each case, the product is a mixture of the (E) olefin and the (Z) olefin, with the former predominating (usually by a factor of ~8:1) which may be separated by conventional means.

The compounds of Formulae IVA, IVB, XA, XB, XIA, XVII, XVIIIA-XVIIIC, XIXA, XXI, XXIIA-XXIID, XXIXA and CI and the reagents not designated by a Roman numeral (e.g., 1-(2′,4′,6′-triisopropylphenylsulfonyl)imidazole) are known or, if unknown, may be synthesized by processes analogous to those described in the literature for similar known compounds. Compound CI is commercially available tri-O-acetyl-D-glucal. As for the compound of Formula XXV, one isomer is disclosed in Yang et al., Tetrahedron Letters 23, 4305–4308 (1982), another is disclosed in U.S. Pat. No. 4,474,971 and in Reaction Scheme IX and the synthesis of a third isomer is disclosed in Reaction Scheme IX. The isomer of Yang et al. and the isomer disclosed in U.S. Pat. No. 4,474,971 (and in Reaction Scheme IX) yield compounds of Formula XXIX having the 4R,6S configuration and, as a result of epimerization in Reaction X, compounds of said formula having the 4R,6R configuration. Compounds of Formula XXIX having the 4S,6R and 4S,6S configuration may be obtained from the other isomer whose synthesis is disclosed in Reaction Scheme IX.

Since optically pure compounds of Formula XXV are available, Reaction Scheme V may be utilized to obtain optically pure compounds of Formula XXIX which may be converted into optically pure compounds of Formulae VI, VII, XIII, etc. by Reaction Scheme VIII. Reactions D, J, K, etc. may be utilized to convert the obtained optically pure compounds of Formulae VI, VII, XIII, etc. to the corresponding compounds having another $R_7$ group.

The product of each reaction may, if desired, be purified by conventional techniques such as recrystallization (if a solid), column chromatography, preparative thin layer chromatography, gas chromatography (if sufficiently volatile), fractional distillation under high vacuum (if sufficiently volatile) or high pressure liquid chromatography. Often, however, the crude product of one reaction may be employed in the following reaction without purification.

As is evident to those in the art, each of the compounds of Formulae V, X and XI has a single center of asymmetry and, therefore, may be resolved into two optically active isomers. When a compound of Formula V or XI is converted into a compound of Formula VI or XII, respectively, an additional center of asymmetry is generated. Consequently, when a racemic compound of Formula V or XI is utilized, four stereoisomers (two pairs of diastereoisomers) of the resulting compound of Formula VI or XII are formed, whereas when an optically pure compound of Formula V or XI is utilized, two diastereoisomers of the compound of Formula VI or XII are formed.

The compounds of Formulae I, VI-IX and XII-XVI have two centers of asymmetry and, therefore, exist in four stereoisomeric forms. Except where the compound is formed from an optically pure precursor already having both chiral carbon atoms or where the reaction involves the use of a stereospecific reagent that gives an optically pure product, the compound is obtained as a mixture of two (if formed from an optically pure compound having one center of asymmetry) or four (if formed from a racemic compound having one center of asymmetry) stereoisomers.

The obtained mixtures of stereoisomers may be separated by conventional means. For example, diastereoisomers may be separated by fractional crystallization, column chromatography, preparative thin layer chromatography and high pressure liquid chromatography. Each compound of Formula IX may, for example, be separated by the high pressure liquid chromatography technique into its cis and trans components (Formulae IXc and IXt, respectively), each of which is a racemate that may be resolved into two optically active enantiomers.

Techniques for separating a racemate into its two optically active enantiomers are known. For example, a racemic compound having a carboxylic acid group may be reacted with an optically pure organic base having at least one center of asymmetry to form a mixture of diastereoisomeric salts that may be separated by fractional crystallization or it may be reacted with an optically pure alcohol having at least one center of asymmetry to form a mixture of diastereoisomeric esters which may be separated by conventional techniques such as those set forth above or below. Likewise, a racemic compound having a carboxylic acid, ester or lactone group may be reacted with an optically pure organic base, i.e., an amine, to form a mixture of diastereoisomeric amides that may be separated by conventional means, e.g., fractional crystallization, column chromatography and/or high pressure (performance) liquid chromatography (HPLC). For example, a racemic lactone of Formula IX or XV may be reacted with an excess of R-(+)-α-methylbenzylamine (or the corresponding S-(−) compound to form a mixture of two diastereoisomeric α-methylbenzylamides which may be separated by, for example, column chromatography on a silica gel column utilizing 15% acetone/methylene chloride as the eluant and/or by HPLC using a Partisil column with 9:1 hexane/isopropanol as the mobile phase. Often it is desirable to utilize both techniques, i.e., to partially separate the diastereoisomers by column chromatography and to purify each fraction by HPLC. Typically, the α-methylbenzylamides are synthesized by reacting the racemic lactone with a large molar excess of the amine at 20°-25° C. for 16–24 hours. The reaction is run neat with the excess amine serving as the solvent. After the reaction, the excess amine is removed by vacuum distillation at 25°-35° C. After separation, each chiral amide may be hydrolyzed to the corresponding, for example, sodium, salt by, for example, refluxing with 1.5-3, preferably 2-2.2, equivalents of a base such as sodium hydroxide for 5-25 hours in a mixture of water and ethanol. The resulting salts may be converted to the corresponding free acids, esters, lactones and other salts by conventional means such as Reactions D, E, J, K, EE, FF, GG and HH. On the other hand, a racemic compound having a hydroxy group may be esterified with an optically pure carboxylic acid having at least one center of asymmetry to form a mixture of diastereoisomeric esters or it may be reacted with an optically pure trisubstituted silyl halide, preferably (−)-α-naphthylphenylmethylchlorosilane (Sommer et al., J. Am. Chem. Soc. 80, 3271 (1958).), to form a mixture of two diastereoisomeric silyloxy compounds, which mixture may be separated by conventional techniques. For example, diastereoisomeric (—)-α-naphthylphenylmethylsilyl derivatives of a lactone of Formula IX, especially of Formula IXt, may be separated on a silica column (e.g., having an internal diameter of 1 cm. and a length of 25 cm.) having covalently bound L-phenylglycine utilizing, as the eluant, 1:1 (by volume) n-hexane/acetone. After separation, the optically pure salts, amides, esters or silyloxy compounds are reconverted to the corresponding carboxy group- or hydroxy group-containing compounds with retention of optical purity. For example, the process conditions disclosed for Reaction Z may be utilized to cleave (—)-α-naphthylphenylmethylsilyl and other silyl groups.

The compounds of Formula I (and each and every subscope thereof) wherein Z is a group of Formula II and $R_7$ is hydrogen may be converted into the corresponding compounds wherein $R_7$ is a cation, e.g., M, or $R_{7b}$ by conventional means, e.g., Reaction K, FF or GG (by treatment with a base having M as its cation, e.g., a base of the formula $M^{+q}(OH)_q$, wherein q is 1, 2 or 3). Likewise, those wherein Z is a group of Formula II and $R_7$ is any cation, e.g., M, may be converted into the corresponding compounds wherein $R_7$ is hydrogen or any other cation, e.g., M, by conventional means, e.g., Reactions D and J and ion exchange.

Since any compound of Formula I wherein Z is a group of Formula II wherein $R_7$ is a cation other than M may be converted into the corresponding compound wherein $R_7$ is hydrogen, M, $C_{1-3}$alkyl, n-butyl, i-butyl, t-butyl, etc., the compounds of Formula I wherein Z is a group of Formula II and $R_7$ is a pharmaceutically unacceptable cation are also within the scope of this invention since they are useful as intermediates. However, such compounds are not compounds of Formula I as utilized in this application, except where indicated to the contrary.

Besides having the utility set forth below, every compound of Formula I is useful as an intermediate in the synthesis of one or more other compounds of Formula I utilizing the reactions set forth above. Reactions C–E and J–L may be utilized to convert compounds of Formula I wherein Z is a group of Formula II into the corresponding compounds wherein Z is a group of Formula III and, as set forth above, into the corresponding compounds wherein Z is a group of Formula II having a different $R_7$ group and Reactions EE and FF may be utilized to convert compounds of Formula I wherein Z is a group of Formula III into corresponding compounds wherein Z is a group of Formula II.

Also within the scope of this invention are the intermediates of Formulae V, X, XI, XII, XX, XXIV, XXVI-XXVIII and XXIXB-XXIXD. The preferences for each variable are the same as those set forth for the compounds of Formula I, with the preferred groups of such compounds including those that correspond to Groups (i)-(xiii), (xxi)-(xxxii), (xxxix)-(liv) and (lxvii)-(cxlvii) (for Formulae V, X-XII, XX, XXIV and XXIXB-XXIXD) and Groups (xiv)-(xx), (xxxiii)-(xxxviii), (lv)-(lxvi) and (cxlix)-(cxcviii) (for Formulae XXVI-XXVIII) to the extent consistent therewith.

The entire specification of great-grand-parent application Ser. No. 06/443,668 (particularly pages 1-29, 34-36 and 49-66, especially pages 1-7) and pages 1-7 and 52-59 of great-grand-parent application Ser. No. 06/548,850 are hereby incorporated by reference as if completely set forth herein.

The compounds of Formula I are competitive inhibitors of 3-hydroxy-3-methylglutaryl coenzyme A (HMG-CoA) reductase, the rate limiting enzyme in cholesterol biosynthesis, and, therefore, they are inhibitors of cholesterol biosynthesis. Consequently, they are useful for lowering the blood cholesterol level in animals, e.g., mammals, especially larger primates, and, therefore, as hypolipoproteinemic and anti-atherosclerotic agents. The biological activity of the compounds of Formula I is demonstrated in the following three tests:

Test A. In Vitro Microsomal Assay of HMG-CoA Reductase Inhibition:

200 µl. aliquots (1.08–1.50 mg./ml.) of rat liver microsomal suspensions, freshly prepared from male Sprague-Dawley rats (150–225 g. body weight), in Buffer A with 10 mmol. dithiothreitol are incubated with 10 µl. of a solution of the test substance in dimethylacetamide and assayed for HMG-CoA reductase activity as described in Ackerman et al., J. Lipid Res. 18, 408–413 (1977). In the assay the microsomes are the source of the HMG-CoA reductase enzyme which catalyzes the reduction of HMG-CoA to mevalonate. The assay employs a chloroform extraction to separate the product, [$^{14}$C]mevalonolactone, formed by the HMG-CoA reductase reaction from the substrate, [$^{14}$C]HMG-CoA. [$^3$H]mevalonolactone is added as an internal reference. Inhibition of HMG-CoA reductase is calculated from the decrease in specific activity [$^{14}$C/$^3$H]mevalonate) of test groups compared to controls.

Test B. In Vitro Cell Culture Cholesterol Biosynthesis Screen

The cell culture is prepared as follows: Stock monolayer cultures of the Fu5AH rat hepatoma cell line (originally obtained from G. Rothblat; see Rothblat, Lipids 9, 526–535 (1974)) are routinely maintained in Eagle's Minimum Essential Medium (EMEM) supplemented with 10% fetal bovine serum (FBS) in 75 cm.$^2$ tissue culture flasks. For these studies, when the cultures reach confluence, they are removed by mild enzymatic treatment with 0.25% trypsin in Hanks' balanced salt solution (without calcium and magnesium). After centrifugation of the cell suspension and aspiration of the enzymatic solution, the cell pellet is resuspended in an appropriate volume of media for seeding into 60 mm. tissue culture dishes. The cultures are incubated at 37° C. in an atmosphere of high humidity and 5% carbon dioxide. When the cultures are confluent (approximately 5 days), they are ready for use. The culture media is aspirated from the dishes and replaced with 3 ml. of EMEM supplemented with 5 mg./ml. of delipidized serum protein (DLSP) prepared by the method of Rothblat et al., In Vitro 12, 554–557 (1976). Replacement of the FBS with DLSP has been shown to stimulate the incorporation of [$^{14}$C]acetate into sterol by removing the exogenous sterol supplied by the FBS, thereby requiring the cells to synthesize sterol. Enhanced 3-hydroxy-3-methylglutaryl Coenzyme A reductase (HMG-CoA reductase) activity is measurable in the cells in response to the lack of exogenous sterol. Following approximately 24 hours incubation at 37° C. in the DLSP supplemented media, the assay is initiated by the addition of 3 µCi of [$^{14}$C]acetate and the test substance solubilized in dimethylsulfoxide (DMSO) or distilled water. Solvent controls and compactin-treated controls are always prepared. Triplicate 60 mm. tissue culture dishes are run for each group. After 3 hours incubation at 37° C., the cultures are examined microscopically using an inverted phase contrast microscope. Notations are made of any morphological changes which may have occurred in the cultures. The media is aspirated and the cell layer is gently washed twice with 0.9% sodium chloride solution (saline). The cell layer is then harvested in 3 ml. of 0.9% saline by gentle scraping with a rubber policeman and transferred to a clean glass tube with Teflon lined cap. The dishes are rinsed with 3 ml. of 0.9% saline and rescraped, and the cells are combined with the first harvest. The tubes are centrifuged at 1500 r.p.m. for 10 minutes in an IEC PR-J centrifuge, and the supernatant is aspirated.

The cells are then extracted as follows: One ml. of 100% ethanol is added to the cell pellet followed by sonication for 10 seconds with a "LO" setting of 50 on a Bronwell Biosonik IV. One hundred $\mu$l. are taken for protein determination. One ml. of 15% potassium hydroxide (KOH) is added, and the samples are thoroughly vortexed. Saponification is accomplished by heating the ethanol-KOH treated samples at 60° C. for 60 minutes in a water bath. Following dilution of the samples with 2 ml. of distilled water, they are extracted three times with 7 ml. of petroleum ether. The petroleum ether extracts are then washed three times with 2 ml. of distilled water and finally taken to dryness under a stream of nitrogen.

The obtained samples are then analyzed by thin layer chromatography (TLC) as follows: Residues from the petroleum ether extraction are taken up in a small volume of hexane and spotted on silica gel 60 TLC plates (E. Merck). Development of the plates is carried out in a three phase solvent system consisting of 150 parts by volume hexane: 50 parts by volume diethyl ether: 5 parts by volume glacial acetic acid.

Visualization is accomplished in an iodine vapor chamber. The plates are divided into five sections such that each section contains the molecules having the following approximate Rf values: section 1- 0-0.4, section 2- 0.4-0.55, section 3- 0.55-0.7, section 4- 0.7-0.9 and section 5- 0.9-1.0. Section 2 contains the non-saponifiable sterols. The five sections of the TLC plates are scraped into scintillation vials. Blanks are also prepared from scrapings of chromatographed non-labelled standards. ACS® scintillation cocktail is added, and the radioactivity is determined in a liquid scintillation spectrometer. [$^{14}$C]hexadecane standards are used to determine counting efficiencies. The total protein content of the samples is determined employing the Bio-Rad Protein Assay System.

The results are reported as disintegrations per minute per mg. protein (d.p.m./mg. protein) for each of the five TLC sections. Mean d.p.m./mg. protein±standard error of the mean are calculated, and drug treated means are compared for percentage change (%$\Delta$) and statistical significance with solvent control means. TLC section 2 data is taken as a measure of HMG-CoA reductase activity inhibition.

Test C. In Vivo Cholesterol Biosynthesis Inhibition Test

In vivo studies utilize male Wistar Royal Hart rats weighing 150±20 g. which have been kept for 7-10 days on an altered light cycle (6:30 A.M.-6:30 P.M. dark) housed two per cage and fed powdered Purina Rat Chow and water ad libitum. Three hours before the diurnal maximum of cholesterol synthesis at mid-dark, the rats are administered the test substances dissolved or as a suspension in 0.5% carboxymethylcellulose in a volume of 1 ml./100 g. body weight. Controls receive vehicle alone. One hour after receiving the test substance, the rats are injected intraperitoneally with about 25 $\mu$Ci/100 g. body weight of sodium [1-$^{14}$C]acetate 1-3 mCi/mmol. Two hours after mid-dark, blood samples are obtained under sodium hexobarbitol anesthesia and the serum separated by centrifugation.

Serum samples are saponified and neutralized, and the 3$\beta$-hydroxy sterols are precipitated with digitonin basically as described by Sperry et al., J. Biol. Chem. 187,97 (1950). The [$^{14}$C]digitonides are then counted by liquid scintillation spectrometry. After correcting for efficiencies, the results are calculated in nCi (nanocuries) of sterol formed per 100 ml. of serum. Inhibition of sterol synthesis is calculated from the reduction in the nCi of sterols formed from test groups compared to controls.

In this test, the test substances (compounds of Formula I) are administered at doses of 0.005-200 mg./kg. body weight.

The following results were obtained:

| Test A: | Example 1 | $IC_{50}$ = 1.7 $\mu$molar |
|---|---|---|
| | Example 3 | $IC_{50}$ = 1.66 $\mu$molar |
| | Example 4 (a) | $IC_{50}$ = 3.0 $\mu$molar |
| | Example 8 | $IC_{50}$ = 6 nanomolar |
| | Example 9 | $IC_{50}$ = 0.12 $\mu$molar |
| | Example 10 | $IC_{50}$ = 1.7 $\mu$molar |
| | Example 12 | $IC_{50}$ = 9.1 $\mu$molar |
| | Example 14D | $IC_{50}$ = 5 nanomolar |
| | Example 23 | $IC_{50}$ = 0.09 $\mu$molar |
| | Example 43 | $IC_{50}$ = 9.6 $\mu$molar |
| | Example 54 | $IC_{50}$ = 464 $\mu$molar |
| | Example 60 | $IC_{50}$ = 0.12 $\mu$molar |
| | Example 64 | $IC_{50}$ = 0.012 $\mu$molar |
| | Example 75 | $IC_{50}$ = 5.4 nanomolar |
| | Example 89 | $IC_{50}$ = 9.3 $\mu$molar |
| | Example 102 | $IC_{50}$ > 1000 $\mu$molar |
| | Example 113 | $IC_{50}$ = 0.03 $\mu$molar |
| | Example 132 | $IC_{50}$ = 1.62 $\mu$molar |
| | Example 142 | $IC_{50}$ = 1.3 $\mu$molar |
| | Compactin | $IC_{50}$ = 0.77 $\mu$molar |
| | Mevinolin | $IC_{50}$ = 0.14 $\mu$molar |
| Test B: | Example 1 | $IC_{50}$ = 0.8 $\mu$molar |
| | Example 3 | $IC_{50}$ = 0.8 $\mu$molar |
| | Example 4 (a) | $IC_{50}$ = 0.62 $\mu$molar |
| | Example 8 | $IC_{50}$ = 0.05 $\mu$molar |
| | Example 9 | $IC_{50}$ = 0.22 $\mu$molar |
| | Example 10 | $IC_{50}$ = 0.42 $\mu$molar |
| | Example 12 | −16% at 1 $\mu$molar |
| | Example 21 | $IC_{50}$ = 0.2 $\mu$molar |
| | Example 23 | $IC_{50}$ = 0.6 $\mu$molar |
| | Example 43 | $IC_{50}$ = 0.74 $\mu$molar |
| | Example 64 | $IC_{50}$ = 0.03 $\mu$molar |
| | Example 111 | $IC_{50}$ = 0.19 $\mu$molar |
| | Example 132 | −71% at 10 $\mu$molar |
| | Example 142 | $IC_{50}$ = 1.5 $\mu$molar |
| | Compactin | $IC_{50}$ = 0.06 $\mu$molar |

$IC_{50}$ is the concentration of the test substance in the assay system calculated to produce a 50% inhibition of HMG-CoA reductase activity (Test A) or sterol biosynthesis (Test B).

| Test C: | Example 1 | $ED_{50}$ = 6.2 mg./kg. |
|---|---|---|
| | Example 3 | $ED_{50}$ > 10 mg./kg. |
| | Example 4 (a) | $ED_{50}$ = 7.0 mg./kg. |
| | Example 8 | $ED_{50}$ = 0.09 mg./kg. |
| | Example 9 | $ED_{50}$ = 1.4 mg./kg. |
| | Example 10 | −47% at 4 mg./kg. |
| | Example 14D | $ED_{50}$ = 0.16 mg./kg. |

| -continued | |
|---|---|
| Example 21 | $ED_{50}$ = 12.1 mg./kg. |
| Example 60 | $ED_{50}$ = 0.87 mg./kg. |
| Example 64 | $ED_{50}$ = 0.66 mg./kg. |
| Example 113 | $ED_{50}$ = 0.51 mg./kg. |
| Example 132 | −35% at 10 mg./kg. |
| Example 142 | $ED_{50}$ = 6.1 mg./kg. |
| Compactin | $ED_{50}$ = 3.5 mg./kg. |
| Mevinolin | $ED_{50}$ = 0.41 mg./kg. |

As set forth above, the compounds of Formula I (including each and every subgroup thereof set forth in the specification and/or the claims) inhibit cholesterol biosynthesis and are useful for lowering the blood cholesterol level in animals, particularly mammals and more particularly larger primates, and, therefore, as hypolipoproteinemic and anti-atherosclerotic agents.

The compounds of Formula I may be formulated into conventional pharmaceutical compositions and administered by conventional modes of administration. The compounds of each and every subgroup thereof in the specification and/or claims may likewise be formulated into conventional pharmaceutical compositions.

The compounds of Formula I may be combined with one or more pharmaceutically acceptable carriers and, optionally, one or more other conventional pharmaceutical adjuvants and administered orally in the form of tablets, dispersible powders, granules, capsules, elixirs, suspensions and the like or parenterally in the form of sterile injectable solutions or suspensions. The compositions may be prepared by conventional means. The preferred pharmaceutical compositions from the standpoint of ease of preparation and administration are solid compositions, particularly tablets and capsules.

The precise dosage of the compound of Formula I to be employed for inhibiting cholesterol biosynthesis depends upon several factors including the host, the nature and the severity of the condition being treated, the mode of administration and the particular compound employed. However, in general, satisfactory inhibition or reduction of cholesterol biosynthesis (i.e., satisfactory reduction of the blood cholesterol level and satisfactory treatment of hyperlipoproteinemia and atherosclerosis) is achieved when a compound of Formula I is administered orally at a daily dosage of 0.01-100, preferably 0.1-25, mg./kg. body weight or, for most larger primates, a daily dosage of 0.1-2000 mg., generally 0.1-300 mg. for the preferred compounds. For the compound of Example 8, the oral daily dosage is indicated to be 0.01-10 mg./kg. body weight, preferably 0.1-5 mg./kg. body weight, or, for most larger primates, it is indicated to be 0.1-140 mg. and preferably 5-20 mg., and for the compound of Example 14D the oral daily dosage is indicated to be approximately twice that of the compound of Example 8.

The daily dosage is usually divided into two to four equal portions or administered in sustained release form. A typical oral dosage of the compound of Example 8 is indicated to be 1 mg. three times per day and a typical oral dosage of the compound of Example 14D is indicated to be 2 mg. three times per day. Usually, a small dosage is administered initially, and the dosage is gradually increased until the optimal dosage for the host under treatment is determined. For administration by injection, a dosage somewhat lower than would be used for oral administration of the same compound to the same host having the same condition is usually employed. However, the above dosages are also typically used for i.v. administration.

A typical dosage unit for oral administration may contain 0.5 to 500 mg. of a compound of Formula I. Preferred dosage units contain 0.5 to 50 mg., especially 0.5 to 25 mg., of a compound of Formula I.

The compounds of Formula I (including those of each and every subgroup thereof) may be formulated into such pharmaceutical compositions containing an amount of the active substance that is effective for inhibiting cholesterol biosynthesis, such compositions in unit dosage form and such compositions comprising a solid pharmaceutically acceptable carrier.

Representative formulations preparable by conventional techniques for encapsulation in a hard gelatin capsule are:

| | |
|---|---|
| A. Compound of Formula I, e.g., the compound of Example 4(a) | 10 mg. |
| Lactose (spray-dried) | 90 mg. |
| B. Compound of Formula I, e.g., the compound of Example 1 | 25 mg. |
| Peanut oil | to 0.25 ml. |
| C. Compound of Formula I, e.g., the compound of Example 8 | 1 mg. |
| Corn starch | 248 mg. |
| Magnesium stearate | 1 mg. |
| D. Compound of Formula I, e.g., the compound of Example 14D | 10 mg. |
| Corn starch | 239 mg. |
| Magnesium stearate | 1 mg. |
| E. Compound of Formula I, e.g., the compound of Example 8 | 10 mg. |
| Lactose N.F. | 135.15 mg. |
| Pregelatinized starch N.F. | 63 mg. |
| Colloidal silicon dioxide N.F. | 0.6 mg. |
| Magnesium stearate N.F. | 0.75 mg. |
| Identical formulations containing 1 mg. of the active ingredient and 144.15 mg. of Lactose N.F. or 5 mg. of the active ingredient and 140.15 mg. of Lactose N.F. may also be prepared. | |

Representative formulations suitable for preparing tablets by conventional means are:

| | |
|---|---|
| A. Compound of Formula I, e.g., the compound of Example 3 | 25 mg. |
| Gum tragacanth | 5 mg. |
| Powdered lactose | 98.5 mg. |
| Corn starch | 12.5 mg. |
| Talc | 7.5 mg. |
| Magnesium stearate | 1.5 mg. |
| B. Compound of Formula I, e.g., the compound of Example 8 | 2 mg. |
| Polyvinylpyrrolidone USP | 5 mg. |
| Powdered lactose | 82 mg. |
| Corn starch | 10 mg. |
| Magnesium stearate | 1 mg. |

The following examples show representative compounds encompassed by this invention and their synthesis. However, it should be understood that they are for purposes of illustration only.

EXAMPLE 1

Methyl (E)-3,5-dihydroxy-7-[3'-(4''-fluorophenyl)-1'-methylindol-2'-yl]hept-6-enoate

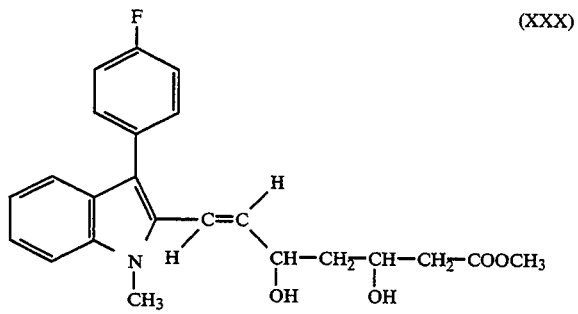

(XXX)

STEP 1 (REACTION Q)

Ethyl 3-(4'-fluorophenyl)-1-methylindole-2-carboxylate

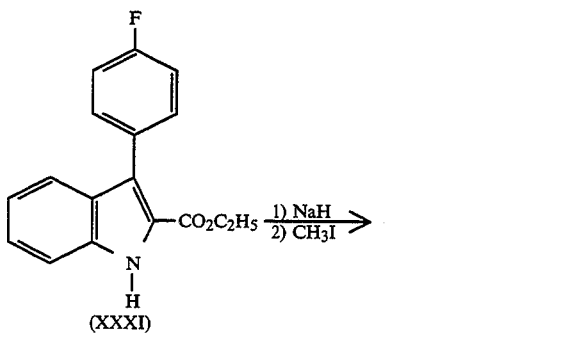

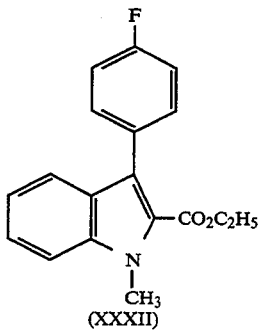

To a solution of 8.0 g. (28 mmol.) of ethyl 3-(4'-fluorophenyl)indole-2-carboxylate in 30 ml. of dry dimethylacetamide stirred under nitrogen at −10° C., 1.6 g. (33 mmol.) of sodium hydride is added. The reaction mixture is stirred at −10° C. under nitrogen for 45 min., 4.8 g. (32 mmol.) of methyl iodide is added at −10° C., and the reaction mixture is allowed to warm to room temperature and stirred under nitrogen at room temperature for 2 hrs. The reaction mixture is poured into 400 ml. of ice/water, neutralized with 4 ml. of 2N. hydrochloric acid and extracted several times with diethyl ether. The diethyl ether extracts are combined, washed with water, washed with saturated sodium chloride solution, dried over anhydrous magnesium sulfate, filtered and evaporated at reduced pressure. The residue is purified by column chromatography utilizing a silica gel column and chloroform as the eluant. The fractions containing the product are combined and evaporated at reduced pressure, and the residue is crystallized from n-hexane/petroleum ether to obtain the product (7.6 g. (91%)), m.p. 61°–62° C.

STEP 2 (REACTION M)

3-(4'-Fluorophenyl)-2-hydroxymethyl-1-methylindole

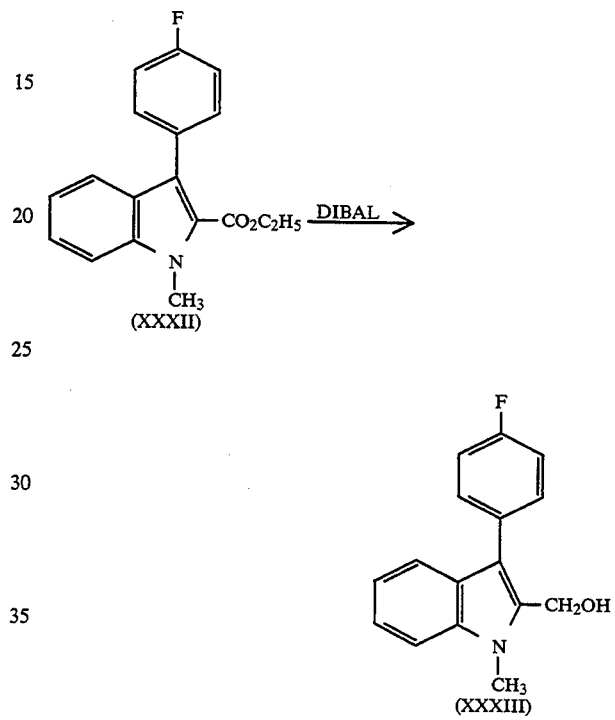

To a solution of 20.0 g. (67 mmol.) of Compound XXXII in 500 ml. of dry tetrahydrofuran stirred at −78° C. under nitrogen, 80 ml. of 25% (by weight) diisobutylaluminum hydride/toluene is added, and the reaction mixture is stirred at −78° C. under nitrogen for 4 hrs. The reaction mixture is allowed to warm to −10° C., an additional 30 ml. of 25% (by weight) diisobutylaluminum hydride/toluene is added, the reaction mixture is stirred at 0° C. under nitrogen for an additional 3 hrs., a further 30 ml. of 25% (by weight) diisobutylaluminum hydride/toluene is added, and the reaction mixture is stirred at 0° C. under nitrogen for a further 1 hr. The reaction mixture is treated with saturated ammonium chloride solution and filtered, and the organic layer is separated, dried over anhydrous magnesium sulfate, filtered and evaporated at reduced pressure. The residue is triturated with n-hexane to obtain the product (17.0 g. (100%)), m.p. 99°–104° C.

STEP 3 (REACTION N)

3-(4'-Fluorophenyl)-1-methylindole-2-carboxaldehyde

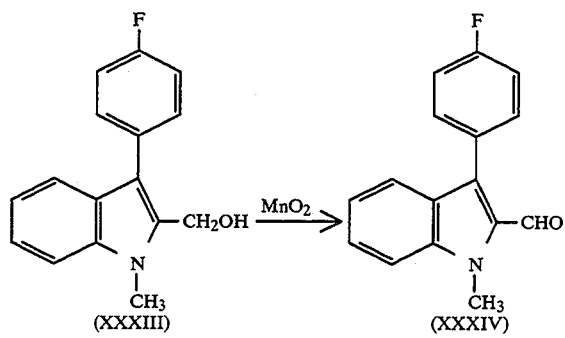

A mixture of 17.0 g. (67 mmol.) of Compound XXXIII, 90.0 g. (1.03 mol.) of manganese dioxide and 1.2 l. of anhydrous diethyl ether is stirred at room temperature under nitrogen for 14 hrs. The reaction mixture is filtered, and the diethyl ether is evaporated at reduced pressure. The residue is flash chromatographed on a silica gel column using methylene chloride as the eluant, the fractions containing the product are combined and evaporated at reduced pressure, and the residue is triturated with n-pentane to obtain the product (12.2 g. (72%)), m.p. 75°–79° C.

STEP 4 (REACTION O)

(E)-3-[3'-(4''-Fluorophenyl)-1'-methylindol-2'-yl]propenaldehyde

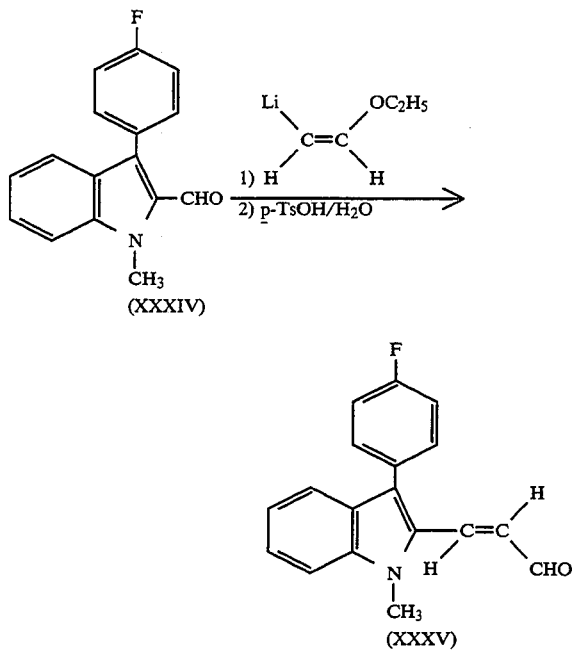

25 ml. of 1.7M. n-butyllithium/n-hexane (42 mmol.) is added dropwise to a solution of 14.5 g. (40 mmol.) of tri-n-butylstannylvinylethoxide in 600 ml. of dry tetrahydrofuran stirred at −78° C. under nitrogen, stirring is maintained for 2 hrs. under the same conditions, and 9.0 g. (35.6 mmol.) of Compound XXXIV, dissolved in 60 ml. of dry tetrahydrofuran, is added rapidly dropwise. The reaction mixture is stirred at −78° C. under nitrogen for 3.5 hrs., quenched with 60 ml. of saturated ammonium chloride solution and extracted several times with diethyl ether. The diethyl ether extracts are combined, washed with water, washed with saturated sodium chloride solution, dried over anhydrous magnesium sulfate, filtered and evaporated at reduced pressure. The residue is partitioned between n-hexane and acetonitrile (to remove the organotin compounds), and the acetonitrile layer is evaporated at reduced pressure to obtain an oil. The oil is dissolved in 300 ml. of tetrahydrofuran, 50 ml. of water and 30 mg. of p-toluenesulfonic acid monohydrate are added, and the reaction mixture is stirred for 2 hrs. at room temperature and then extracted several times with diethyl ether. The diethyl ether extracts are combined, washed with water, washed with saturated sodium chloride solution, dried over anhydrous magnesium sulfate, filtered and evaporated to dryness at reduced pressure. The residue is triturated with n-hexane/diethyl ether to obtain the product (5.3 g.), m.p. 110°–112° C. A subsequent batch melted at 115°–118° C.

N.M.R. (CDCl$_3$, 3.97 (3H singlet) 90 MHz. 6.55 (1H doublet of a doublet) 7.10–7.70 (9H multiplet) 9.56 (1H doublet)

STEP 5 (REACTION A)

Methyl (E)-7-[3'-(4''-fluorophenyl) 1'-methylindol-2'-yl]-5-hydroxy-3-oxohept-6-enoate

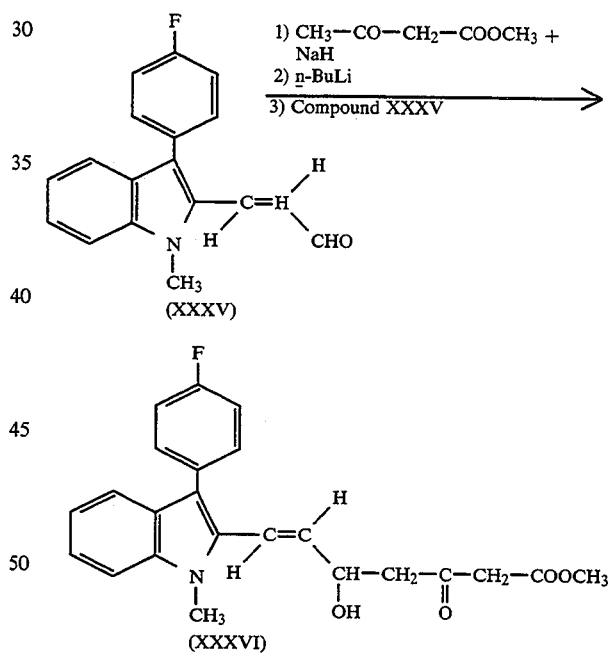

3.5 ml. (32.4 mmol.) of methyl acetoacetate is added dropwise to a suspension of 1.6 g. of 50% (by weight) sodium hydride (33.3 mmol.) in 400 ml. of dry tetrahydrofuran stirred at −15° C. under nitrogen. The reaction mixture is stirred at −15° C. under nitrogen for 20 min., 19 ml. of 1.7M. n-butyllithium/n-hexane (31.9 mmol.) is added, the reaction mixture is stirred at −15° C. under nitrogen for 20 minutes, a solution of 5.3 g. (19 mmol.) of Compound XXXV in 100 ml. of dry tetrahydrofuran is added, and the reaction mixture is stirred at −15° C. under nitrogen for 30 min. The reaction mixture is quenched with dilute hydrochloric acid and extracted several times with diethyl ether. The diethyl ether extracts are combined, washed with water, washed with saturated sodium chloride solution, dried over anhydrous magnesium sulfate, filtered and evaporated to dryness at reduced pressure. The residue is triturated with n-pentane (to remove excess methyl acetoacetate) to obtain the crude product as an oil.

The product is a racemate that may be resolved into its d and l components.

STEP 6 (REACTION B)

Methyl (E)-3,5-dihydroxy-7-[3'-(4''-fluorophenyl)-1'-methylindol-2'-yl]hept-6-enoate

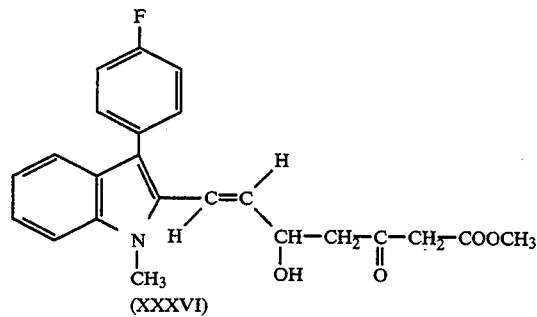
(XXXVI)

↓ t-BuNH₂.BH₃

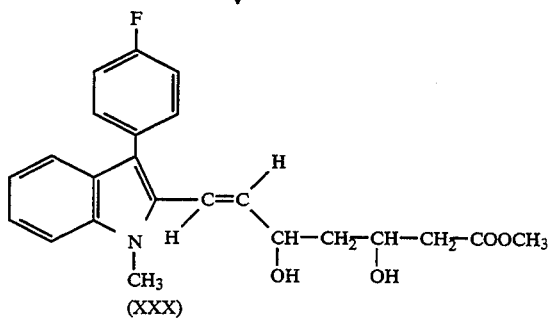
(XXX)

2.0 g. of borane-t-butylamine complex is added to a solution of 8.0 g. (20.2 mmol.?) of crude racemic Compound XXXVI in 200 ml. of absolute ethanol stirred at 0° C. under nitrogen. The reaction mixture is stirred at 0° C. under nitrogen for 3 hrs., and saturated sodium chloride solution is added. The reaction mixture is acidified with dilute hydrochloric acid and extracted several times with diethyl ether. The diethyl ether extracts are combined, washed with water, washed with saturated sodium chloride solution, dried over anhydrous magnesium sulfate, filtered and evaporated to dryness at reduced pressure. The obtained oil is purified by flash chromatography using a silica gel column and 1:1 ethyl acetate/chloroform as the eluant. The product, a mixture of four stereoisomers, is obtained as a yellow oil (6.1 g.).

N.M.R. (CDCl₃): 1.5–1.9 (2H multiplet) 2.4–2.6 (2H multiplet) 2.8–3.4 (2H broad peak, exchangeable) 3.7 (3H singlet) 3.8 (3H singlet) 4.26 (1H multiplet) 4.55 (1H multiplet) 5.85–6.1 (1H multiplet) 6.7 (1H two doublets) 7.05–7.55 (8H multiplet)

I.R. (CHCl₃): 1710 and 1210 cm.⁻¹ and others

The obtained mixture of stereoisomers may be separated by conventional means into two racemic mixtures each of which may be resolved into two optically pure enantiomers. The four isomers may be designated as the 3R,5R, 3S,5S, 3R,5S and 3S,5R isomers. Preferred are the 3R,5R and 3R,5S isomers and the racemate of which each is a constituent, viz., the 3R,5R-3S,5S and the 3R,5S-3S,5R racemate.

EXAMPLE 2

(E)-3,5-Dihydroxy-7-[3'-(4''-fluorophenyl)-1'-methylindol-2'-yl]hept-6-enoic acid (Reactions C and D)

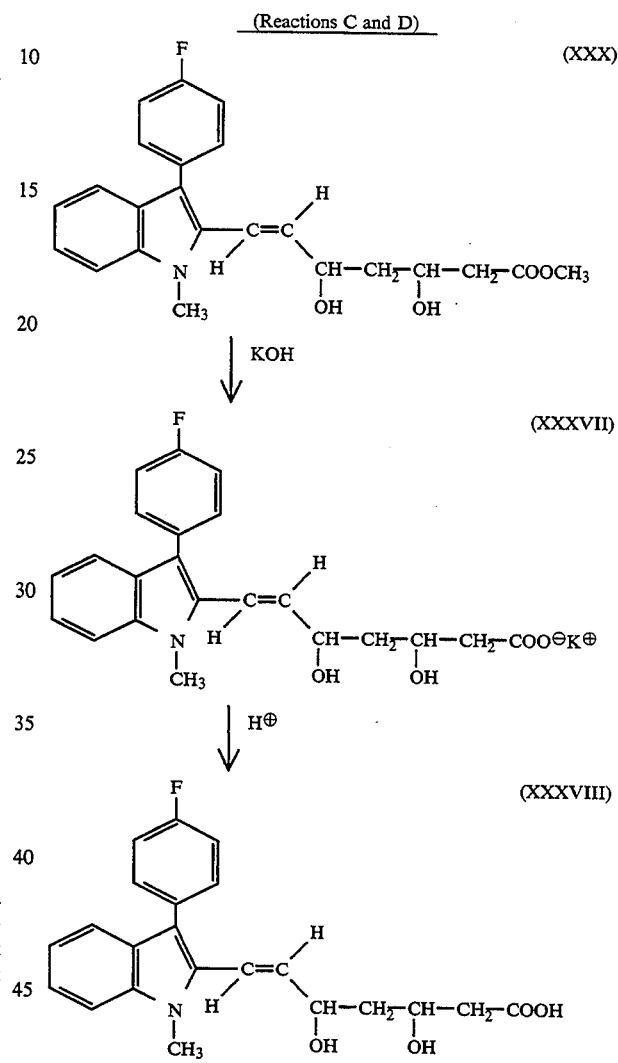

2.8 ml. of 1N. aqueous potassium hydroxide (2.8 mmol.) is added to a solution of 1.1 g. (2.77 mmol.) of Compound XXX in 100 ml. of 95% aqueous methanol stirred at room temperature, and the reaction mixture is stirred at room temperature for 3 hrs. The solvent is evaporated at reduced pressure, the residue (crude Compound XXXVII, a mixture of four stereoisomers) is dissolved in water, and the aqueous solution is extracted with diethyl ether. The aqueous phase is acidified with dilute hydrochloric acid (pH 6.0) and extracted several times with diethyl ether. The diethyl ether extracts are combined, washed with water, washed with saturated sodium chloride solution, dried over anhydrous magnesium sulfate, filtered and evaporated at reduced pressure to give the crude product as a yellow oil. It is a mixture of four stereoisomers.

If desired, Compound XXXVII or Compound XXXVIII may be separated into two racemic mixtures each of which may be resolved into two optically pure enantiomers. The four stereoisomers may be designated as the 3R,5R, 3S,5S, 3R,5S and 3S,5R isomers.

Preferred are the 3R,5R and 3R,5S isomers and the racemate of which each is a constituent, viz., the 3R,5R-3S,5S racemate and the 3R,5S-3S,5R racemate.

EXAMPLE 3

(E)-6-[2'-[3"-(4'''-Fluorophenyl)-1"-methylindol-2"-yl]ethenyl]-4-hydroxy-3,4,5,6-tetrahydro-2H-pyran-2-one

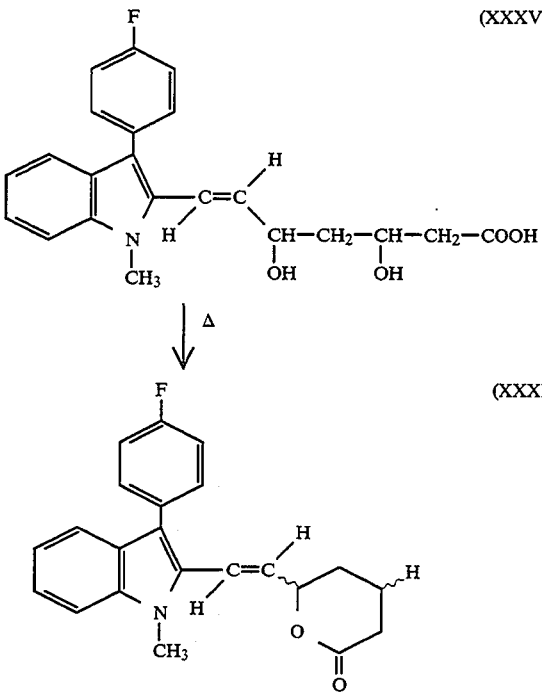

A solution of 1.1 g. (2.87 mmol.?) of crude Compound XXXVIII in 50 ml. of dry benzene is refluxed for 8 hrs. The solvent is evaporated at reduced pressure, and the residue is flash chromatographed on a silica gel column utilizing 19:1 chloroform/methanol as the eluant to obtain the product as a mixture of four diastereoisomers (two cis and two trans) (640 mg.).

| N.M.R. (CDCl₃): | 1.6–3.0 (5H multiplet) |
| --- | --- |
| | 3.82 (3H two singlets) |
| | 4.39 (1H multiplet) |
| | 4.78 ⎫ (1H two ⎰ cis isomer, C-6 H) |
| | 5.30 ⎭ singlets) ⎱ (trans isomer, C-6 H) |
| | 5.82–6.0 (1H two overlapping doublets of a doublet) |
| | 6.69–6.81 (1H two doublets) |
| | 7.05–7.6 (8H multiplet) |
| I.R. (CHCl₃): | 3600 (m), 3400 (broad), 3000 (s), 2960 (m), 2930 (m), 1736 (s) and 1220 (s) cm.⁻¹ and others |

I.R. (CHCl₃): 3600 (m), 3400 (broad), 3000 (s), 2960 (m), 2930 (m), 1736 (s) and 1220 (s) cm.$^{-1}$ and others

EXAMPLES 4(a) and 4(b)

(E)-Trans-6-[2'-[3"-(4'''-fluorophenyl)-1"-methylindol-2"-yl]ethenyl]-4-hydroxy-3,4,5,6-tetrahydro-2H-pyran-2-one and the corresponding cis lactone

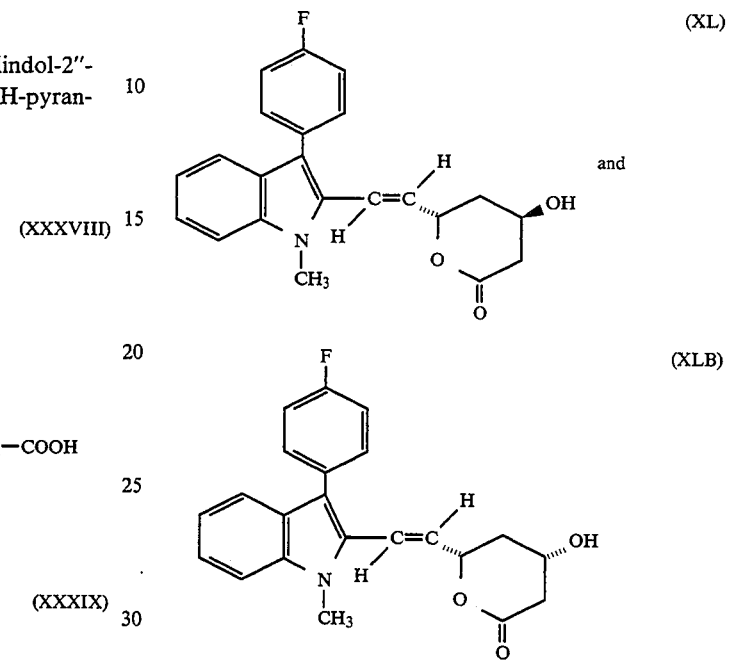

(a) The mixture of isomers obtained in Example 3 is separated by high pressure liquid chromatography using a silica gel column and, as the solvent, 7:2:1 methyl t-butyl ether/n-hexane/acetone to obtain the racemic trans lactone, m.p. 147°–150° C. A subsequent batch melted at 150°–154° C.

N.M.R. (CDCl₃): 1.7–2.1 (3H multiplet) 2.55–2.85 (2H multiplet) 3.8 (3H singlet) 4.38 (1H multiplet) 5.30 (1H multiplet) 5.9 (1H doublet of a doublet) 6.72 (1H doublet of a doublet) 7.05–7.6 (8H multiplet)

U.V.: $\lambda_{max}$=278 mμ 315 mμ

I.R. (CHCl₃): 3600 (m), 3010 (s), 2910 (broad), 1710 (s) and 1220 (s) cm.$^{-1}$ and others The obtained racemate may be resolved by conventional means into two optically pure enantiomers, the 4R,6S and 4S,6R isomers by, for example, (i) reacting with (−)-α-naphthylphenylmethylchlorosilane, (ii) separating the obtained diastereoisomeric silyloxy compounds and (iii) cleaving the silyl groups with tetra-n-butylammonium fluoride in a mixture of acetic acid and tetrahydrofuran, as set forth above. The amorphous solid 4R,6S enantiomer has an $[\alpha]_D^{25}$= −18.5° (CHCl₃, c=0.2 g.). The 4S,6R enantiomer was also an amorphous solid. $[\alpha]_D^{25}$= +11.36° (CHCl₃, c=0.22 g.)

(b) The racemic cis lactone may also be isolated from the silica gel column, m.p. 48°–62° C. (dec.). It too may be resolved by conventional means into two optically pure enantiomers. The two stereoisomers may be designated at the 4R,6R and 4S,6S isomers, the former being preferred.

N.M.R. (CDCl₃): 1.62–1.78 (1H multiplet) 1.94 (1H doublet) 2.35–2.4 (1H multiplet) 2.52 (1H doublet of a doublet) 2.98 (1H doublet of a doublet) 3.87 (3H singlet) 4.3 (1H multiplet) 4.8 (1H multiplet) 5.95 (1H doublet of a doublet) 6.77 (1H doublet) 7.1–7.6 (8H multiplet)

EXAMPLE 5

Methyl (±)-erythro-(E)-3,5-dihydroxy-7-[3'-(4''-fluorophenyl)-1'-(1''-methylethyl)indol-2'-yl]hept-6-enoate

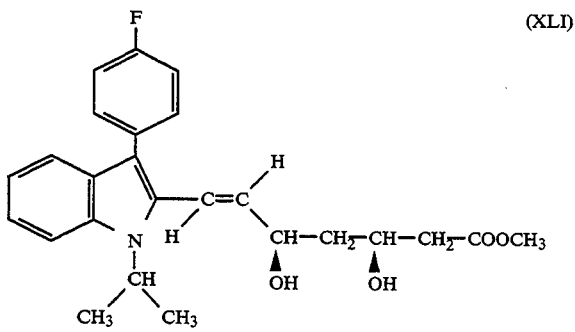

(XLI)

STEP 1
4-Chloroacetyl-1-fluorobenzene

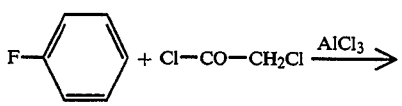

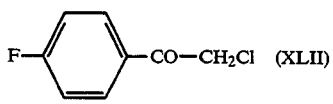

(XLII)

164 ml. (235.1 g., 2.04 moles) of chloroacetyl chloride is added over a 50 min. period to a mixture of 400 ml. (410 g., 4.22 moles) of fluorobenzene and 300 g. (2.25 moles) of anhydrous aluminum chloride stirred at 75° C. under nitrogen. The reaction mixture is stirred at 80° C. under nitrogen for 1 hour, cooled to 50° C., 500 ml. of fluorobenzene is added, and the reaction mixture is cooled to 0° C. and gradually (over a 30 min. period) siphoned into 1 l. of 6N. hydrochloric acid stirred at 0° C. (The temperature of the aqueous acid is maintained at or below 25° C. throughout the addition.) The quenched, acidified reaction mixture is stirred for 15 min., and the aqueous phase is separated and extracted with 350 ml. of fluorobenzene. The two organic phases are combined and washed twice with 500 ml. portions of 3N. hydrochloric acid and once with 500 ml. of water. The fluorobenzene is distilled at 30 mm. Hg. and 60° C. and, upon cooling, the obtained oily residue solidifies. The crude solid product need not be purified.

STEP 2
N-(4-Fluorobenzoylmethyl)-N-(1-methylethyl)aniline

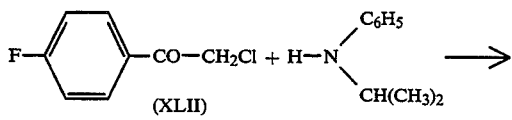

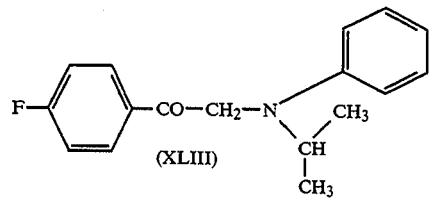

(XLIII)

562.9 g. (4.08 moles) of N-isopropylaniline is rapidly added to a solution of the crude product of Step 1 in 500 ml. of dimethylformamide stirred at 50° C. under nitrogen. The reaction mixture is stirred at 100° C. under nitrogen for 10 hours and allowed to cool to room temperature overnight. The reaction mixture is heated to 60° C., 2 l of water is added, and the mixture is cooled to 10° C. The obtained solids are collected, washed twice with 500 ml. portions of water and dissolved in 550 ml. of 95% ethanol at 75° C. The solution is cooled to 0° C., and the obtained solids are collected, washed three times with 100 ml. portions of 95% ethanol and vacuum dried at 35°–40° C. for 4 hours to obtain the 95.3% pure yellow product (466 g. (80.2% (two steps))), m.p. 78°–81° C.

STEP 3
3-(4'-Fluorophenyl)-1-(1'-methylethyl)indole

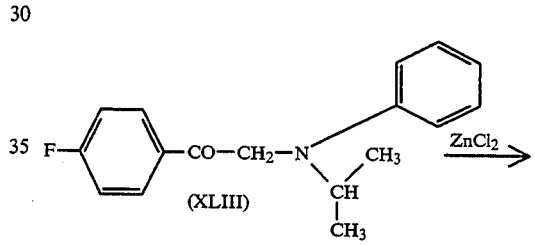

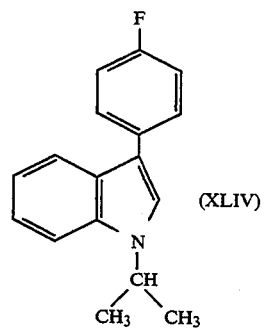

(XLIV)

954 g. (7.0 moles) of anhydrous zinc chloride is added portionwise to 1.27 l. of absolute ethanol stirred at room temperature under nitrogen. The addition is exothermic. To the resulting hot (70° C.) solution, 271.3 g. (1.0 mole) of Compound XLIII is added, and the reaction mixture is stirred at 100°–103° C. under nitrogen for 3 hours and cooled to 25° C. 1.5 l. of 1N. hydrochloric acid is added, followed by 1 l. of methylene chloride. The resulting two-phase system is stirred for 5 min., the organic phase is separated, and the aqueous phase is washed twice with 250 ml. portions of methylene chloride. The three methylene chloride phases are combined, the volume is reduced by about 50% by partial evaporation of the methylene chloride at 140 mm. Hg. and 40° C., and 1 l. of 95% ethanol is added. The reaction mixture is distilled at atmospheric pressure until a vapor temperature of 75° C. (pot temperature of 77° C.) is reached and cooled to 0° C. The obtained solids are collected, washed three times with 100 ml. portions of cold ethanol and vacuum dried overnight at room temperature to obtain the 99.9% pure product as a white powder (195 g. (81% corrected for purity of starting material)), m.p. 94.5°–95.5° C.

STEP 4 (REACTION AA)

(E)-3-[3'-(4''-Fluorophenyl)-1'-(1''-methylethyl)indol-2'-yl]-prop-2-enal

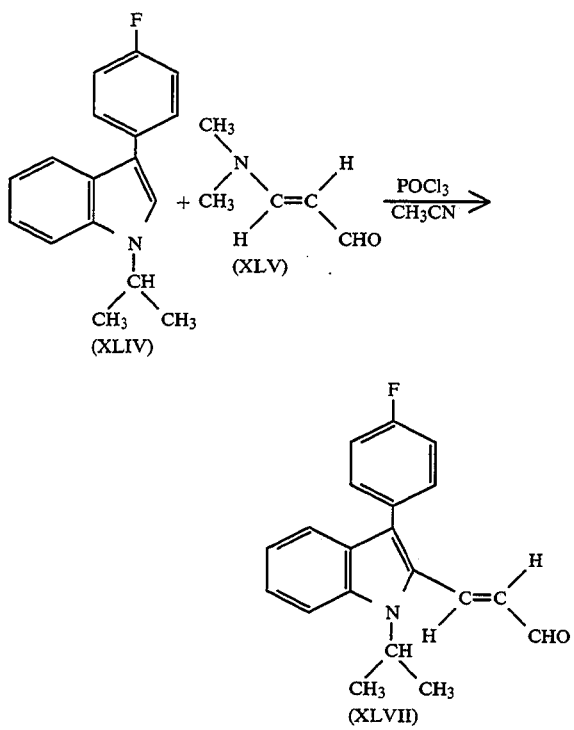

Initial Procedure

A solution of 50 ml. (49.6 g., 0.5 mole) of 3-N,N-dimethylaminoacrolein (Compound XLV) in 200 ml. of dry acetonitrile is slowly added over a 30 min. period to a solution of 50 ml. (82.5 g., 0.5392 mole) of phosphorus oxychloride in 200 ml. of dry acetonitrile stirred at −10°–0° C. under nitrogen. 45.3 g. (0.1788 mole) of Compound XLIV is added portionwise over a 2 min. period to the reaction mixture stirred at 0°–5° C. The reaction mixture is refluxed for 24 hours under nitrogen, cooled to room temperature and slowly poured (over a 20 min. period) into a cold (10° C.) stirred mixture of 2 l. of toluene and a solution of 130 g. of sodium hydroxide in 2 l. of water so that the temperature does not exceed 26° C. The reaction mixture is filtered to remove the insolubles, and the toluene layer is separated and washed twice with 1 l. portions of water. The additional insolubles are removed by filtration, and the toluene layer is evaporated at reduced pressure and 50°–60° C. The obtained viscous oil is chromatographed on 550 g. of silica gel (20-230 mesh A.S.T.M.) using methylene chloride as the eluant; twenty 100 ml. fractions are collected over a 2 hour period. The fractions containing the desired product (as determined by thin layer chromatography) are combined and evaporated to dryness at reduced pressure and 50°–60° C. to obtain the crude solid product (48.5 g.). The crude product is dissolved in 70 ml. of refluxing absolute ethanol, the obtained solution is cooled to 65° C., 70 ml. of n-heptane is added, and the resulting solution is cooled to −5°–0° C. for 15 min. The precipitated solids are collected by filtration, washed with 20 ml. of ice cold n-heptane and vacuum dried at 50°–55° C. to obtain the yellow product (32.1 g. (58.4%)), m.p. 122°–123° C. a second crop may be obtained. A subsequent batch melted at 129°–132° C.

Improved Procedure

A mixture of 190 ml. (2.04 moles) of phosphorus oxychloride and 760 ml. of dry acetonitrile is stirred at −3° C., a solution of 190 ml. (1.85 moles) of 3-N,N-dimethylaminoacrolein in 760 ml. of dry acetonitrile is added over a period of 45 minutes, while maintining a temperature of −3°–3° C., with stirring, the reaction mixture is stirred at this temperature for 5 minutes, 173 g. (0.68 mole) of Compound XLIV is added over a period of 5 minutes with stirring at about 0° C., and the reaction mixture is refluxed for 24 hours and cooled to 20° C., the reaction mixture being maintained under nitrogen throughout. The reaction mixture is slowly poured onto a mixture of 322 g. of sodium hydroxide, 4.5 l. of water, 4.5 l. of toluene and 1.0 kg. of crushed ice, during the course of which the temperature rises from −15° C. to 10° C. The obtained solution is filtered through 220 g. of Celite®, the filter cake is washed twice with 200 ml. portions of toluene, and the washings are combined with the filtrate. The organic phase is separated and washed four times with 2.0 l. portions of water. The organic phase is filtered through 93 g. of Celite®, the filter cake is washed twice with 150 ml. portions of toluene, and the washings are combined with the filtrate. The toluene is distilled at a pressure of 30–50 mm. Hg. and a temperature of 40°–45° C., and the resulting oil is dissolved in 700 ml. of methylene chloride and filtered through 700 g. of 70-230 mesh A.S.T.M. silica gel previously wet with methylene chloride. The filter cake is washed six times with 500 ml. portions of methylene chloride, and the washings are combined with the filtrate. The methylene chloride is distilled at 30-50 mm Hg. and a maximum temperature of 50° C., 370 ml. of isopropanol is added to the residue, and the distillation is continued until a vapor temperature of 80° C. is obtained. The mixture is permitted to slowly cool to 31° C., coooled to 13° C. and maintained at 13° C. for 10 minutes. The solid is collected by filtration, washed three times with 100 ml. portions of cold (10° C.) isopropanol and vacuum dried at 40°–45° C. for 16 hours to obtain the 96.7% pure product (147 g. (68%)), m.p. 128°–129° C.

STEP 5 (REACTION A)

Methyl (±)-(E)-7-[3'-(4''-fluorophenyl)-1'-(1''-methylethyl)indol-2'-yl]-5-hydroxy-3-oxohept-6-enoate

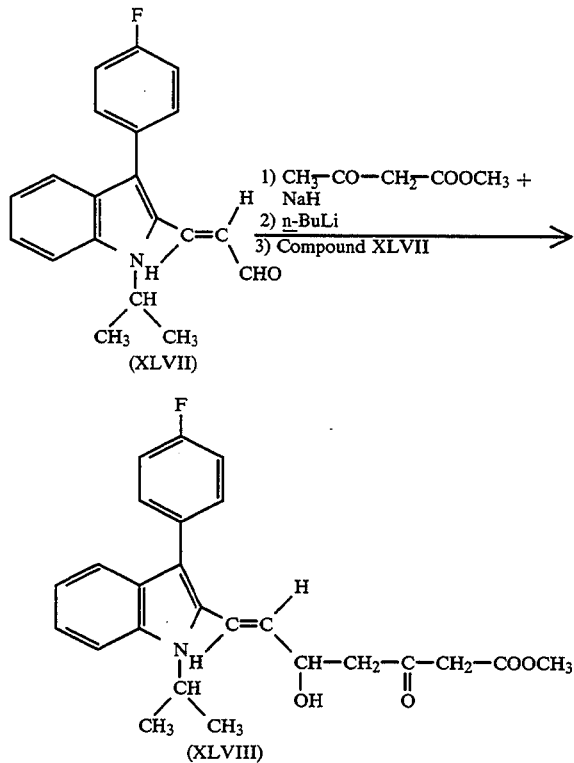

Initial Procedure 4.6 ml. (43 mmol.) of methyl acetoacetate is added dropwise to 1.7 g. of n-pentane-washed 60% (by weight) sodium hydride/mineral oil (43 mmol.) in 500 ml. of dry tetrahydrofuran stirred at 0° C. under nitrogen. The reaction mixture is maintained for 20 min., 27.5 ml. of 1.6M. n-butyllithium/n-hexane (44 mmol.) is added dropwise, the reaction mixture is maintained for 20 min., a solution of 8.0 g. (26 mmol.) of Compound XLVII in 200 ml. of dry tetrahydrofuran is rapidly added dropwise, and the reaction mixture is maintained for 30 min., the reaction mixture being stirred at 0° C. under nitrogen throughout. The reaction mixture is quenched with 20 ml. of concentrated hydrochloric acid, poured into 500 ml. of ice cold water and extracted with about 600 ml. of diethyl ether. The diethyl ether extract is washed three times with saturated sodium chloride solution, dried over anhydrous magnesium sulfate and evaporated at reduced pressure to an orange oil. The oil is triturated with n-pentane, the n-pentane is decanted, and the oil is vacuum dried to obtain the crude product (12.2 g. (112%)). Yellow seed crystals of the product were obtained from the n-pentane used in the trituration, m.p. 95°–97° C.

Improved Procedure 27 g. of 80% sodium hydride/mineral oil (0.9 mole) is added to 600 ml. of dry tetrahydrofuran stirred at −10° C., a solution of 108 g. (0.92 mole) of methyl acetoacetate in 300 ml. of dry tetrahydrofuran is added dropwise at a rate such that the temperature does not exceed 5° C., the reaction mixture is stirred at 0°–5° C. for 1 hour and cooled to −10° C., 550 ml. of 1.65M. n-butyllithium/n-hexane (0.91 mole) is added at a rate such that the temperature does not exceed 0° C., the reaction mixture is stirred at 3° C. for 5 minutes and cooled to −10° C., a solution of 153.5 g. (0.5 mole) of Compound XLVII in 800 ml. of dry tetrahydrofuran is added dropwise at a rate such that the temperature does not exceed 0° C., and the reaction mixture is stirred at 0°–5° C. for 15 minutes, the reaction mixture being maintained under nitrogen throughout. The reaction mixture is poured into a mixture of 1.5 l. of saturated ammonium chloride solution and 150 ml. of concentrated hydrochloric acid, the mixture is stirred for 15 minutes, and the organic layer is separated, washed twice with 500 ml. portions of saturated sodium chloride solution, dried over 900 g. of anhydrous sodium sulfate, filtered and concentrated at reduced pressure and a temperature not in excess of 45° C. The oily residue is dissolved in 400 ml. of toluene, about 100 ml. of solvent is distilled (to remove any residual tetrahydrofuran), and the obtained solution is seeded and cooled at 0° C. for 5 hours. The obtained crystals are collected by filtration, washed with 250 ml. of 1:2 (by volume) toluene/hexane, washed with 200 ml. of hexane and vacuum dried at 50° C. for 3 hours to obtain the product (184 g. (86%)), m.p. 99°–100° C.

The product is a racemate that may be resolved into its R and S components.

STEP 6 (REACTION B)

Methyl(±)-erythro-(E)-3,5-dihydroxy-7-[3'-(4''-fluorophenyl)-1'-(1''-methylethyl)indol-2'-yl]hept-6-enoate

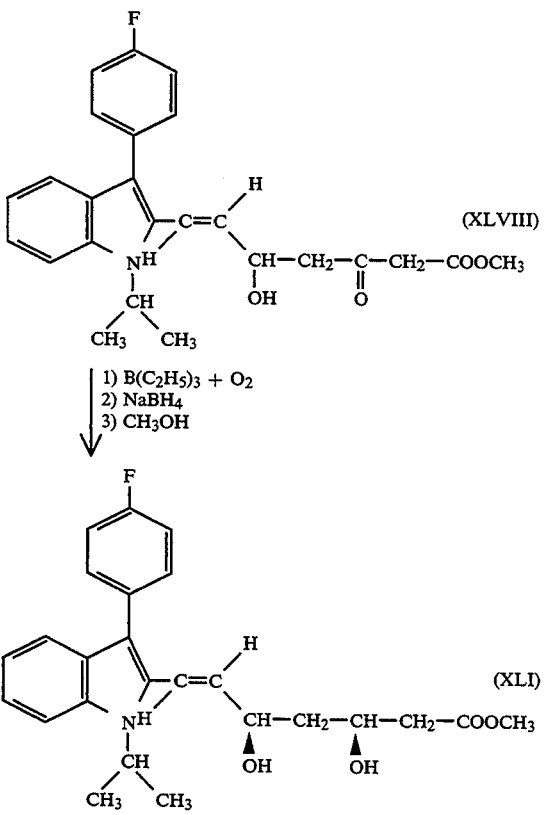

Initial Procedure (a) 30 ml. of 1M. triethylborane/tetrahydrofuran (30 mmol.) is added dropwise to a solution of 12.2 g. (26 mmol. assuming 100% yield) of crude Compound XLVIII from Step 5 in 400 ml. of dry tetrahydrofuran (distilled over lithium aluminum hydride) stirred at room temperature, 55 ml. of air (at 760 mm. Hg. and 25° C.) is bubbled through over 5 min., and the reaction mixture is stirred at room temperature under nitrogen for 2 hours. The reaction mixture is cooled to −80° C., 1.3 g. (34 mmol.) of sodium borohydride is added, and the reaction mixture is stirred overnight at −80° C. under nitrogen. The reaction mixture is allowed to warm to −10°−0° C., quenched by the dropwise addition of sufficient 2N. hydrochloric acid to lower the pH to 2 and extracted with diethyl ether. The diethyl ether extract is washed twice with saturated sodium chloride solution, dried over anhydrous magnesium sulfate and evaporated at reduced pressure to a yellow oil, the crude ethylborate ester. 400 ml. of anhydrous methanol is added, and the reaction mixture is stirred at room temperature for 2.5 hours. The methanol is evaporated at reduced pressure and 40° C., and the residue is dissolved in 4:1 (by volume) chloroform/ethyl acetate and chromatographed on a silica gel column (3″ diameter×8″ height) using the same solvent as the eluant. The fractions containing the relatively pure product are combined and evaporated at reduced pressure to obtain the product as an oil (6.7 g. (61% overall yield from the Initial Procedure of Step 5 and this part of this step)).

(b) An impure chromatography fraction (containing some product) is evaporated at reduced pressure, and the residue is triturated with diethyl ether and n-pentane and seeded with a crystal that formed upon addition of the methanol to the ethylborate ester to obtain the product as a white powder (0.7 g. (6%)), m.p. 122°−124° C.

The product is a racemate which may be resolved into two optically pure enantiomers, the 3R,5S and 3S,5R isomers, of which the former is preferred. It contains a small amount of the corresponding threo racemate (2–4%).

Modified Procedure:

(c) A suspension of 22.7 g. (0.6 mole) of sodium borohydride powder in 1 l. of isopropanol is stirred at −15° C., a solution of 141 g. (0.333 mole) of Compound XLVIII in 2.1 of ethyl acetate is added with stirring over a period of 1.5–1.65 hours, the temperature being maintained below −15° C., and the reaction mixture is stirred at a temperature below −15° C. for 15 minutes, the reaction mixture being stirred under nitrogen throughout. The reaction mixture is slowly poured into a mixture of 1.4 l. of saturated ammonium chloride solution and 50 ml. of concentrated hydrochloric acid stirred at 20°−25° C., and the obtained mixture is stirred at the same temperature for 10 minutes (until no more gas is evolved). The organic layer is separated, washed with 500 ml. of saturated sodium chloride solution and evaporated at reduced pressure and a temperature not in excess of 50° C., the obtained yellow-orange oily residue is dissolved in 2 l. of isopropanol, 20 g. (0.323 mole) of boric acid is added, and the mixture is heated to reflux temperature and filtered. The filtrate is allowed to cool to 20° C. with gentle stirring and is gently stirred at this temperature for 3 hours. The obtained crystals are collected by filtration, washed twice with 200 ml. portions of isopropanol (the erythro:threo ratio of the obtained 2-(1′-methylethoxy)-1,3,2-dioxaborinane is about 7:3, with that of the product remaining in the mother liquor being about 1:10) and dissolved in 2.6 l. of isopropanol by refluxing for 2–10 minutes. The solution is cooled to 20°−25° C. with gentle stirring and is gently stirred at this temperature for 3 hours. The obtained crystals are collected by filtration and washed twice with 200 ml. portions of isopropanol (the erythro:threo ratio of the obtained 2-(1′-methylethoxy)-1,3,2-dioxaborinane is about 5.25–7.33:1, with that of the product remaining in the mother liquor being about 1:9). The recrystallization procedure is repeated (the erythro:threo ratio of the obtained 2-(1′-methylethoxy)-1,3,2-dioxaborinane is about 11.5–19:1, with that of the product remaining in the mother liquor being about 1:5). The recrystallization procedure is repeated again, and the solid is vacuum dried at 70°–80° C. for 3–4 hours to obtain methyl 6-[2′-[3″-(4‴-fluorophenyl)-1″-(1‴-methylethyl)-1H-indol-2″-yl]ethenyl]-2-(1′-methylethoxy)-1,3,2-dioxaborinane-4-acetate (Compound XLVIIIA) (50.8 g. (30%)), m.p. 153°−156° C. The erythro:threo ratio of the product is at least 39:1, with that of the product remaining in the mother liquor being about 1:1.

A suspension of 63 g. (0.1277 mole) of Compound XLVIIIA in 650 ml. at methanol is refluxed under nitrogen for 45 minutes, the obtained solution is filtered and evaporated to dryness at reduced pressure, and the oily residue is dissolved in 200 ml. of ethyl acetate. 700 ml. of n-hexane is added, the mixture is kept 20°−25° C. for at least 4 hours, and the obtained crystals are collected by filtration, washed with 200 ml. of n-hexane and vacuum dried at 60° C. for 3 hours to obtain the product (47 g. (87%)), m.p. 122°−124° C.

The product is the erythro racemate. It may be resolved by conventional means to obtain the 3R,5S and 3S,5R enantioners, of which the former is preferred, and contains a maximum of 2% of the corresponding threo racemate.

EXAMPLE 6

Erythro-(±)-(E)-3,5-dihydroxy-7-[3′-(4″-fluorophenyl)-1′-(1″-methylethyl)indol-2′-yl]hept-6-enoic acid (Reactions C and D)

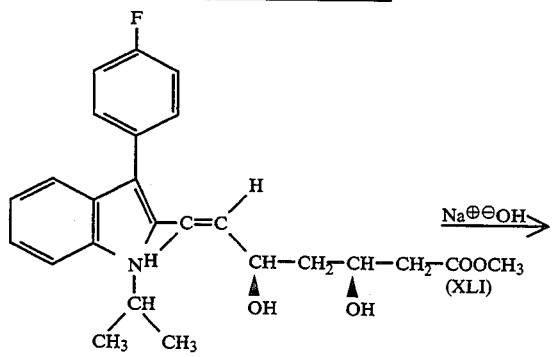

-continued
(Reactions C and D)

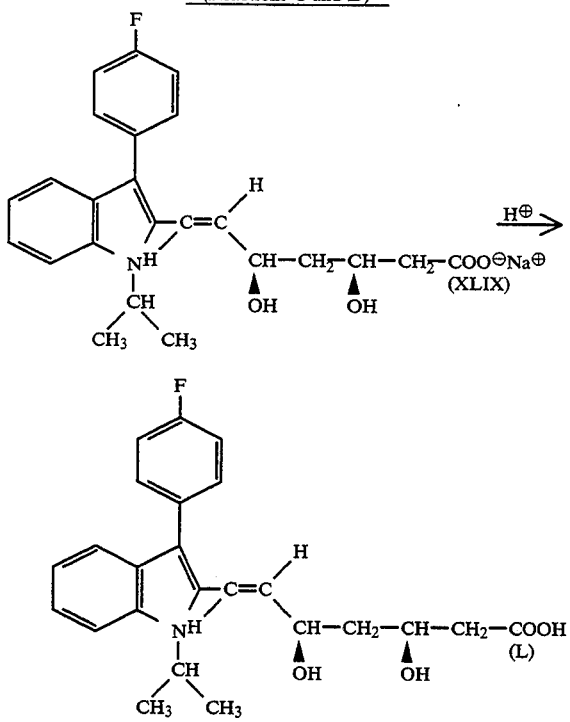

(a) 17.3 ml. of 1N. sodium hydroxide solution (17.3 mmol.) is added dropwise to a solution of 6.7 g. (15.7 mmol.) of Compound XLI (from Step 6, Initial Procedure, Part (a) of Example 5) in 300 ml. of methanol, the reaction mixture is stirred at room temperature for 2 hours, and the methanol is evaporated at reduced pressure to obtain crude racemic Compound XLIX.

(b) 4.5 ml. of 1N. sodium hydroxide solution (4.5 mmol.) and 2.0 g. (4.7 mmol.) of Compound XLI (from Example 5) are stirred in 150 ml. of ethanol at room temperature for 2 hours, the solvent is evaporated at reduced pressure, and the residue is dissolved in 50 ml. of water. The aqueous solution is gently extracted with diethyl ether, the traces of ether in the aqueous layer are removed at reduced pressure, and the aqueous layer is freeze dried to obtain racemic Compound XLIX (1.8 g. (88%)), m.p. 194°–197° C.

(c) The crude Compound XLIX from Part (a) is dissolved in water, and the solution is acidified to pH 2 with 2N. hydrochloric acid and extracted with diethyl ether. The diethyl ether extract is washed three times with saturated sodium chloride solution, dried over anhydrous magnesium sulfate and evaporated at reduced pressure to obtain crude solid racemic Compound L (6.9 g.).

Pure Compound L (containing less than 2% of the corresponding threo racemate) may be obtained from Compound XLIX of comparable purity (Example 8) by the process of this part of this example. M.p. 127°–128° C.

Compounds XLIX and L may both be resolved into two optically pure enantiomers, the 3R,5S and 3S,5R isomers, of which the former is preferred.

EXAMPLES 7(a) and 7(b)

(E)-(±)-Trans-4-hydroxy-6-[2'-[3''-(4'''-fluorophenyl)-1''-(1'''-methylethyl)indol-2''-yl]ethenyl]-3,4,5,6-tetrahydro-2H-pyran-2-one and the corresponding cis lactone (Reaction E)

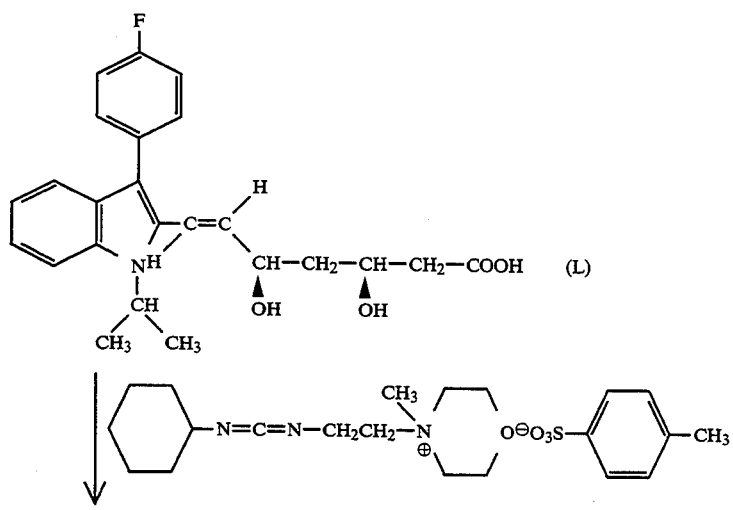

-continued

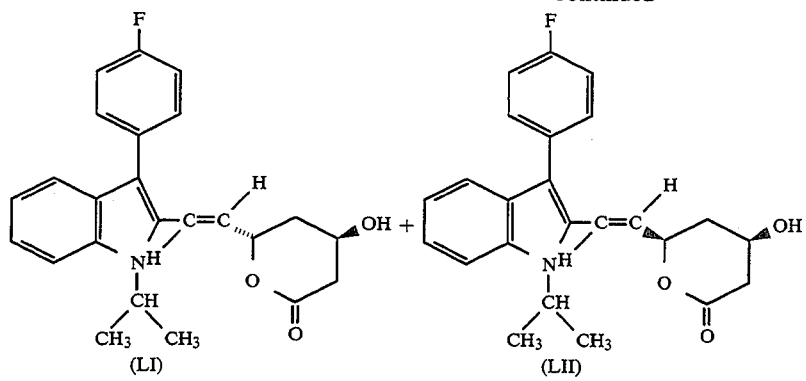

(a) 6.9 g. (15.7 mmol. assuming 100% yield) of crude Compound L (from Part (c) of Example 6) and 7 g. (16.5 mmol.) of N-cyclohexyl-N'-[2-(N''-methylmorpholinium)ethyl]carbodiimide p-toluenesulfonate are stirred in 300 ml. of methylene chloride at room temperature for 3 hours. The reaction mixture is extracted with water, dried over anhydrous magnesium sulfate and evaporated at reduced pressure. The residual oil is chromatographed on a silica gel column (3" diameter×6" height) utilizing 7:2:1 (by volume) methyl t-butyl ether/n-hexane/acetone as the eluant. The initial fractions, containing the racemic trans lactone, are combined and evaporated at reduced pressure to obtain the product as a foam (2.6 g.).

N.M.R. (CDCl₃): 1.68 (6H doublet) 1.75–2.05 (3H multiplet) 2.55–2.82 (2H multiplet) 4.38 (1H multiplet) 4.82 (1H quintet) 5.25 (1H multiplet) 5.72 (1H quartet) 6.75 (1H doublet) 7.05–7.6 (8H multiplet)

I.R. (CHCl₃): 3600 (m), 3480 (broad), 2980 (m), 2930 (m), 1720 (s) and 1225 (s) cm.⁻¹ and others The product is a racemate that may be resolved by, for example, the process set forth above into two optically pure enantiomers, the 4R,6S and 4S,6R isomers, of which the former is preferred.

(b) The chromatography fractions from Part (a) of this example containing the cis lactone are combined and evaporated at reduced pressure to obtain the solid product (0.22 g.), m.p. 170°–175° C. (dec.).

N.M.R. (CDCl₃): 1.58 (1H multiplet) 1.68 (6H doublet) 2.05 (1H doublet) 2.22 (1H multiplet) 2.52 (1H quartet) 2.95 (1H quartet) 4.3 (1H multiplet) 4.8 (2H multiplet) 5.72 (1H quartet) 6.78 (1H doublet) 7.1–7.6 (8H multiplet)

I.R. (CHC₃): 3600 (m), 3480 (broad), 2980 (m), 2930 (m), 1720 (s) and 1225 (s) cm.⁻¹ and others The product is a racemate that may be separated into two optically pure enantiomers, the 4R,6R and 4S,6S isomers of which the former is preferred. The cis lactone results from a small amount of the threo isomer of Compound XLI formed in the Initial Procedure of Step 6 of Example 5 and not separated therefrom which is carried through Reactions C and D (Parts (a) and (c) of Example 6) and Reaction E (Part (a) of this example).

Example 8

Sodium erythro-(±)-(E)-3,5-dihydroxy-7-[3'-(4''-fluorophenyl)-1'-(1''-methylethyl)indol-2'-yl]hept-6-enoate

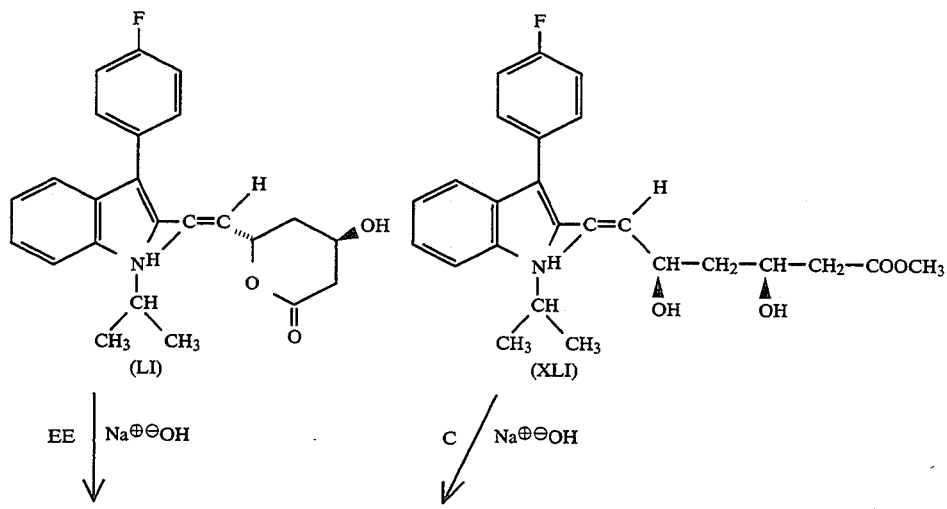

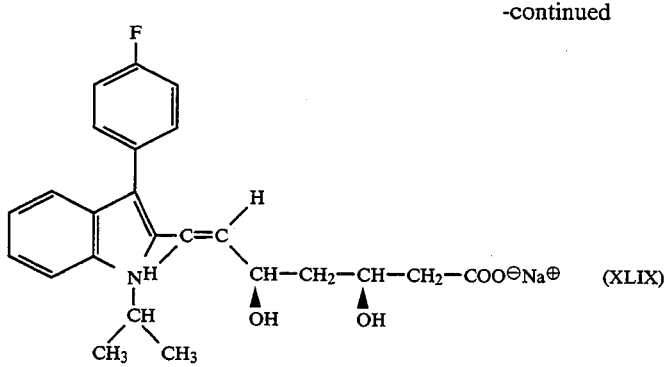

(XLIX)

Reaction EE (a) 2.6 g. (6.6 mmol.) of Compound LI (from Part (a) of Example 7), 12.6 ml . of 0.5N. sodium hydroxide solution (6.3 mmol.) and 200 ml. of absolute ethanol are stirred for 2 hours at room temperature, the solvent is evaporated at reduced pressure, and the residue is dissolved in 150 ml. of water. The aqueous solution is gently washed with diethyl ether and freeze dried to obtain the solid racemic product (2.7 g.).

N.M.R. (CDCl$_3$+CD$_3$OD): 1.55 (1H multiplet) 1.6 (6H doublet ) 2.2–2.45 (3H multiplet) 4.08 (1H multiplet) 4.42 (1H multiplet) 4.9 (1H quintet ) 5.75 (1H doublet of a doublet) 6.68 (1H doublet) 7–7.2 (4H multiplet) 7.48–7.58 (4H multiplet)

I.R. (KBr): 3413 (broad s), 2978 (m), 2936 (m), 1572 (s) and 1216 (s) cm.$^{-1}$ and others The racemic product may be resolved into two optically pure enantiomers, the 3R,5S and 3S,5R isomers, of which the former is preferred. See Example 14.

Reaction C (b) 107.6 ml. of 1N. sodium hydroxide solution (0.1076 mole) is added to a suspension of 46.7 g. (0.11 mole) of Compound XLI (containing not more than about 2% of the corresponding threo racemate) in 800 ml. of methanol stirred at 20°–25° C. under nitrogen, and the reaction mixture is stirred under the same conditions for 2.5 hours. The solvent is distilled at reduced pressure and 40° C. until a precipitate begins to form. 400 ml. of water is added, and the balance of the methanol is distilled at reduced pressure and 40° C. The solution is cooled to 20°–25° C. and extracted six times with 250 ml. portions of methyl t-butyl ether, and the residual methyl b-butyl ether is evaporated from the aqueous phase at reduced pressure. The aqueous solution is divided in half, and each half is shell-freezed and lyophilized for 24–36 hours at −65°--−60° C. and 100 mTorr→ about 5 μm.Hg., i.e., until the pressure reaches about 5 μm.Hg. and the temperature reaches 20°–25° C. utilizing an aluminum foil-wrapped flask to obtain the product (Compound XLIX) as an amorphous colorless powder (44.2 g. (94.8%)), m.p. 212°–213° (dec.) (yellows at 110°–125° C., turns orange-red at about 190° C. and softens at about 206° C.).

The product is a racemate that may be resolved by conventional means to obtain the 3R,5S and 3S,5R enantiomers, of which the former is preferred. It contains a small amount (about 1.5%) of the corresponding threo racemate and, possibly, a small amount of water.

EXAMPLE 9

Sodium threo-(±)-(E)-3,5-dihydroxy-7-[3'-(4''-fluorophenyl)-1'-(1''-methylethyl)indol-2'-yl]hept-6-enoate (Reaction EE)

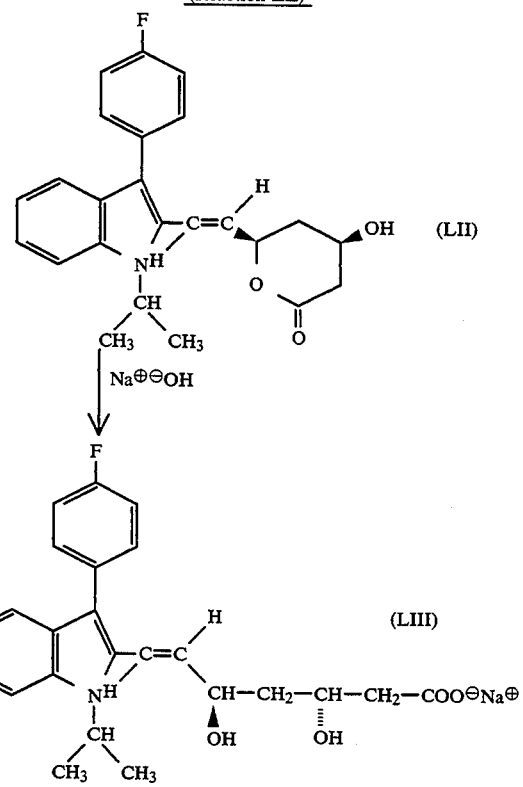

0.24 ml. of 1N. sodium hydroxide solution (0.24 mmol.) is added to a suspension of 100 mg. (0.25 mmol.) of Compound LII in 10 ml. of ethanol, the resulting solution is stirred for 1 hour at room temperature, and the solvent is evaporated at reduced pressure. The residue is dissolved in chloroform, and the solution is triturated with diethyl ether to obtain the solid product (83 mg. (73%)).

N.M.R. (D$_2$O): 1.05 (6H doublet) 1.28 (2H multiplet) 2.18 (2H doublet) 3.95 (1H multiplet) 4.2 (1H multiplet) 4.5 (1H multiplet) 5.4 (1H doublet of a doublet) 6.4 (1H doublet) 6.5–7.2 (8H multiplet)

The racemic threo compound may be resolved by conventional means into its 3R,5R and 3S,5S components.

EXAMPLE 10

(E)-Trans-6S-[2'-[3''-(4'''-fluorophenyl)-1''-methylindol-2''-yl]ethenyl]-4R-hydroxy-3,4,5,6-tetrahydro-2H-pyran-2-one

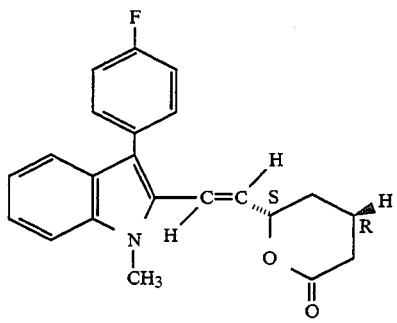

(XLA)

STEP 1 (REACTION R)

3-(4'-Fluorophenyl)-1-methylindole-2-carboxaldehyde

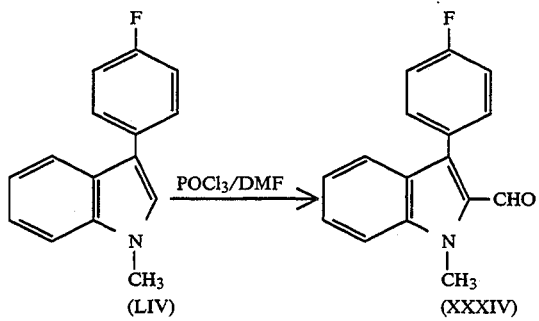

78.5 ml. (0.84 mole) of phosphorus oxychloride is added dropwise over a 20 min. period to 213 ml. of dimethylformamide stirred at 0° C. under nitrogen, the temperature of the reaction mixture not being allowed to exceed 10° C. The reaction mixture is heated to 80° C., a solution of 163.5 g. (0.727 mole) of 3-(4'-fluorophenyl)-1-methylindole in 270 ml. of dimethylformamide is added at a rate such that the temperature of the reaction mixture is maintained at 81°–83° C., the reaction mixture is maintained at 80°–81° C. for 5 hours and cooled to 10° C., and 1 l. of 15% sodium hydroxide solution is added dropwise at a rate such that the temperature of the reaction mixture is maintained at 35°–40° C., the reaction mixture being stirred under nitrogen throughout. The reaction mixture is cooled to 25° C., and the solids are collected by filtration, washed three times with 500 ml. portions of water and dissolved in 500 ml. of methylene chloride. The methylene chloride solution is filtered through 500 ml. of silica gel (70–230 mesh A.S.T.M.) and the silica gel is carefully washed with 2 l. of methylene chloride. The methylene chloride solutions are combined and concentrated to a volume of 300 ml. at reduced pressure, 300 ml. of absolute ethanol is added, and the reaction mixture is distilled until the internal temperature reaches 78° C. The reaction mixture is cooled to 0° C. and the precipitated bright yellow product is collected by filtration and vacuum dried at room temperature (153.9 g. (84%)), m.p. 80.5°–81.5° C. A slightly less pure second crop may be obtained from the mother liquor.

STEP 2 (REACTION S)

3-(4'-Fluorophenyl)-2-hydroxymethyl-1-methylindole

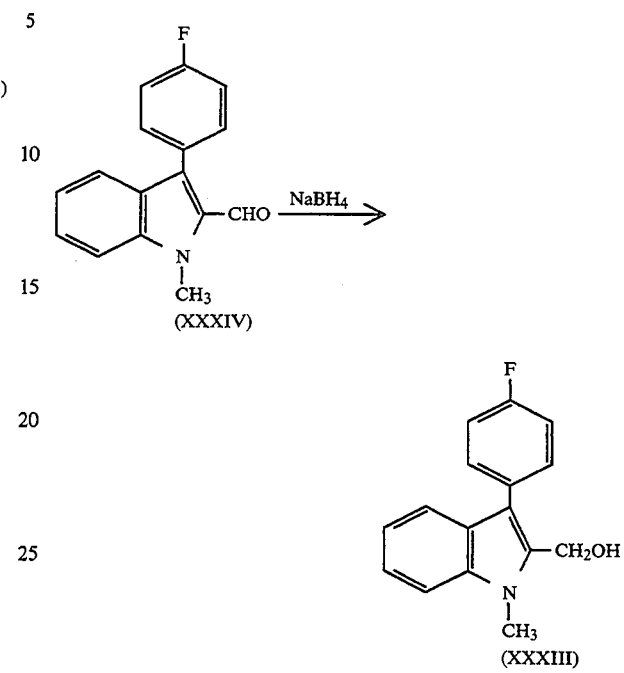

A solution of 160 g. (0.6324 mole) of Compound XXXIV in 650 ml. of tetrahydrofuran is added over a 20 min. period to a mixture of 9.6 g. (0.25 mole) of sodium borohydride, 650 ml. of tetrahydrofuran and 65 ml. of methanol stirred at 0° C. under nitrogen, the temperature of the reaction mixture not being allowed to exceed 14° C. The reaction mixture is stirred under nitrogen at 5°–10° C. for 30 min., and the tetrahydrofuran and methanol are distilled at atmospheric pressure. 1 l. of toluene is added to the oily residue (200–300 ml.) and the residual tetrahydrofuran is distilled at atmospheric pressure until the temperature reaches 108°–110° C. The toluene solution is cooled to 40° C., 1.3 l. of 0.5N. sodium hydroxide is rapidly added, and the two phases are mixed and separated. The organic phase is heated to 50°–55° C., 1.1 l. of n-hexane is added, the solution is cooled to 5° C., and the precipitated colorless product is collected by filtration and vacuum dried for 16 hours at room temperature. (136 g. (84.3%)), m.p. 110°–111° C. A less pure second crop (20 g.) may also be obtained.

STEP 3 (REACTION T)

2-Chloromethyl-3-(4'-fluorophenyl)-1-methylindole

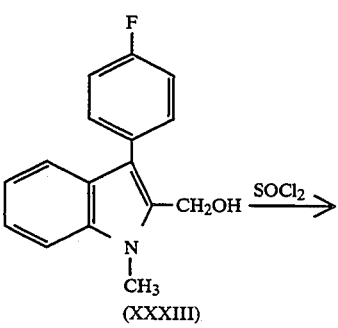

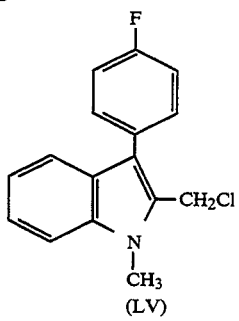

29.5 ml. (0.404 mole) of thionyl chloride is added over a 10 min. period to a solution of 63.8 g. (0.25 mole) of Compound XXXIII in 650 ml. of dry tetrahydrofuran (dried over molecular sieves) stirred at −7° C. under nitrogen. The reaction mixture is stirred at −5°−0° C. under nitrogen for 2.5 hours, 350 ml. of toluene is added (with cooling to keep the temperature of the reaction mixture at or below 5° C.), tetrahydrofuran and excess thionyl chloride are distilled at 0.5–2 mm. Hg. and 0°–10° C. until the volume of the reaction mixture is about 400 ml., an additional 350 ml. of toluene is added and another 100 ml. of solvent is distilled at 0.5–1 mm. Hg. and 10°–20° C. to obtain a solution of the product in toluene.

STEP 4 (REACTION V)

3-(4'-Fluorophenyl)-1-methyl-2-triphenylphosphoniummethylindole chloride

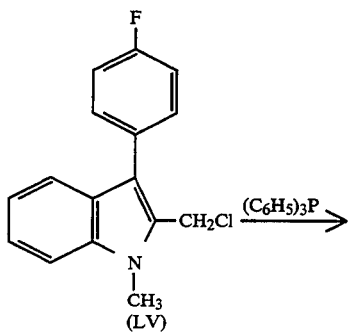

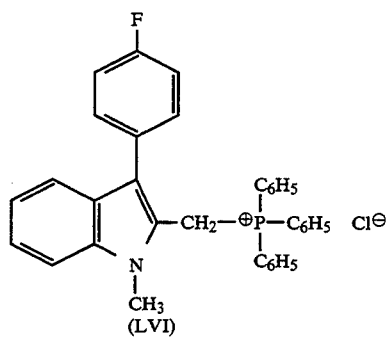

A solution of 66.2 g. (0.25 mole) of triphenylphosphine in 1 l. of toluene is added over a 3 min. period to the solution of Compound LV obtained in Step 3 stirred at 15°–20° C. under nitrogen, and the reaction mixture is stirred at 108°–110° C. under nitrogen for 5 hours and cooled to 25° C. The product is collected by filtration, washed twice with 50 ml. portions of toluene and once with 50 ml. of n-heptane and vacuum dried, 93 g. (70%), m.p. 270°–271° C. (dec.).

STEP 5 (REACTION W)

(E)-4βR-(1',1'-dimethylethyl-diphenylsilyloxy)-6αS-[2'-[3''-(4'''-fluorophenyl)-1''-methylindol-2''-yl]ethenyl]-2β-methoxy-3,4,5,6-tetrahydro-2H-pyran and the corresponding (Z) compound

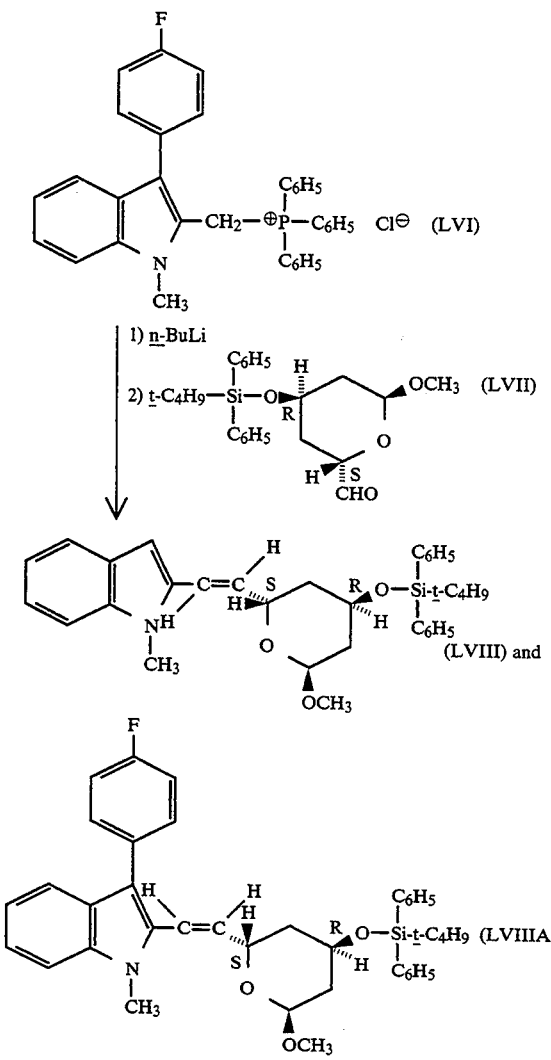

6.0 ml. of 1.3M. n-butyllithium/n-hexane (7.8 mmol.) is added dropwise over a 7 min. period to a slurry of 4.0 g. (7.47 mmol.) of Compound LVI (stripped from toluene at reduced pressure and dried under high vacuum prior to use) in 100 ml. of dry tetrahydrofuran (freshly distilled from sodium and benzophenone) stirred at room temperature under nitrogen. The reaction mixture is cooled to 0° C., and 2.98 g. (7.48 mmol.) of Compound LVII (stripped from toluene at reduced pressure and dried under high vacuum prior to use) in 20 ml. of dry tetrahydrofuran is added dropwise over a 5 min. period, an additional 10 ml. of dry tetrahydrofuran is added, and the reaction mixture is maintained at about 0° C. for 45 min., allowed to warm to room temperature and maintained at room temperature for 17 hours, the reaction mixture being stirred under nitrogen throughout. The reaction mixture is poured into 500 ml. of water and extracted four times with 250 ml. portions of diethyl ether. The diethyl ether extracts are combined and dried over anhydrous magnesium sulfate and then over anhydrous sodium sulfate and evaporated at reduced pressure. The last traces of diethyl ether are removed under high vacuum to obtain a semi-solid residue. The residue is subjected to medium pressure liquid chromatography utilizing a silica gel column and methylene chloride as the eluant, with those fractions containing one product and one or more contaminants or a mixture of the products (with or without one or more contaminants) as determined by thin layer chromatography being recycled, to obtain 1.83 g. (39.6%) of the (E) (i.e., trans) olefin (Compound LVIII) as an orange foam and 0.671 g. (14.5%) of the (Z) (i.e., cis) olefin (Compound LVIIIA) also as an orange foam.

STEP 6 (REACTION X)

(E)-4βR-(1'1'-dimethylethyl-diphenylsilyloxy)-6αS-[2'-[3''-(4'''-fluorophenyl)-1''-methylindol-2''-yl]ethenyl]-2-hydroxy-3,4,5,6-tetrahydro-2H-pyran and the corresponding 6βR compound

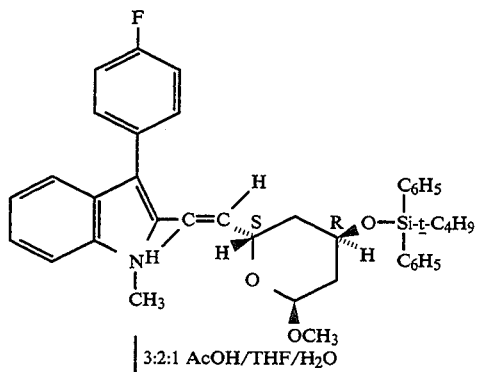
(LVIII)

3:2:1 AcOH/THF/H₂O
60° C.

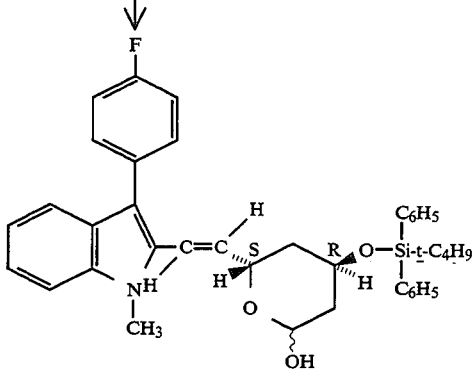

and

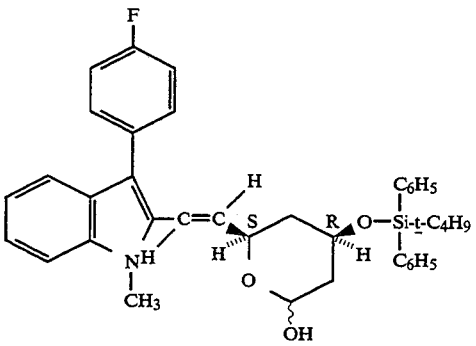
(LX)

1.18 g. (1.9 mmol.) of Compound LVIII is dissolved in 56 ml. of glacial acetic acid, 37.2 ml. of tetrahydrofuran is added, and 18.6 ml. of distilled water is slowly added, the reaction mixture being stirred at room temperature throughout. The reaction mixture is stirred at 60° C. for 18.5 hours and allowed to cool. The tetrahydrofuran is evaporated at reduced pressure, and the reaction mixture is poured into 500 ml. of distilled water and extracted four times with 300 ml. portions of diethyl ether. The diethyl ether extracts are combined, washed with saturated sodium bicarbonate solution (until no gas is evolved upon shaking), dried over anhydrous magnesium sulfate and then over anhydrous sodium sulfate and evaporated to dryness at reduced pressure. The last traces of solvent are removed under high vacuum to obtain a yellow foam. Flash chromatography of the foam utilizing 250 g. of silica gel and 1:1 (by volume) diethyl ether/n-hexane as the eluant yielded 329.9 mg. (28.6%) of Compound LIX and 366.7 mg. (31.7%) of Compound LX.

STEP 7 (REACTION Y)

(E)-4βR-(1',1'-dimethylethyl-diphenylsilyloxy)-6αS-[2'-[3''-(4'''-fluorophenyl)-1''-methylindol-2''-yl]ethenyl]-3,4,5,6-tetrahydro-2H-pyran-2-one (LIX)

(LIX)

N-methylmorpholine-N-oxide +
RuCl₂(P(C₆H₅)₃)₃/CH₃COCH₃

(LXI)

A solution of 236.8 mg. (0.391 mmol.) of Compound LIX in 8 ml. of acetone (passed through a column of Activity I alumina immediately prior to use) is added to 137.5 mg. (1.174 mmol.) of N-methylmorpholine N-oxide (obtained by heating N-methylmorpholine N-oxide hydrate at 90° C. for 2–3 hours under high vacuum), the reaction mixture is stirred at room temperature under nitrogen until the solid dissolves, 23.5 mg. (0.025 mmol.) of dichlorotris(triphenylphosphine)ruthenium (II) is added, and the reaction mixture is stirred under nitrogen for 55 min. 10 ml. of diethyl ether is added, and the resulting solid is washed several times with diethyl ether. The diethyl ether washings are combined, the diethyl ether is evaporated at reduced pressure to near dryness, and the residue is dissolved in 100 ml. of diethyl ether. The diethyl ether solution is washed twice with 100 ml. portions of ice-cold 2.5% hydrochloric acid, twice with 100 ml. portions of saturated sodium bicarbonate solution and once with 100 ml. of saturated sodium chloride solution, dried over anhydrous sodium sulfate and evaporated to dryness at reduced pressure to obtain the crude product as a yellow oil (243.4 mg.).

STEP 8 (REACTION Z)

(E)-Trans-6S-[2'-[3''-(4'''-fluorophenyl)-1''-methylindol-2''-yl]ethenyl]-4R-hydroxy-3,4,5,6-tetrahydro-2H-pyran-2-one

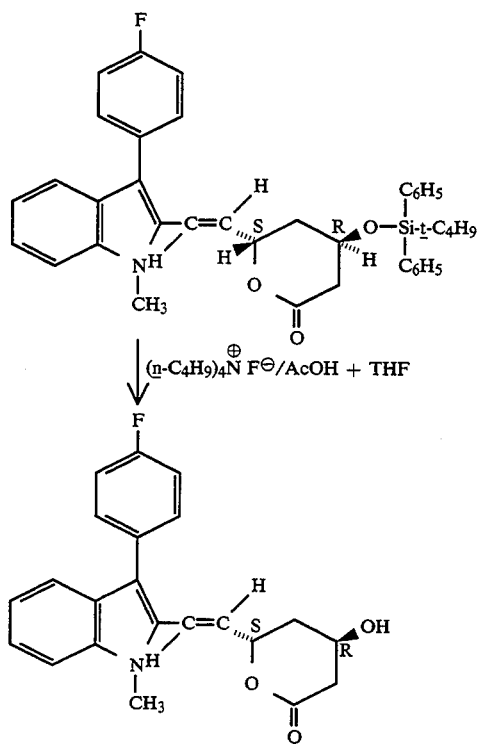

113 µl. of glacial acetic acid is added dropwise to a solution of 237.5 mg. (0.391 mmol.) of crude Compound LXI (from Step 7) in 18 ml. of dry tetrahydrofuran stirred at room temperature under nitrogen followed by the dropwise addition of 1.564 ml. of 1M. tetra-n-butylammonium fluoride/tetrahydrofuran. The reaction mixture is stirred at room temperature under nitrogen for 2 hours, poured into 200 ml. of ice-cold water and extracted four times with 75 ml. portions of diethyl ether. The organic phases are combined, washed once with 300 ml. of saturated sodium bicarbonate solution and once with 300 ml. of saturated sodium chloride solution and dried over anhydrous sodium sulfate. The solvent is evaporated at reduced pressure, with the last traces being evaporated under high vacuum to obtain a yellow oil which is triturated with diethyl ether to obtain the product as a pale yellow solid. Additional product is obtained from the mother liquor by repeating this procedure three times. A total of 83.5 mg. (58.5%), m.p. 139°–140° C., is obtained. $[\alpha]_D^{25} = -5.21°$ ($CH_2Cl_2$, c=0.82 g.)

N.M.R. ($CDCl_3$): 1.7–2.1 (3H multiplet) 2.71 (2H multiplet) 3.87 (3H singlet) 4.42 (1H multiplet) 5.31 (1H multiplet) 5.93 (1H doublet of a doublet; $J_1 = 16$ Hz., $J_2 = 6$ Hz.) 6.79 (1H doublet; J=16 Hz.) 7.1–7.6 (8H multiplet)

I.R. ($CHCl_3$): 3612, 3466, 3039, 3002, 2933, 1736, 1543, 1369 and 1256 cm.$^{-1}$ and others A second batch, obtained by resolution of the racemate by the procedure described above, had an $[\alpha]_D^{25} = -18.5°$ ($CHCl_3$, c=0.2 g.) See Example 4(a).

EXAMPLE 11

(E)-Cis-6R-[2'-[3''-(4'''-fluorophenyl)-1''-methylindol-2''-yl]ethenyl]-4R-hydroxy-3,4,5,6-tetrahydro-2H-pyran-2-one

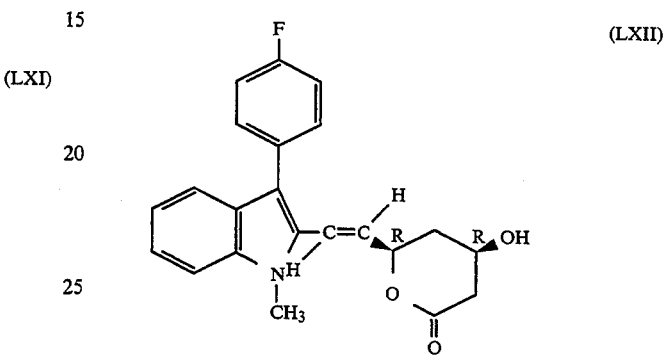

The product is obtained as an oil from Compound LX (Step 6 of Example 10) by the processes of Steps 7 and 8 of Example 10 and is purified by chromatography on silica gel utilizing 1:1 (by volume) ethyl acetate/methylene chloride as the eluant.

N.M.R. ($CDCl_3$): 1.71 (1H multiplet) 2.05 (1H multiplet) 2.31 (1H multiplet) 2.52 (1H doublet of a doublet, $J_1 = 17.5$ Hz., $J_2 = 8$ Hz.) 2.95 (1H doublet of a doublet), $J_1 = 17.5$ Hz., $J_2 = 5.5$ Hz. 3.85 (3H singlet) 4.31 (1H multiplet) 4.81 (1H multiplet) 5.97 (1H doublet of a doublet, $J_1 = 16$ Hz., $J_2 = 6$ Hz.) 6.77 (1H doublet, J = 16 Hz.) 7.09–7.72 (8H multiplet)

I.R. ($CH_2Cl_2$): 3601, 3034, 3026, 2962, 1742, 1366 and 1230 cm.$^{-1}$ and others $[\alpha]_D^{25} = +1.14°$ ($CH_2Cl_2$, c=1.05 g.)

EXAMPLE 12

(Z)-Trans-6S-[2'-[3''-(4'''-fluorophenyl)-1''-methylindol-2''-yl]ethenyl]-4R-hydroxy-3,4,5,6-tetrahydro-2H-pyran-2-one

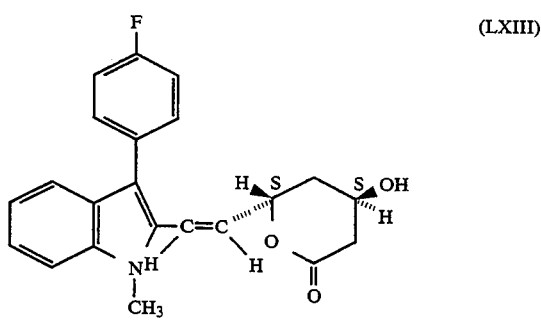

The product is obtained as an oil from Compound LVIIIA (Step 5 of Example 10) by the processes of Steps 6–8 of Example 10. $[\alpha]_D^{25} = +136.935°$ ($CH_2Cl_2$, c=1.24 g.)

N.M.R. ($CDCl_3$): 0.75 (1H multiplet) 1.14 (1H multiplet) 1.49 (1H multiplet) 2.48 (2H multiplet) 3.76 (3H singlet) 4.1 (1H broad singlet) 5.1 (1H multiplet) 5.89 (1H doublet of a doublet, $J_1=10.5$ Hz. $J_2=10$ Hz.) 6.7 (1H doublet, $J=10.5$ Hz.) 7.09–7.73 (SH multiplet)

I.R. ($CH_2Cl_2$): 3604, 3084, 3026, 2930, 1739, 1364 and 1224 cm.$^{-1}$ and others

EXAMPLE 13

(E) -Trans-6S-[2'-[3''-(4'''-fluorophenyl)-1''-(1'''-methylethyl)indol-2''-yl]ethenyl]-4R-hydroxy-3,4,5,6-tetrahydro-2H-pyran-2-one

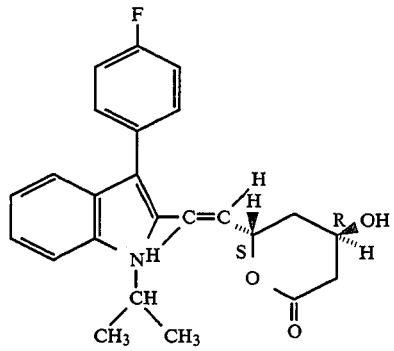
(LXIV)

The product may be obtained from Compounds XLIV and LVII by the processes of Steps 1–8 of Example 10. $[\alpha]_D^{25}=-25.3°$ (CHCl$_3$, c=0.12 g.). M.p. 147°–151° C.

EXAMPLE 14

Sodium erythro-(E)-3R,5S-dihydroxy-7-[3'-(4''-fluorophenyl)-1'-(1''-methylethyl)indol-2'-yl]hept-6-enoate

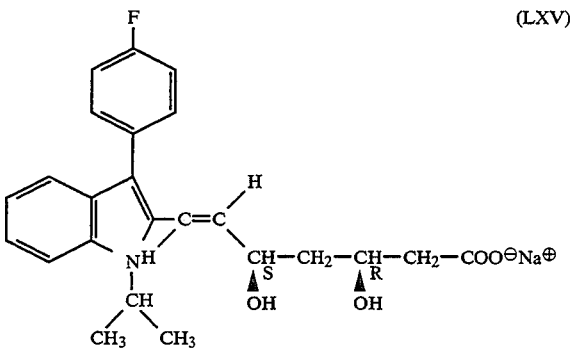
(LXV)

The product may be obtained from Compound LXIV by the process of Example 8 or Example 9. $[\alpha]_D^{25}=-16.4°$ (CHCl$_3$, c=0.58 g.) $[\alpha]_D^{22}=+23.8°\pm0.6°$ (CH$_3$OH, c=0.4 g.). M.p. 181°–182° C. (dec.)

EXAMPLE 14A

Ethyl erythro-(±)-(E)-3,5-dihydroxy-7-[3'-(3'',5''-dimethylphenyl)-1'-(1''-methylethyl)indol-2'-yl]hept-6-enoate

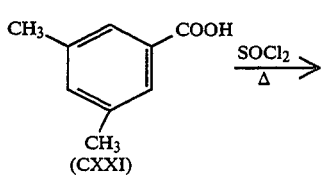
(CXXI)

-continued

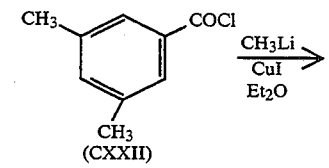
(CXXII)

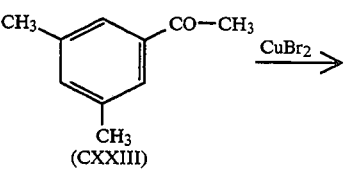
(CXXIII)

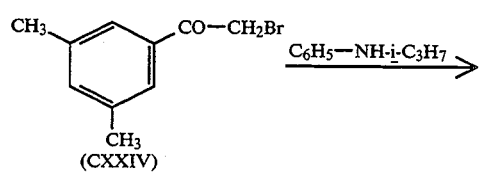
(CXXIV)

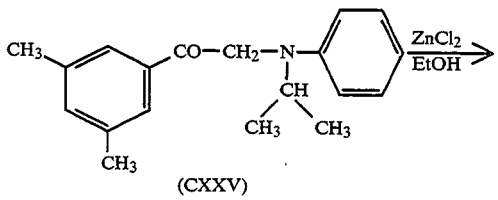
(CXXV)

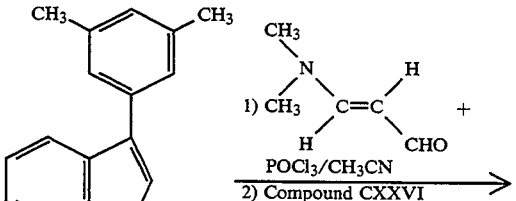
(CXXVI)

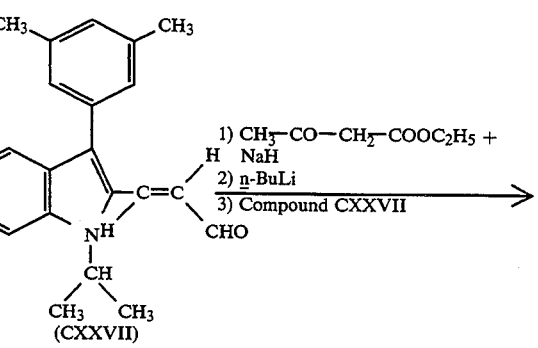
(CXXVII)

-continued

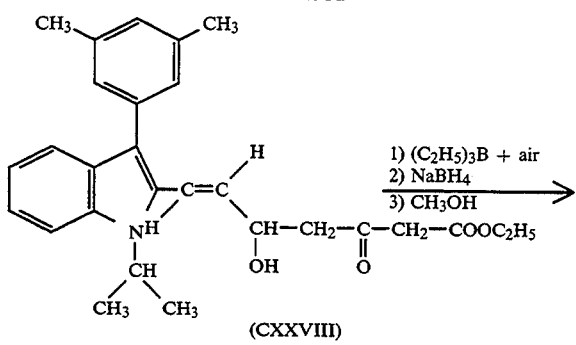

(CXXVIII)

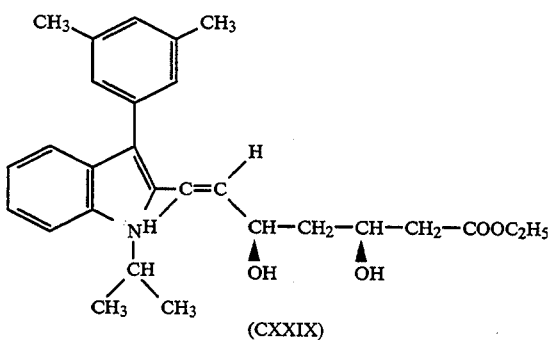

(CXXIX)

STEP 1

3,5-Dimethylbenzoyl chloride (Compound CXXII)

2.0 kg. (16.3 moles) of thionyl chloride is added dropwise over a period of 45 minutes to a suspension of 2.0 kg. (13.32 moles) of 3,5-dimethylbenzoic acid in 8 l. of toluene stirred at 65° C. under nitrogen during the course of which the temperature is kept below 80° C. The reaction mixture is stirred at 110°–115° C. under nitrogen for 5 hours and cooled, and the toluene and excess thionyl chloride are vacuum distilled at 55°–60° C. to obtain 2.247 kg. of crude product. A small sample is purified by vacuum distillation. B.p. 52°–57° C./0.25 mm Hg.

STEP 2

3,5-Dimethylacetophenone (Compound CXXIII)

145 g. (0.41 mole) of tris (acetylacetonato) iron (III) is added to a solution of 2.247 kg. (≦13.32 moles) of crude Compound CXXII containing some residual toluene (from Step 1) in 4.0 l. of dry tetrahydrofuran (dried over 3 Å. molecular sieves) at 20°–25° C., the reaction mixture is cooled to −15° C. with stirring under nitrogen, a solution of 1.096 kg. (14.65 moles) of methylmagnesium chloride in tetrahydrofuran (2.9M.) is added over a 2.5 hour period at a rate such that the temperature of the reaction mixture does not exceed 0° C. with stirring under nitrogen, and the reaction mixture is stirred at −10°–0° C. for 2 hours under nitrogen and quenched by portionwise siphoning into a mixture of 3 l. of saturated ammonium chloride solution and 250 ml. of concentrated (12M.) hydrochloric acid precooled to 5° C. The reaction vessel is washed sequentially with 1 l. of saturated ammonium chloride solution and 1 l. of tetrahydrofuran, the washes are combined with the reaction mixture, and the organic phase is separated. The aqueous phase is washed with 1 l. of tetrahydrofuran, and the washing is combined with the organic phase. The combined organic solution is washed with 2 l. of saturated sodium chloride solution, dried over 2.0 kg. of anhydrous sodium sulfate and filtered. The filter pad is washed three times with 500 ml. portions of tetrahydrofuran, the washings are added to the filtrate, and the solvent is evaporated at reduced pressure and 45° C. The resulting red oil is fractionally vacuum distilled through a 15 cm. Vigreux column to yield the 98.74% pure product as a colorless oil (896 g.). B.p. 68°–69° C./0.65 mm. Hg. Also obtained is 232 g. of 86.8% pure product. B.p. 60°–68° C./0.65 mm. Hg. Total yield, Steps 1 and 2, 55%.

STEP 3

1-Bromoacetyl-3,5-dimethylbenzene (Compound CXXIV)

A solution of 468 g. (2.93 moles) of bromine in 800 ml. of dichloromethane is added dropwise over a period of 3 hours to a mixture of 400 g. (2.664 moles) of Compound CXXIII and 2 l. of dichloromethane stirred at 20°–25° C. under nitrogen. The reaction mixture is stirred at 20°–25° C. under nitrogen for 2 hours, and the solvent is distilled at 40°–45° C. and reduced pressure to obtain the crude product as an oil (662 g.). A small sample is purified by vacuum distillation. B.p. 91°–98° C./0.1 mm. Hg.

STEP 4

N-(3,5-Dimethylbenzoylmethyl)-N-(1-methylethyl)aniline (Compound CXXV)

720 g. (5.33 moles) of N-isopropylaniline is added in one portion to a solution of 662 g. (≦2.664 moles) of crude Compound CXXIV (from Step 3) in 2.0 l. of isopropanol stirred at 50° C. under nitrogen, the reaction mixture is refluxed under nitrogen for 5 hours and cooled to 20°–25° C., 2 l. of dichloromethane and 6 l. of water are added sequentially, the two phase mixture is stirred for 5 minutes and the organic phase is separated. The solvent is distilled at 40°–45° C. and reduced pressure, and 1.0 l. of absolute ethanol is added to the resulting green oil with stirring. The mixture is cooled to 0° C. and maintained at that temperature for 15 minutes, the solids are collected by filtration, washed twice with 200 ml. portions of ice-cold absolute ethanol and vacuum dried at 45° C. for 3 hours to obtain the bright yellow product (445 g.), m.p. 95°–96° C. Yield, Steps 3 and 4, 59.4%.

N-isopropylaniline is synthesized as follows: A mixture of 233 g. (2.5 moles) of aniline, 5 l. of tetrahydrofuran and 250 ml. of acetone is stirred at 24°–25° C. under nitrogen for 2 hours and coooled to 10° C., 675 g. (4.06 moles) of phthalic acid is added rapidly, the resulting suspension is stirred at 10° C. under nitrogen, and 100 g. (2.64 moles) of powdered 98% sodium borohydride is added over a period of 25 minutes with stirring under nitrogen, during the course of which the temperature rises to 28° C. The reaction mixture is stirred under nitrogen at 28° C. for 15 minutes and at 60°–61° C. for 2 hours, cooled to 25° C. and siphoned portionwise into 2.0 l. of 20% sodium hydroxide solution at a rate such that the temperature does not exceed 20° C. The organic phase is separated, 1.0 kg. of anhydrous potassium carbonate is added, the mixture is stirred at 20°–25° C. for 20 minutes, the solid is removed by filtration and washed twice with 250 ml. portions of tetrahydrofuran, the washings are combined with the filtrate, and the tetrahydrofuran is distilled at 20-100 mm. Hg. and a maximum temperature of 55° C. The resulting residual oil is fractionally distilled through a 35 cm. Vigreux column to obtain the 97.4% pure product (295 g. (84.4%)). B.p. 62°–64° C./1 mm. Hg.

STEP 5

3-(3',5'-Dimethylphenyl)-1-(1'-methylethyl)indole (Compound CXXVI)

1.90 kg. (13.94 moles) of granulated anhydrous zinc chloride is added rapidly to 3.85 l. of n-propanol initially stirred at 20°–25° C. under nitrogen at a rate such that the internal temperature does not exceed 55° C. (the addition being exothermic), the mixture is stirred under nitrogen until a clear solution is obtained, 560 g. (1.99 moles) of Compound CXXV is added in one portion, and the reaction mixture is refluxed under nitrogen for 4 hours, cooled to 20°–25° C. and quenched with 5.9 l. of 1N. hydrochloric acid (5.9 equivalents). 1.48 l. of methylene chloride is added, the two phase system is mixed for 5 minutes, and the organic phase is separated, washed with 3 l. of water, washed with 3 l. of 15% ammonium hydroxide solution, washed with 3 l. of saturated sodium chloride solution and concentrated at 50° C. and reduced pressure to a volume of about 600 ml. 1.8 l. of isopropanol is added, and the solution is concentrated at 50° C. and reduced pressure to a volume of about 1.5 l., allowed to cool to 20°–25° C. with stirring, seeded with a few crystals obtained from a previous batch and allowed to slowly crystallize with stirring. The solid is collected by filtration, washed three times with 200 ml. portions of ice-cold isopropanol and vacuum dried at 20°–25° C. to constant weight (about 12 hours) to obtain the 98.8% pure product as a tan solid (357 g. (67.3%)), m.p. 60°–62° C.

Seed crystals may be obtained by drying a small portion of the isopropanol solution over anhydrous magnesium sulfate, evaporating the solution to dryness, flash chromatographing the residue on 230–400 mesh silica gel utilizing 1:1 (by volume) methyl t-butyl ether/n-hexane as the eluant, combining the fractions containing the product and evaporating them to dryness and recrystallizing the residue from absolute ethanol to obtain the white crystalline product. M.p. 64°–65° C.

STEP 6 (REACTION AA)

(E)-3-[3'-(3'',5''-Dimethylphenyl)-1'-(1''-methylethyl)indol-2'-yl]prop-2-enal (Compound CXXVII)

16.6 ml. (167 mmoles) of 3-dimethylaminoacrolein is slowly added to a solution of 15.5 ml. (167 mmoles) of phosphorus oxychloride in 100 ml. of acetonitrile stirred at −5° C. under nitrogen, the temperature of the reaction mixture being maintained at −5°–0° C. The reaction mixture is stirred at 0° C. for 30 minutes, the cooling bath is removed, a solution of 11.0 g. (41.8 mmoles) of Compound CXXVI in 125 ml. of acetonitrile is quickly added dropwise during the course of which the reaction mixture is heated to reflux, and the reaction mixture is refluxed for 16 hours and allowed to cool to 20°–25° C., the reaction mixture being stirred under nitrogen throughout. The reaction mixture is poured into a mixture of 75–100 ml. of 2N. sodium hydroxide solution and 200 ml. of ice (the mixture must be basic), and the mixture is extracted three times with diethyl ether. The diethyl ether extracts are combined, washed three times with water, dried over anhydrous magnesium sulfate, filtered and evaporated at reduced pressure. The residue is flash chromatographed on 230–400 mesh silica gel utilizing methylene chloride as the eluant, the fractions containing the product are combined and evaporated at reduced pressure, and the residue is recrystallized from n-hexane to obtain the product as yellow crystals (9.1 g.). M.p. 121°–123° C.

STEP 7 (REACTION A)

Ethyl(±)-(E)-7-[3'-(3'',5''-dimethylphenyl)-1'-(1''-methylethyl)indol-2'-yl]-5-hydroxy-3-oxohept-6enoate (Compound CXXVIII)

0.86 g. of 60% sodium hydride/mineral oil (21.5 mmoles) is rinsed with hexane, the sodium hydride is dried and suspended in 100 ml. of dry tetrahydrofuran, the suspension is cooled to 0° C., 2.7 ml. (21.2 mmoles) of ethyl acetoacetate is added dropwise with stirring at 0° C., the reaction mixture is stirred at 0° C. for 20 minutes, 13.0 ml. of 1.65M. n-butyllithium/hexane (21.4 mmoles) is added dropwise slowly with stirring at 0° C., the reaction mixture is stirred at 0° C. for 20 minutes and cooled to −78° C., a solution of 4.0 g. (12.6 mmoles) of Compound CXXVII in 100 ml. of dry tetrahydrofuran is rapidly added dropwise with stirring at −78° C., and the reaction mixture is stirred at −78° C. for 1 hour, the reaction mixture being stirred under nitrogen throughout. The reaction mixture is quenched at −78° C. with sufficient 2N. hydrochloric acid to give a pH of 4, sufficient water is added to dissolve all of the solids (about 150 ml.), and the mixture is extracted twice with diethyl ether. The diethyl ether extracts are combined, washed three to five times with saturated sodium chloride solution (until the washing is neutral), dried over anhydrous magnesium sulfate, filtered and evaporated at reduced pressure to obtain the crude product as a yellow oil (5.5 g.).

The product is a racemate that may be resolved to obtain the 5R and 5S enantiomers.

STEP 8 (REACTION B)

Ethyl erythro-(±)-(E)-3,5-dihydroxy-7-[3'-(3'',5''-dimethylphenyl)-1'-(1''-methylethyl)indol-2'-yl]hept-6-enoate (Compound CXXIX)

(a) 15.1 ml. of 1M. triethylborane/tetrahydrofuran (15.1 mmoles) is added dropwise to a solution of 5.5 g. (≦12.3 mmoles) of crude Compound CXXVIII from Step 7 in 100 ml. of dry tetrahydrofuran stirred at 20°–25° C., 20 ml. of air (at 760 mm. Hg. and 20°–25° C.) is added via syringe, the reaction mixture is stirred at 20°–25° C. for 1 hour and cooled to −78° C., 0.72 g. (18.9 mmoles) of sodium borohydride is added in one portion with stirring at −78° C., and the reaction mixture is stirred at −78° C. for 4 hours and allowed to warm to −20° C., the reaction mixture being maintained under nitrogen throughout. The reaction mixture is acidified to pH 6 with 2N. hydrochloric acid at −20° C. and extracted twice with diethyl ether. The diethyl ether extracts are combined, washed three times with saturated sodium chloride solution, dried over anhydrous magnesium sulfate, filtered and evaporated at reduced pressure to obtain the crude cyclic ethylborate ester as a yellow-orange oil (6 g.).

(b) A solution of the crude product of Part (a) in 150 ml. of HPLC grade methanol is stirred at 20°–25° C. under nitrogen for 3.5 hours and evaporated at reduced pressure, and the residue is dissolved in diethyl ether. The diethyl ether solution is washed twice with saturated sodium chloride solution, dried over anhydrous magnesium sulfate, filtered and evaporated at reduced pressure. The residue is flash chromatographed on 230–400 mesh silica gel utilizing 2:1 (by volume) methyl t-butyl ether/n-hexane as the eluant. The fractions containing the product are combined and evaporated at reduced pressure to obtain the product as a yellow-orange foam (5.06 g.).

The product is a racemate which may be resolved into two optically pure enantiomers, the 3R,5S and 3S,5R isomers of which the former is preferred. It contains a small amount of the corresponding threo racemate which may be separated therefrom and resolved to obtain the 3R,5R and 3S,5S enantiomers.

N.M.R. (CDCl₃): 1.37 (3H triplet) 1.54 (2H multiplet) 1.65 (6H doublet) 2.31 (6H singlet) 2.46 (2H doublet) 3.48 (1H singlet (slightly split)) 3.75 (1H singlet (slightly split)) 4.17 (2H quartet) 4.24 (1H multiplet) 4.49 (1H multiplet) 4.85 (1H quintet) 5.71 (1H doublet of a doublet) 6.68 (1H doublet) 6.88 (1H singlet) 7.00–7.34 (4H multiplet) 7.55 (2H doublet of a doublet).

EXAMPLE 14B

Erythro-(±)-(E)-3,5-dihydroxy-7-[3'-(3'',5''-dimethylphenyl)-1'-(1'''-methylethyl)indol-2'-yl]hept-6-enoic acid

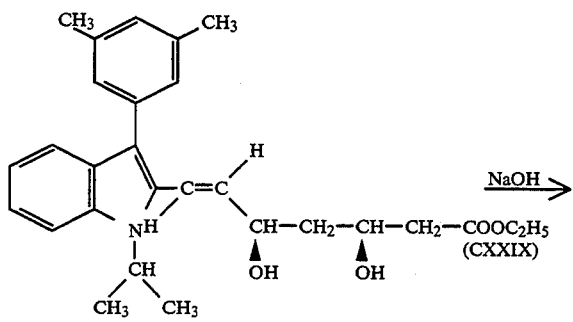

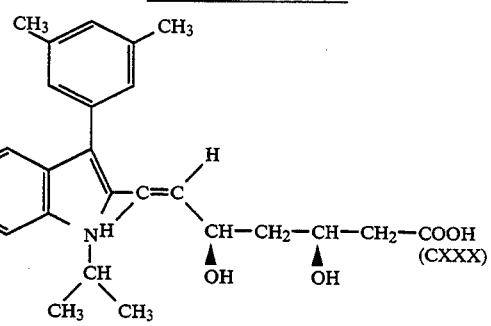

27.8 ml. of 1N, sodium hydroxide solution (27.8 moles) is added dropwise rapidly to a solution of 11.0 g. (25.3 mmoles) of Compound CXXIX in 200 ml. of HPLC grade methanol stirred under nitrogen at 20°–25° C., and the reaction mixture is stirred at 20°–25° C. under nitrogen for 1.5 hours and evaporated at reduced pressure. Sufficient water is added to dissolve most of the resulting orange oil, and the mixture is acidified to pH 2 with 2N. hydrochloric acid. The solution is extracted three times with diethyl ether, and the extracts are combined, washed three to five times with saturated sodium chloride solution (until the washing is neutral), dried over anhydrous magnesium sulfate and evaporated at reduced pressure to obtain the product as an orange foam (8.3 g.).

The product is a racemate which may be resolved into two optically pure enantiomers, the 3R,5S and 3S,5R isomers, of which the former is preferred. It contains a small amount of the corresponding threo racemate which may be separated therefrom and resolved to obtain the 3R,5R and 3S,5S enantiomers.

N.M.R. (CDCl₃): 1.56 (2H multiplet) 1.66 (6H doublet) 2.35 (6H singlet) 2.53 (2It doublet) 4.25 (1H multiplet) 4.50 (1H multiplet) 4.84 (1H quintet) 5.72 (1doublet of a doublet) 6.68 (1H doublet) 6.89 (1H singlet) 6.98–7.22 (4H multiplet) 7.55 (2H doublet of a doublet)

EXAMPLE 14C (E)-(±)-Trans-6-[2'-[3''-(3''',5'''-dimethylphenyl)-1''-(1'''indol-2''-yl]ethenyl]-4-hydroxy-3,4,5,6-tetrahydro-2H-pyran-2-one

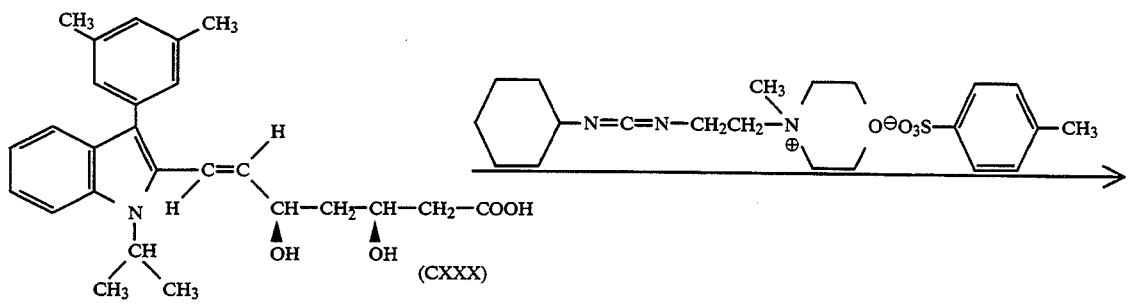

-continued
(Reaction E)

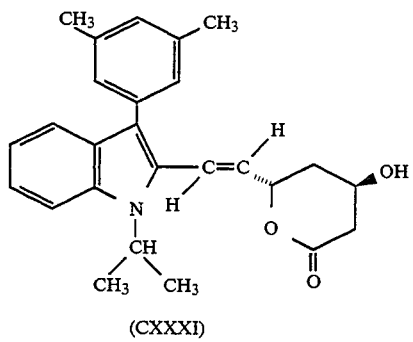

(CXXXI)

8.71 g. (20.7 mmoles) of N-cyclohexyl-N'-[2-(N"-methylmorpholinium)ethyl]carbodiimide p-toluenesulfonate is added to a solution of 8.3 g. (19.7 mmoles) of Compound CXXX in 200 ml. of HPLC grade methylene chloride stirred at 20°–25° C., and the reaction mixture is stirred at 20°–25° C. under nitrogen for 2 hours and extracted with 150 ml. of water. The methylene chloride phase is separated, and the aqueous phase is extracted twice with methylene chloride. The three methylene chloride phases are combined, washed twice with water, dried over anhydrous magnesium sulfate, filtered and evaporated at reduced pressure. The residue is flash chromatographed on 230–400 mesh silica gel utilizing 7:2:1 (by volume) methyl t-butyl ether/n-hexane/acetone as the eluant. The initial fractions which contain the racemic trans lactone are combined and evaporated at reduced pressure. The residue is triturated with n-hexane containing a trace of methyl t-butyl ether to obtain the product as a pale yellow powder (4.0 g.), m.p. 146°–149° C.

N.M.R. (CDCl$_3$): 1.65 (6H doublet) 1.70 (2H multiplet) 2.36 (6H singlet) 2.70 (2H multiplet) 4.30 (1H triplet) 4.83 (1H quintet) 5.25 (1H multiplet) 5.70 (1H doublet of a doublet) 6.75 (1H doublet) 6.9–7.6 (7H multiplet) 6.9–7.6 (7H multiplet)

The product is a racemate that may be resolved by, for example, the process set forth above into two optically pure enantiomers, the 4R,6S and 4S,6R isomers, of which the former is preferred.

EXAMPLE 14D

Sodium erythro-(±)-(E)-3,5-dihydroxy-7-[3'-(3",5"-dimethylphenyl)-1'-(1"-methylethyl)indol-2'-yl]hept-6-enoate (Reaction EE)

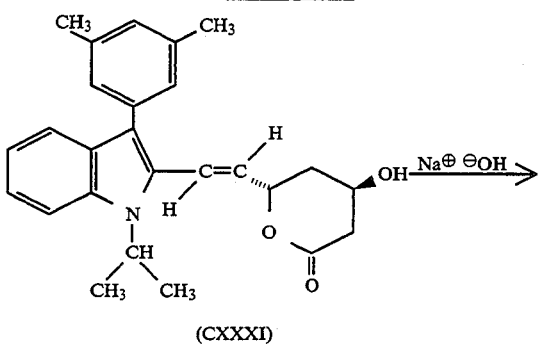

(CXXXI)

-continued
(Reaction EE)

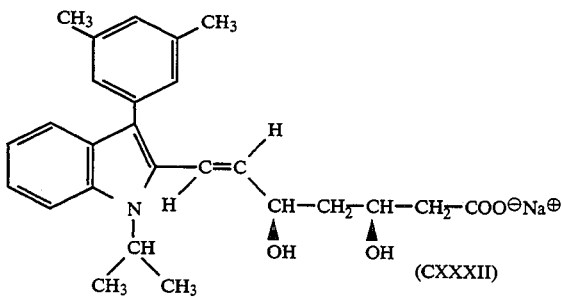

(CXXXII)

7.0 ml. of 1N. sodium hydroxide solution (7 mmoles) is added to a solution of 2.95 g. (7.32 mmoles) of Compound CXXXI in 100 ml. of absolute ethanol stirred at 20°–25° C., the reaction mixture is stirred at 20°14 25° C. under nitrogen for 1 hour and evaporated at reduced pressure, and the residue is dissolved in the minimum amount of water. The solution is gently washed with diethyl ether, subjected to reduced pressure for 5 minutes to remove the traces of diethyl ether and vacuum freeze-dried for 16 hours to obtain the product as a pale yellow power (3.1 g.), m.p. 183°–186° C.

N.M.R. (CD$_3$OD/CDCl$_3$): 1.52 (2H multiplet) 1.67 (6H doublet) 2.23 (2H multiplet) 2.34 (6H singlet) 3.35 (1H multiplet) 4.08 (1H multiplet) 4.90 (1H quintet) 5.75 (1H doublet of a doublet) 6.67 (1H doublet) 6.9–7.6 (7H multiplet)

The product is a racemate that may be resolved by conventional means to obtain the 3R,5S and 3S,5R enantiomers, of which the former is preferred.

TABLE I

Examples 15–82 and 143–165
The following compound of Group IAa may be synthesized by the processes set forth above:

| | R₁ | R₂ | R₃ | R₄ | R₅ | R₅ₐ | X | R₆ | R₇ | m.p. | Isomer(s) |
|---|---|---|---|---|---|---|---|---|---|---|---|
| Ex. 15 | CH₃ | H | H | H | H | H | \C=C/ (H,H / H,—) | H | CH₃ | | D |
| Ex. 16 | CH₃ | H | H | H | H | H | \C=C/ | H | C₂H₅ | Viscous oil | D |
| Ex. 17 | CH₃ | H | H | H | H | H | \C=C/ | H | Na | | D |
| Ex. 18 | CH₃ | H | H | H | H | H | \C=C/ | H | H | | D |
| Ex. 19 | CH₃ | H | H | H | H | H | \C=C/ | H | Na | Amorphous solid | E |
| Ex. 20 | CH₃ | H | H | H | H | H | \C=C/ | H | Na | Amorphous solid | T |
| Ex. 21 | CH₃ | 6-OCH₂C₆H₅ | H | 4-F | H | H | \C=C/ | H | C₂H₅ | Solid foam | D |
| Ex. 22 | CH₃ | 6-OCH₂C₆H₅ | H | 4-F | H | H | \C=C/ | H | K | | D |
| Ex. 23 | CH₃ | 6-OCH₂C₆H₅ | H | 4-F | H | H | \C=C/ | H | Na | Amorphous solid | D |
| Ex. 24 | CH₃ | 6-OCH₂C₆H₅ | H | 4-F | H | H | \C=C/ | H | H | | D |
| Ex. 25 | CH₃ | H | H | 4-F | H | H | DB | H | CH₃ | | D |
| Ex. 26 | CH₃ | H | H | 4-F | H | H | DB | H | Na | | D |
| Ex. 27 | CH₃ | H | H | 4-F | H | H | DB | H | H | | D |
| Ex. 28 | CH₃ | H | H | 3-CH₃ | 4-CH₃ | H | \C=C/ | H | C₂H₅ | Oil | D |
| Ex. 29 | CH₃ | H | H | 3-CH₃ | 4-CH₃ | H | \C=C/ | H | K | | D |
| Ex. 30 | CH₃ | H | H | 3-CH₃ | 4-CH₃ | H | \C=C/ | H | H | | D |

TABLE I-continued

Examples 15–82 and 143–165
The following compound of Group IAa may be synthesized by the processes set forth above:

| | R₁ | R₂ | R₃ | R₄ | R₅ | R₅ₐ | X | R₆ | R₇ | m.p. | Isomer(s) |
|---|---|---|---|---|---|---|---|---|---|---|---|
| Ex. 31 | i-C₃H₇ | H | H | 4-F | H | H | \C=C/ (H,H / H) | H | C₂H₅ | | D |
| Ex. 32 | i-C₃H₇ | H | H | 4-F | H | H | \C=C/ | H | CH₃ | Viscous oil | D |
| Ex. 33 | i-C₃H₇ | H | H | 4-F | H | H | \C=C/ | H | K | | D |
| Ex. 34 | i-C₃H₇ | H | H | 4-F | H | H | \C=C/ | H | H | | D |
| Ex. 35 | CH₃ | 4-OCH₂C₆H₅ | H | 4-F | H | H | \C=C/ | H | C₂H₅ | Viscous oil | D |
| Ex. 36 | CH₃ | 4-OCH₂C₆H₅ | H | 4-F | H | H | \C=C/ | H | K | | D |
| Ex. 37 | CH₃ | 4-OCH₂C₆H₅ | H | 4-F | H | H | \C=C/ | H | H | | D |
| Ex. 38 | CH₃ | H | H | 3-CH₃ | 5-CH₃ | H | \C=C/ | H | C₂H₅ | Viscous oil | D |
| Ex. 39 | CH₃ | H | H | 3-CH₃ | 5-CH₃ | H | \C=C/ | H | K | | D |
| Ex. 40 | CH₃ | H | H | 3-CH₃ | 5-CH₃ | H | \C=C/ | H | H | | D |
| Ex. 41 | CH₃ | H | H | 3-CH₃ | 5-CH₃ | H | \C=C/ | H | Na | Amorphous solid | E |
| Ex. 42 | CH₃ | H | H | 3-CH₃ | 5-CH₃ | H | \C=C/ | H | Na | Amorphous solid | T |
| Ex. 43 | CH₃ | 5-Cl | H | 4-F | H | H | \C=C/ | H | C₂H₅ | 96°–105° C. | D |
| Ex. 44 | CH₃ | 5-Cl | H | 4-F | H | H | \C=C/ | H | K | | D |

TABLE I-continued

Examples 15–82 and 143–165
The following compound of Group IAa may be synthesized by the processes set forth above:

| | R₁ | R₂ | R₃ | R₄ | R₅ | R₅ₐ | X | R₆ | R₇ | m.p. | Isomer(s) |
|---|---|---|---|---|---|---|---|---|---|---|---|
| Ex. 45 | CH₃ | 5-Cl | H | 4-F | H | H | CH=CH | H | H | | D |
| Ex. 46 | CH₃ | 5-OCH₃ | H | 4-F | H | H | CH=CH | H | C₂H₅ | Viscous oil | D |
| Ex. 47 | CH₃ | 5-OCH₃ | H | 4-F | H | H | CH=CH | H | Na | | D |
| Ex. 48 | CH₃ | 5-OCH₃ | H | 4-F | H | H | CH=CH | H | H | | D |
| Ex. 49 | CH₃ | H | H | 4-F | H | H | CH=CH | H | Na | 193°–196° C. (dec.) | E |
| Ex. 50 | CH₃ | 7-OCH₂C₆H₅ | H | 4-F | H | H | CH=CH | H | C₂H₅ | 78°–82° C. | D |
| Ex. 51 | CH₃ | 7-OCH₂C₆H₅ | H | 4-F | H | H | CH=CH | H | Na | | D |
| Ex. 52 | CH₃ | 7-OCH₂C₆H₅ | H | 4-F | H | H | CH=CH | H | H | | D |
| Ex. 53 | CH₃ | 7-OCH₂C₆H₅ | H | 4-F | H | H | CH=CH | H | Na | Amorphous solid | E |
| Ex. 54 | CH₃ | 7-OCH₂C₆H₅ | H | 4-F | H | H | CH=CH | H | Na | Amorphous solid | T |
| Ex. 55 | CH₃ | 5-OCH₂C₆H₅ | H | 4-F | H | H | CH=CH | H | C₂H₅ | Viscous oil | D |
| Ex. 56 | CH₃ | 5-OCH₂C₆H₅ | H | 4-F | H | H | CH=CH | H | Na | | D |
| Ex. 57 | CH₃ | 5-OCH₂C₆H₅ | H | 4-F | H | H | CH=CH | H | H | | D |
| Ex. 58 | C₆H₅—CH₂CH₂— | H | H | 4-F | H | H | CH=CH | H | CH₃ | Oil | D |

TABLE I-continued

Examples 15–82 and 143–165
The following compound of Group IAa may be synthesized by the processes set forth above:

| | R₁ | R₂ | R₃ | R₄ | R₅ | R₅ₐ | X | R₆ | R₇ | m.p. | Isomer(s) |
|---|---|---|---|---|---|---|---|---|---|---|---|
| Ex. 59 | C₆H₅—CH₂CH₂— | H | H | 4-F | H | H | \C=C/ (H,H) | H | Na | Amorphous solid | E |
| Ex. 60 | C₂H₅ | H | H | 4-F | H | H | \C=C/ | H | C₂H₅ | Viscous oil | D |
| Ex. 61 | C₂H₅ | H | H | 4-F | H | H | \C=C/ | H | Na | Amorphous solid | E |
| Ex. 62 | C₂H₅ | H | H | 4-F | H | H | \C=C/ | H | Na | Amorphous solid | T |
| Ex. 63 | i-C₃H₇ | 4-CH₃ | 6-CH₃ | 4-F | H | H | \C=C/ | H | C₂H₅ | 107°–110° C. | D |
| Ex. 64 | i-C₃H₇ | 4-CH₃ | 6-CH₃ | 4-F | H | H | \C=C/ | H | Na | Solid foam | E |
| Ex. 65 | i-C₃H₇ | 4-CH₃ | 6-CH₃ | 4-F | H | H | \C=C/ | H | H | | E |
| Ex. 66 | i-C₃H₇ | 4-CH₃ | 6-CH₃ | 4-F | H | H | \C=C/ | H | Na | Solid foam | T |
| Ex. 67 | i-C₃H₇ | H | H | 3-CH₃ | 5-CH₃ | H | \C=C/ | H | CH₃ | Viscous oil | D E:T = ~3:2 |
| Ex. 68 | i-C₃H₇ | H | H | 3-CH₃ | 5-CH₃ | H | \C=C/ | H | Na | 183°–186° C. | E Same as Ex. 14D |
| Ex. 69 | i-C₃H₇ | 5-cyclo-hexyl | H | 4-F | H | H | \C=C/ | H | CH₃ | Viscous oil | D |
| Ex. 70 | i-C₃H₇ | 5-cyclo-hexyl | H | 4-F | H | H | \C=C/ | H | Na | Solid foam | E |
| Ex. 71 | i-C₃H₇ | 5-cyclo-hexyl | H | 4-F | H | H | \C=C/ | H | Na | Solid foam | T |
| Ex. 72 | cyclohexyl | H | H | 4-F | H | H | \C=C/ | H | CH₃ | Solid foam | D |

TABLE I-continued

Examples 15–82 and 143–165
The following compound of Group IAa may be synthesized by the processes set forth above:

| | R₁ | R₂ | R₃ | R₄ | R₅ | R₅ₐ | X | R₆ | R₇ | m.p. | Isomer(s) |
|---|---|---|---|---|---|---|---|---|---|---|---|
| Ex. 73 | cyclohexyl | H | H | 4-F | H | H | CH=CH (H,H) | H | Na | Amorphous solid | E |
| Ex. 74 | cyclohexyl | H | H | 4-F | H | H | CH=CH (H,H) | H | Na | Amorphous solid | T |
| Ex. 75 | i-C₃H₇ | 6-OCH₂C₆H₅ | H | 4-F | H | H | CH=CH (H,H) | H | C₂H₅ | Solid foam | D |
| Ex. 76 | i-C₃H₇ | H | H | 3-CH₃ | 4-F | 5-CH₃ | CH=CH (H,H) | H | C₂H₅ | Viscous oil | D |
| Ex. 77 | i-C₃H₇ | H | H | 2-CH₃ | H | H | CH=CH (H,H) | H | Na | Amorphous solid | E |
| Ex. 78 | i-C₃H₇ | H | H | 2-CH₃ | H | H | CH=CH (H,H) | H | Na | Amorphous solid | T |
| Ex. 79 | i-C₃H₇ | H | H | 3-CH₃ | 4-F | H | CH=CH (H,H) | H | Na | Amorphous solid | E |
| Ex. 80 | i-C₃H₇ | H | H | 3-CH₃ | 4-F | H | CH=CH (H,H) | H | Na | Amorphous solid | T |
| Ex. 81 | i-C₃H₇ | H | H | 3-CH₃ | 4-F | 5-CH₃ | CH=CH (H,H) | H | Na | Amorphous solid | E |
| Ex. 82 | i-C₃H₇ | 6-OCH₂C₆H₅ | H | 4-F | H | H | CH=CH (H,H) | H | Na | 180°–182° C. (dec.) | E |
| Ex. 143 | i-C₄H₉ | H | H | 4-F | H | H | CH=CH (H,H) | H | Na | 140°–160° C. (dec.) | E |
| Ex. 144 | i-C₃H₇ | H | H | 2-CH₃ | 4-F | H | CH=CH (H,H) | H | CH₃ | Oil | D (E:T = ~4:1) |
| Ex. 145 | i-C₃H₇ | H | H | 2-CH₃ | 4-F | H | CH=CH (H,H) | H | Na | 155°–168° C. (dec.) | E |
| Ex. 146 | i-C₄H₉ | H | H | 4-F | H | H | CH=CH (H,H) | H | CH₃ | Solid foam | D (E:T = ~3:2) |

TABLE I-continued

Examples 15–82 and 143–165
The following compound of Group IAa may be synthesized by the processes set forth above:

| | $R_1$ | $R_2$ | $R_3$ | $R_4$ | $R_5$ | $R_{5a}$ | X | $R_6$ | $R_7$ | m.p. | Isomer(s) |
|---|---|---|---|---|---|---|---|---|---|---|---|
| Ex. 147 | i-$C_3H_7$ | 4-i-$C_3H_7$ | 6-i-$C_3H_7$ | 4-F | H | H | −CH=CH− | H | $C_2H_5$ | 123°–125° C. | E |
| Ex. 148 | i-$C_3H_7$ | H | H | 4-F | H | H | −CH=CH− | $CH_3$ | Na | Amorphous solid | D (T:E = ~4:1) |
| Ex. 149 | i-$C_3H_7$ | H | H | 4-F | H | H | −CH=CH− | $CH_3$ | Na | Amorphous solid | D (E:T = ~4:1) |
| Ex. 150 | i-$C_3H_7$ | H | H | 4-F | H | H | −CH=CH− | H | Na | Amorphous solid | 3R,5R |
| Ex. 151 | i-$C_3H_7$ | H | H | 4-F | H | H | −CH=CH− | H | Na | Amorphous solid | 3S,5R |
| Ex. 152 | i-$C_3H_7$ | H | H | 4-F | H | H | −CH=CH− | H | Na | Amorphous solid | 3S,5S |
| Ex. 153 | i-$C_3H_7$ | H | H | 4-F | H | H | −CH=CH− | H | Na | Amorphous solid | 3R,5S |
| Ex. 154 | i-$C_3H_7$ | 4-i-$C_3H_7$ | 6-i-$C_3H_7$ | 4-F | H | H | −CH=CH− | H | Na | >100° C. (dec.) | E |
| Ex. 155 | i-$C_3H_7$ | H | H | 4-$CF_3$ | H | H | −CH=CH− | H | $CH_3$ | Oil | E |
| Ex. 156 | i-$C_3H_7$ | H | H | 4-$CF_3$ | H | H | −CH=CH− | H | Na | Amorphous solid | E |
| Ex. 157 | $CH_3$ | H | H | 3-$CF_3$ | H | H | −CH=CH− | H | $C_2H_5$ | 88°–90° C. | D (E:T = ~4:1) |
| Ex. 158 | $CH_3$ | H | H | 3-$CF_3$ | H | H | −CH=CH− | H | Na | >100° C. (dec.) | E |
| Ex. 159 | i-$C_3H_7$ | H | H | 4-F | H | H | −$CH_2CH_2$− | H | Na | 182°–190° C. | E |
| Ex. 160 | i-$C_3H_7$ | 4-$CH_3$ | 6-$CH_3$ | 4-F | H | H | −CH=CH− | H | $CH_3$ | 112°–113° C. | E |

TABLE I-continued

Examples 15-82 and 143-165
The following compound of Group IAa may be synthesized by the processes set forth above:

| | $R_1$ | $R_2$ | $R_3$ | $R_4$ | $R_5$ | $R_{5a}$ | X | $R_6$ | $R_7$ | m.p. | Isomer(s) |
|---|---|---|---|---|---|---|---|---|---|---|---|
| Ex. 161 | $(C_2H_5)_2CH-$ | H | H | 4-F | H | H | $\begin{array}{c}\diagdown\phantom{C}\diagup H\\C{=}C\\\diagup\phantom{C}\diagdown\\H\end{array}$ | H | $C_2H_5$ | Oil | D (E:T = ~3:2) |
| Ex. 162 | i-$C_3H_7$ | H | H | 4-F | H | H | $-CH_2CH_2-$ | H | Na | Amorphous solid | 3R,5R |
| Ex. 163 | i-$C_3H_7$ | H | H | 4-F | H | H | $-CH_2CH_2CH_2-$ | H | Na | Solid foam | 3R,5R |
| Ex. 164 | i-$C_3H_7$ | H | H | H | H | H | $\begin{array}{c}\diagdown\phantom{C}\diagup H\\C{=}C\\\diagup\phantom{C}\diagdown\\H\end{array}$ | $CH_3$ | $CH_3$ | 118°–121° C. | E (~5% T) |
| Ex. 165 | i-$C_3H_7$ | H | H | H | H | H | $\begin{array}{c}\diagdown\phantom{C}\diagup H\\C{=}C\\\diagup\phantom{C}\diagdown\\H\end{array}$ | H | Na | >150° C. (dec.) | E (~5% T) |

TABLE II

Examples 83-122 and 166-178
The following compounds of Group IAb may be synthesized by the processes set forth above:

| | R₁ | R₂ | R₃ | R₄ | R₅ | R₅ₐ | X | R₆ | m.p. | Isomer(s) |
|---|---|---|---|---|---|---|---|---|---|---|
| Ex. 83 | CH₃ | H | H | H | H | H | >C=C< (H) | H | Solid foam | cis |
| Ex. 84 | CH₃ | H | H | H | H | H | >C=C< (H) | H | 119.5°–121° C. | trans |
| Ex. 85 | CH₃ | 6-OCH₂C₆H₅ | H | H | H | H | >C=C< (H) | H | 145°–146° C. | mixture: ~75% trans ~25% cis |
| Ex. 86 | CH₃ | 6-OCH₂C₆H₅ | H | 4-F | H | H | >C=C< (H) | H | | cis |
| Ex. 87 | CH₃ | 6-OCH₂C₆H₅ | H | 4-F | H | H | >C=C< (H) | H | | trans |
| Ex. 88 | CH₃ | H | H | 4-F | H | H | —CH₂CH₂— | H | 164°–169° C. (dec.) | cis |
| Ex. 89 | CH₃ | H | H | 4-F | H | H | —CH₂CH₂— | H | | trans |
| Ex. 90 | CH₃ | H | H | 3-CH₃ | 4-CH₃ | H | >C=C< (H) | H | Solid foam | cis |
| Ex. 91 | CH₃ | H | H | 3-CH₃ | 4-CH₃ | H | >C=C< (H) | H | Solid foam | trans |
| Ex. 92 | i-C₃H₇ | 4-CH₃ | 6-CH₃ | 4-F | H | H | >C=C< (H) | H | 150.5°–151° C. | ≧95% cis |

TABLE II-continued

Examples 83–122 and 166–178
The following compounds of Group IAb may be synthesized by the processes set forth above:

| | R$_1$ | R$_2$ | R$_3$ | R$_4$ | R$_5$ | R$_{5a}$ | X | R$_6$ | m.p. | Isomer(s) |
|---|---|---|---|---|---|---|---|---|---|---|
| Ex. 93 | i-C$_3$H$_7$ | 4-CH$_3$ | 6-CH$_3$ | 4-F | H | H | C=C(H)(H) | H | 146°–147° C. | trans |
| Ex. 94 | CH$_3$ | 4-OCH$_2$C$_6$H$_5$ | H | 4-F | H | H | C=C(H)(H) | H | | cis |
| Ex. 95 | CH$_3$ | 4-OCH$_2$C$_6$H$_5$ | H | 4-F | H | H | C=C(H)(H) | H | | trans |
| Ex. 96 | CH$_3$ | H | H | 3-CH$_3$ | 5-CH$_3$ | H | C=C(H)(H) | H | Solid foam | cis |
| Ex. 97 | CH$_3$ | H | H | 3-CH$_3$ | 5-CH$_3$ | H | C=C(H)(H) | H | Solid foam | trans |
| Ex. 98 | CH$_3$ | 5-Cl | H | 4-F | H | H | C=C(H)(H) | H | 165.5°–166° C. (dec.) | cis |
| Ex. 99 | CH$_3$ | 5-Cl | H | 4-F | H | H | C=C(H)(H) | H | 157.5°–159° C. | trans |
| Ex. 100 | CH$_3$ | 5-OCH$_3$ | H | 4-F | H | H | C=C(H)(H) | H | Solid foam | cis |
| Ex. 101 | CH$_3$ | 5-OCH$_3$ | H | 4-F | H | H | C=C(H)(H) | H | 102°–105° C. | trans |

TABLE II-continued

Examples 83-122 and 166-178

The following compounds of Group IAb may be synthesized by the processes set forth above:

| | $R_1$ | $R_2$ | $R_3$ | $R_4$ | $R_5$ | $R_{5a}$ | X | $R_6$ | m.p. | Isomer(s) |
|---|---|---|---|---|---|---|---|---|---|---|
| Ex. 102 | $CH_3$ | 7-$OCH_2C_6H_5$ | H | 4-F | H | H | -C(H)=C(H)- | H | 127°–128.5° C. | cis |
| Ex. 103 | $CH_3$ | 7-$OCH_2C_6H_5$ | H | 4-F | H | H | -C(H)=C(H)- | H | 140.5°–141.5° C. | trans |
| Ex. 104 | $CH_3$ | 5-$OCH_2C_6H_5$ | H | 4-F | H | H | -C(H)=C(H)- | H | 118°–119° C. | mixture: ~80% cis ~20% trans |
| Ex. 105 | $CH_3$ | 5-$OCH_2C_6H_5$ | H | 4-F | H | H | -C(H)=C(H)- | H | | cis |
| Ex. 106 | $CH_3$ | 5-$OCH_2C_6H_5$ | H | 4-F | H | H | -C(H)=C(H)- | H | 118°–119° C. | trans |
| Ex. 107 | $C_6H_5CH_2CH_2-$ | H | H | 4-F | H | H | -C(H)=C(H)- | H | Solid foam | cis |
| Ex. 108 | $C_6H_5CH_2CH_2-$ | H | H | 4-F | H | H | -C(H)=C(H)- | H | Solid foam | trans |
| Ex. 109 | i-$C_3H_7$ | H | H | 3-$CH_3$ | 5-$CH_3$ | H | -C(H)=C(H)- | H | 108°–110° C. | cis |
| Ex. 110 | i-$C_3H_7$ | H | H | 3-$CH_3$ | 5-$CH_3$ | H | -C(H)=C(H)- | H | 146°–149° C. | trans, Same as Ex. 14C |

TABLE II-continued

Examples 83–122 and 166–178
The following compounds of Group IAb may be synthesized by the processes set forth above:

| | R$_1$ | R$_2$ | R$_3$ | R$_4$ | R$_5$ | R$_{5a}$ | X | R$_6$ | m.p. | Isomer(s) |
|---|---|---|---|---|---|---|---|---|---|---|
| Ex. 111 | C$_2$H$_5$ | H | H | 4-F | H | H | C=C(H)(CH$_3$)(H) | H | 133.5°–135° C. | cis |
| Ex. 112 | C$_2$H$_5$ | H | H | 4-F | H | H | C=C(H)(CH$_3$)(H) | H | 136°–137° C. | trans |
| Ex. 113 | i-C$_3$H$_7$ | H | H | 3-CH$_3$ | 4-F | H | C=C(H)(CH$_3$)(H) | H | 120°–123° C. | cis |
| Ex. 114 | i-C$_3$H$_7$ | H | H | 3-CH$_3$ | 4-F | H | C=C(H)(CH$_3$)(H) | H | 140.5°–141.5° C. | trans |
| Ex. 115 | i-C$_3$H$_7$ | 5-cyclohexyl | H | 4-F | H | H | C=C(H)(CH$_3$)(H) | H | Solid foam | cis |
| Ex. 116 | i-C$_3$H$_7$ | 5-cyclohexyl | H | 4-F | H | H | C=C(H)(CH$_3$)(H) | H | 162°–166° C. | trans |
| Ex. 117 | cyclohexyl | H | H | 4-F | H | H | C=C(H)(CH$_3$)(H) | H | Solid foam | cis |
| Ex. 118 | cyclohexyl | H | H | 4-F | H | H | C=C(H)(CH$_3$)(H) | H | Solid foam | trans |
| Ex. 119 | i-C$_3$H$_7$ | H | H | 2-CH$_3$ | H | H | C=C(H)(CH$_3$)(H) | H | Solid foam | cis |

TABLE II-continued
Examples 83–122 and 166–178
The following compounds of Group IAb may be synthesized by the processes set forth above:

| | R₁ | R₂ | R₃ | R₄ | R₅ | R₅ₐ | X | R₆ | m.p. | Isomer(s) |
|---|---|---|---|---|---|---|---|---|---|---|
| Ex. 120 | i-C₃H₇ | H | H | 2-CH₃ | H | H | C=C(H)(H) | H | Solid foam | trans |
| Ex. 121 | i-C₃H₇ | H | H | 3-CH₃ | 4-F | H | C=C(H)(H) | H | 107°–113° C. | mixture: ~88% cis ~12% trans |
| Ex. 122 | i-C₃H₇ | H | H | 3-CH₃ | 4-F | 5-CH₃ | C=C(H)(H) | H | 166.5°–167.5° C. | trans |
| Ex. 166 | i-C₃H₇ | 6-OCH₂C₆H₅ | H | 4-F | H | 5-CH₃ | C=C(H)(H) | H | 152°–153° C. (dec.) | trans |
| Ex. 167 | i-C₄H₉ | H | H | 4-F | H | H | C=C(H)(H) | H | 51°–52° C. | trans |
| Ex. 168 | i-C₃H₇ | H | H | 2-CH₃ | 4-F | H | C=C(H)(H) | H | 64°–69° C. | trans |
| Ex. 169 | i-C₃H₇ | H | H | 4-F | H | H | C=C(H)(H) | CH₃ | Solid foam | mixture: ~80% trans ~20% cis |
| Ex. 170 | i-C₃H₇ | H | H | 4-F | H | H | C=C(H)(H) | CH₃ | Solid foam | mixture: ~80% cis ~20% trans |
| Ex. 171 | i-C₃H₇ | H | H | 4-F | H | H | C=C(H)(H) | H | 170°–174° C. | 4R,6R |

TABLE II-continued

Examples 83–122 and 166–178
The following compounds of Group IAb may be synthesized by the processes set forth above:

| | R₁ | R₂ | R₃ | R₄ | R₅ | R₅ₐ | X | R₆ | m.p. | Isomer(s) |
|---|---|---|---|---|---|---|---|---|---|---|
| Ex. 172 | i-C₃H₇ | H | H | 4-F | H | H | −CH=CH−CH₃ | H | 150°–151° C. | 4S,6R |
| Ex. 173 | i-C₃H₇ | H | H | 4-F | H | H | −CH=CH−CH₃ | H | 173°–176° C. | mixture: ~90% 4S,6S ~10% 4S,6R |
| Ex. 174 | i-C₃H₇ | H | H | 4-F | H | H | −CH=CH−CH₃ | H | Oil | 4R,6S |
| Ex. 175 | i-C₃H₇ | 4-i-C₃H₇ | 6-i-C₃H₇ | 4-F | H | H | −CH=CH−CH₃ | H | 142°–144° C. | trans |
| Ex. 176 | i-C₃H₇ | H | H | 4-CF₃ | H | H | −CH=CH−CH₃ | H | Solid foam | trans |
| Ex. 177 | CH₃ | H | H | 3-CF₃ | H | H | −CH=CH−CH₃ | H | 127°–128° C. | trans |
| Ex. 178 | i-C₃H₇ | H | H | 4-F | H | H | −CH₂CH₂CH₂− | H | Oil | 4R,6R |

TABLE III

Examples 123-134 and 179-182
The following compounds of Group IBa may be synthesized by the processes set forth above:

| | $R_1$ | $R_2$ | $R_3$ | $R_4$ | $R_5$ | $R_{5a}$ | X | $R_6$ | $R_7$ | m.p. | Isomer(s) |
|---|---|---|---|---|---|---|---|---|---|---|---|
| Ex. 123 | $CH_3$ | H | H | 4-F | H | H | -CH=CH- | H | $C_2H_5$ | | D |
| Ex. 124 | $CH_3$ | H | H | 4-F | H | H | -CH=CH- | H | K | | D |
| Ex. 125 | $CH_3$ | H | H | 4-F | H | H | -CH=CH- | H | H | | D |
| Ex. 126 | $C_2H_5$ | 5-$OCH_3$ | H | 3-$CH_3$ | H | H | $-CH_2CH_2-$ | $CH_3$ | $CH_3$ | | D |
| Ex. 127 | $C_2H_5$ | 5-$OCH_3$ | H | 3-$CH_3$ | H | H | $-CH_2CH_2-$ | $CH_3$ | K | | D |
| Ex. 128 | $C_2H_5$ | 5-$OCH_3$ | H | 3-$CH_3$ | H | H | $-CH_2CH_2-$ | $CH_3$ | H | | D |
| Ex. 129 | i-$C_3H_7$ | H | H | 4-F | H | H | -CH=CH- | H | $C_2H_5$ | | D |
| Ex. 130 | i-$C_3H_7$ | H | H | 4-F | H | H | -CH=CH- | H | K | | D |
| Ex. 131 | i-$C_3H_7$ | H | H | 4-F | H | H | -CH=CH- | H | H | | D |
| Ex. 132 | $CH_3$ | H | H | H | H | H | -CH=CH- | H | $C_2H_5$ | Viscous oil | D |
| Ex. 133 | $CH_3$ | H | H | H | H | H | -CH=CH- | H | Na | | D |
| Ex. 134 | $CH_3$ | H | H | H | H | H | -CH=CH- | H | H | | D |
| Ex. 179 | i-$C_3H_7$ | H | H | 4-F | H | H | -CH=CH- | H | $C_2H_5$ | Oil | D (E:T = ~3:2) |
| Ex. 180 | i-$C_3H_7$ | H | H | 4-F | H | H | -CH=CH- | H | $CH_3$ | 103°-104° C. | E |
| Ex. 181 | i-$C_3H_7$ | H | H | 4-F | H | H | -CH=CH- | H | Na | Amorphous solid | D (E:T = ~3:2) |

TABLE III-continued

Examples 123-134 and 179-182
The following compounds of Group IBa may be synthesized by the processes set forth above:

| | $R_1$ | $R_2$ | $R_3$ | $R_4$ | $R_5$ | $R_{5a}$ | X | $R_6$ | $R_7$ | m.p. | Isomer(s) |
|---|---|---|---|---|---|---|---|---|---|---|---|
| Ex. 182 | i-$C_3H_7$ | H | H | 4-F | H | H | \C=C/ with H's | H | H | Na | Amorphous solid | E |

TABLE IV

Examples 135-142
The following compounds of Group IBb may be synthesized by the processes set forth above:

| | $R_1$ | $R_2$ | $R_3$ | $R_4$ | $R_5$ | $R_{5a}$ | X | $R_6$ | m.p. | Isomer(s) |
|---|---|---|---|---|---|---|---|---|---|---|
| Ex. 135 | $CH_3$ | H | H | 4-F | H | H | \C=C/ | H | | cis |
| Ex. 136 | $CH_3$ | H | H | 4-F | H | H | \C=C/ | H | | trans |
| Ex. 137 | $C_2H_5$ | 5-$OCH_3$ | H | 3-$CH_3$ | H | H | —$CH_2CH_2$— | $CH_3$ | | cis |
| Ex. 138 | $C_2H_5$ | 5-$OCH_3$ | H | 3-$CH_3$ | H | H | —$CH_2CH_2$— | $CH_3$ | | trans |
| Ex. 138A | i-$C_3H_7$ | H | H | 4-F | H | H | \C=C/ | H | 130°-132° C. | mixture: ~60% trans ~40% cis |
| Ex. 139 | i-$C_3H_7$ | H | H | 4-F | H | H | \C=C/ | H | | cis |
| Ex. 140 | i-$C_3H_7$ | H | H | 4-F | H | H | \C=C/ | H | | trans |
| Ex. 141 | $CH_3$ | H | H | H | H | H | \C=C/ | H | Solid foam | cis |
| Ex. 142 | $CH_3$ | H | H | H | H | H | \C=C/ | H | Viscous oil | trans |

In Tables I-IV,
DB = direct bond
D = mixture of diastereoisomers (four stereoisomers)
E = erythro racemate (two stereoisomers)
T = threo racemate (two stereoisomers)

Each of the compounds of Tables I and III denoted by a D in the Isomer(s) column is a mixture of four stereoisomers which may be separated. The four optically pure enantiomers that may be obtained may be designated as the 3R,5R, 3S,5S, 3R,5S and 3S,5R isomers. Except in the case of Examples 126-128, preferred are the 3R,5R and 3R,5S isomers and the racemate of which each is a constituent, viz., the 3R,5R-3S,5S (threo) racemate and the 3R,5S-3S,5R (erythro) racemate, of which the latter is preferred. The preferred isomers of Examples 126-128 are the 3R,5R and 3R,5S isomers and the racemate of which is a constituent, viz., the 3R,5R-3S,5S (erythro) racemate and the 3R,5S-3S,5R (threo) racemate, of which the former is preferred. Each of the compounds of Tables I and III denoted by an E in the Isomer(s) column except Example 159 is the erythro racemate which may be resolved to obtain the 3R,5S and 3S,5R enantiomers by, for example, (i) lactonization, (ii) conversion to a mixture of two diastereoisomeric silyloxy compounds, (iii) chromatographic separation of the diastereoisomeric silyloxy compounds, (iv) cleavage of the silyl group and (v) hydrolysis of the obtained optically pure lactone, as set forth in more detail above, the 3R,5S isomer being preferred. The racemate of Example 159 may be resolved to obtain the 3R,5R and 3S,5S enantiomers, of which the former is preferred. Each of the compounds of Tables I and III denoted by a T in the Isomer(s) column is the threo racemate which may be resolved by, for example, the same procedure to obtain the 3R,5R and 3S,5S enantiomers, of which the former is preferred.

The small amount of impurity in examples such as Example 164 may be separated therefrom to obtain the pure erythro and threo racemates, if desired.

Each of the compounds of Tables II and IV denoted by cis in the Isomer(s) column is the cis racemate and each of the compounds of these tables denoted by trans in the Isomer(s) column is the trans racemate, cis and trans referring to the relative positions of the hydrogen atoms (or methyl group and hydrogen atom) in the 4- and 6-positions of the lactone ring. The cis racemates of Examples 88 and 137 may be resolved to obtain the 4R,6S and 4S,6R enantiomers and each of the other cis racemates of Table II and IV may be resolved to obtain the 4R,6R and 4S,6S enantiomers, of which the 4R,6S and 4R,6R enantiomers are preferred. The trans racemates of Examples 89 and 138 may be resolved to obtain the 4R,6R and 4S,6S enantiomers, and each of the other trans racemates of Tables II and IV may be resolved to obtain the 4R,6S and 4S,6R enantiomers, of which the 4R,6R and 4R,6S enantiomers are preferred. The cis and trans racemates may be resolved in Steps (ii)–(iv) of the procedure outlined in the second preceding paragraph.

The mixtures of Examples 85, 104, 121, 138A, 69 and 170 may be separated by conventional means to obtain the cis and trans racemates each of which may be resolved as set forth above. The mixture of Example 173 may be separated to obtain the two individual diastereoisomers.

Each of the compounds of Examples 2, 6, 8, 9, 14 and 14D and the examples of Tables I and III wherein $R_7$ is a cation may be converted into the corresponding free acid and into the corresponding compounds wherein $R_7$ is a different M by conventional means.

Each of the compounds of Examples 1–182 (including each of the possible optical isomers) may be administered to an animal, e.g., a larger primate, to inhibit cholesterol biosynthesis and thereby lower the blood cholesterol level for, for example, the treatment of atherosclerosis and hyperlipoproteinemia. The dosages are those set forth supra.

TABLE V

The following compounds of Formula XX may be obtained by the process set forth above.

| | R | $R_o$ | $R_2$ | $R_3$ | m.p. |
|---|---|---|---|---|---|
| Ex. Va | 3,4-di-$CH_3$—$C_6H_3$— | $CH_3$ | H | H | 97°–99° C. |
| Ex. Vb | 4-F—$C_6H_4$— | $C_6H_5CH_2CH_2$— | H | H | 86°–88° C. |
| Ex. Vc | 4-F—$C_6H_4$— | i-$C_3H_7$ | 5-cyclohexyl | H | 162°–167° C. |
| Ex. Vd | 2-$CH_3$—$C_6H_4$— | i-$C_3H_7$ | H | H | 190°–193° C. |
| Ex. Ve | 3,5-di-$CH_3$—$C_6H_3$— | $CH_3$ | H | H | 117°–118.5° C. |
| Ex. Vf | 4-F—$C_6H_4$— | $CH_3$ | 5-$OCH_3$ | H | 137°–138.5° C. |
| Ex. Vg | 4-F—$C_6H_4$— | $CH_3$ | 6-$OCH_2C_6H_5$ | H | 128.5°–131° C. |
| Ex. Vh | 4-F—$C_6H_4$— | $CH_3$ | 4-$OCH_2C_6H_5$ | H | 162.5°–164° C. |
| Ex. Vi | 4-F—$C_6H_4$— | $CH_3$ | 5-Cl | H | 169.5°–170.5° C. |
| Ex. Vj | $C_6H_5$— | $CH_3$ | H | H | 141.5°–142.5° C. |
| Ex. Vk | 4-F—$C_6H_4$— | $CH_3$ | 7-$OCH_2C_6H_5$ | H | 140°–141° C. |
| Ex. Vl | 4-F—$C_6H_4$— | $CH_3$ | 5-$OCH_2C_6H_5$ | H | 124.5°–125° C. |
| Ex. Vm | 3-$CF_3$—$C_6H_4$— | $CH_3$ | H | H | 124°–124.5° C |
| Ex. Vn | 4-F—$C_6H_4$— | $C_2H_5$ | H | H | 103°–105° C. |
| Ex. Vo | 4-F—$C_6H_4$— | i-$C_3H_7$ | 4-$CH_3$ | 6-$CH_3$ | 189°–190° C. |
| Ex. Vp | $C_6H_5$— | i-$C_3H_7$ | H | H | 111°–112° C. |
| Ex. Vq | 3,5-di-$CH_3$-4-F—$C_6H_2$— | i-$C_3H_7$ | H | H | 114.5°–115° C. |
| Ex. Vr | 4-F—$C_6H_4$— | i-$C_3H_7$ | 6-$OCH_2C_6H_5$ | H | 118.5°–120° C. |
| Ex. Vs | 4-F—$C_6H_4$— | i-$C_3H_7$ | 4-i-$C_3H_7$ | 6-i-$C_3H_7$ | 162°–163° C. |
| Ex. Vt | $CH_3$ | $C_6H_5$— | H | H | crude amorphous solid |

TABLE VI

The following compound of Formula XXIV may be obtained by the processes set forth above.

| | R | $R_o$ | $R_2$ | $R_3$ | $Y^\ominus$ | m.p. |
|---|---|---|---|---|---|---|
| Ex. VIa | 4-F—$C_6H_4$— | i-$C_3H_7$ | H | H | $Cl^\ominus$ | 236°–239° C. |

Throughout the examples, the term "reduced pressure" denotes aspirator pressure, and where no solvent is specified in connection with a solution, the solvent is water. All N.M.R. spectra were taken at ambient temperature on a 200 MHz. N.M.R. spectrometer (except where otherwise indicated) and all chemical shifts are given in p.p.m. ($\delta$) relative to tetramethylsilane. Where a single $\delta$ value is given for anything other than a sharp singlet, it is its center point. All solvent mixtures are by volume. Where the use of nitrogen is specified, usually dry nitrogen is utilized to maintain anhydrous conditions. The concentration (c) in the optical rotation data is given in grams/100 ml., and all optical rotations are uncorrected.

What is claimed is:

1. A compound of the formula

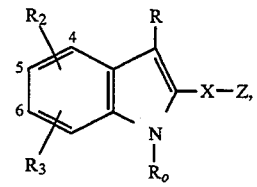

wherein one of R and $R_o$ is and the other is

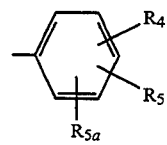

and the other is primary or secondary $C_{1-6}$alkyl not containing an asymmetric carbon atom, $C_{1-3}$cycloalkyl or phenyl-$(CH_2)_m$—, wherein $R_4$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy, $R_5$ is hydrogen, $C_{1-3}$alkyl, $C_{1-3}$alkoxy, trifluoromethyl, fluoro, chloro, phenoxy or benzyloxy, $R_{5a}$ is hydrogen, $C_{1-2}$alkyl, $C_{1-2}$alkoxy, fluoro, or chloro, and m is 1, 2 or 3, with the provisos that both $R_5$ and $R_{5a}$ must be hydrogen when $R_4$ is hydrogen, $R_{5a}$ must be hydrogen when $R_5$ is hydrogen, not more than one of $R_4$ and $R_5$ is trifluoromethyl, not more than one of $R_4$ and $R_5$ is phenoxy, and not more than one of $R_4$ and $R_5$ is benzyloxy, $R_2$ is hydrogen, $C_{1-3}$alkyl, n-butyl, i-butyl, t-butyl, $C_{3-6}$cycloalkyl, $C_{1-3}$alkoxy, n-butoxy, i-butoxy, trifluoromethyl, fluoro, chloro, phenoxy or benzyloxy, $R_3$ is hydrogen, $C_{1-3}$alkyl, $C_{1-3}$alkoxy, trifluoromethyl, fluoro, chloro, phenoxy or benzyloxy, with the provisos that $R_3$ must be hydrogen when $R_2$ is hydrogen, not more than one of $R_2$ and $R_3$ is trifluoromethyl, not more than one of $R_2$ and $R_3$ is phenoxy, and not more than one of $R_2$ and $R_3$ is benzyloxy, X is —$(CH_2)_n$— or —CH=CH—, wherein n is 0, 1, 2 or 3, and Z is

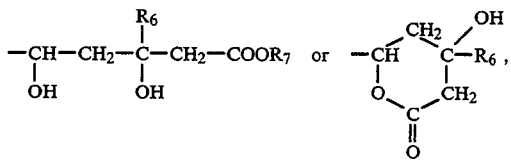

wherein $R_6$ is hydrogen or $C_{1-3}$alkyl, and $R_7$ is hydrogen, $C_{1-3}$alkyl, n-butyl, i-butyl, t-butyl, benzyl, or M, wherein M is a cation.

2. A compound according to claim 1 wherein M is a pharmaceutically acceptable cation.

3. A compound according to claim 2 having the formula

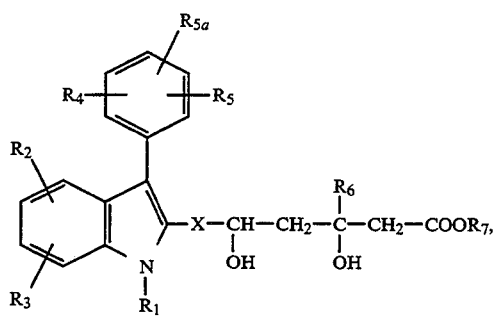

wherein $R_1$ is primary or secondary $C_{1-3}$alkyl not containing an asymmetric carbon atom, $C_{3-6}$cycloalkyl or phenyl-$(CH_2)_m$—, wherein m is 1, 2 or 3, $R_2$ is hydrogen, $C_{1-3}$alkyl, n-butyl, i-butyl, t-butyl, $C_{3-6}$cycloalkyl, $C_{1-3}$alkoxy, n-butoxy, i-butoxy, trifluoromethyl, fluoro, chloro, phenoxy or benzyloxy, $R_3$ is hydrogen, $C_{1-3}$alkyl, $C_{1-3}$alkoxy, trifluoromethyl, fluoro, chloro, phenoxy or benzyloxy, with the provisos that $R_3$ must be hydrogen when $R_2$ is hydrogen, not more than one of $R_2$ and $R_3$ is trifluoromethyl, not more than one of $R_2$ and $R_3$ is phenoxy, and not more than one of $R_2$ and $R_3$ is benzyloxy, $R_4$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy, $R_5$ is hydrogen, $C_{1-3}$alkyl, $C_{1-3}$alkoxy, trifluoromethyl, fluoro, chloro, phenoxy or benzyloxy, $R_{5a}$ is hydrogen, $C_{1-2}$alkyl, $C_{1-2}$alkoxy, fluoro or chloro, with the provisos that both $R_5$ and $R_{5a}$ must be hydrogen when $R_4$ is hydrogen, $R_{5a}$ must be hydrogen when $R_5$ is hydrogen, not more than one of $R_4$ and $R_5$ is trifluoromethyl, not more than one of $R_4$ and $R_5$ is phenoxy, and not more than one of $R_4$ and $R_5$ is benzyloxy, $R_6$ is hydrogen or $Cl_{1-3}$alkyl, $R_7$ is hydrogen, $C_{1-3}$alkyl, n-butyl, i-butyl, t-butyl, benzyl or M, wherein M is a pharmaceutically acceptable cation, and X is —$(CH_2)_n$— or —CH=CH—, wherein n is 0, 1, 2 or 3.

4. A compound according to claim 3 wherein $R_1$ is primary or secondary $C_{1-5}$alkyl not containing an asymmetric carbon atom, $R_2$ is hydrogen or $C_{1-3}$alkyl, $R_3$ is hydrogen or $Cl_{1-3}$alkyl, with the proviso that $R_3$ must be hydrogen when $R_2$ is hydrogen, $R_4$ is hydrogen, $C_{1-2}$alkyl, trifluoromethyl or fluoro, $R_5$ is hydrogen or methyl, $R_{5a}$ is hydrogen or methyl with the proviso that both $R_5$ and $R_{5a}$ must be hydrogen when $R_4$ is hydrogen and $R_5$ must be hydrogen when $R_5$ is hydrogen, $R_6$ is hydrogen or methyl, $R_7$ is hydrogen, $C_{1-2}$alkyl or M, wherein M is a pharmaceutically acceptable cation, and X is —$CH_2CH_2$— or —CH=CH—.

5. A compound according to claim 3 wherein $R_1$ is primary or secondary $C_{1-6}$alkyl not containing an asymmetric carbon atom, $R_2$ is hydrogen, $C_{1-3}$alkyl, $C_{1-3}$alkoxy, trifluoromethyl, fluoro, chloro, phenoxy or benzyloxy, $R_3$ is hydrogen, $C_{1-3}$alkyl, $C_{1-2}$alkoxy, fluoro or chloro, with the proviso that $R_3$ must be hydrogen when $R_2$ is hydrogen, $R_4$ is hydrogen, $C_{1-3}$alkyl, $C_{1-3}$alkoxy, trifluoromethyl, fluoro, chloro, phenoxy or benzyloxy, $R_5$ is hydrogen, $C_{1-2}$alkyl, $C_{1-2}$alkoxy, fluoro or chloro, $R_{5a}$ is hydrogen or methyl, with the provisos that both $R_5$ and $R_{5a}$ must be hydrogen when $R_4$ is hydrogen and $R_{5a}$ must be hydrogen when $R_5$ is hydrogen, $R_6$ is hydrogen or $C_{1-2}$alkyl, $R_7$ is hydrogen, $C_{1-3}$alkyl or M, wherein M is a pharmaceutically acceptable cation, and X is —$(CH_2)_m$— or

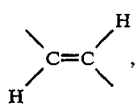

wherein m is 1, 2 or 3.

6. A compound according to claim 5 wherein

R₁ is C₁₋₃alkyl,

R₂ is hydrogen, C₁₋₃alkyl, methoxy, fluoro, chloro or 4-, 5- or 6-benzyloxy,

R₃ is hydrogen or C₁₋₃alkyl, with the proviso that R₃ must be hydrogen when R₂ is hydrogen, R₄ is hydrogen, methyl, methoxy, fluoro or chloro, R₅ is hydrogen, methyl, methoxy, fluoro or chloro, R₅ₐ is hydrogen or methyl, with the proviso that both R₅ and R₅ₐ must be hydrogen when R₄ is hydrogen and R₅ₐ must be hydrogen when R₅ is hydrogen, R₆ is hydrogen, R₇ is hydrogen, C₁₋₂alkyl or M, wherein M is a pharmaceutically acceptable cation, and X is —CH₂CH₂— or

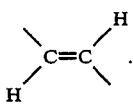

7. A compound according to claim 6 having the formula

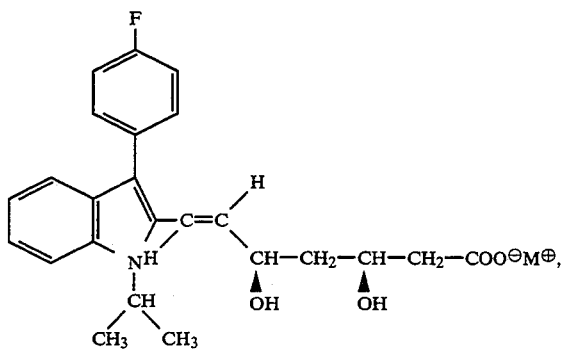

wherein M⊕ is a pharmaceutically acceptable cation.

8. A compound to claim 7 in racemic erythro form.

9. The compound according to claim 7 having the formula

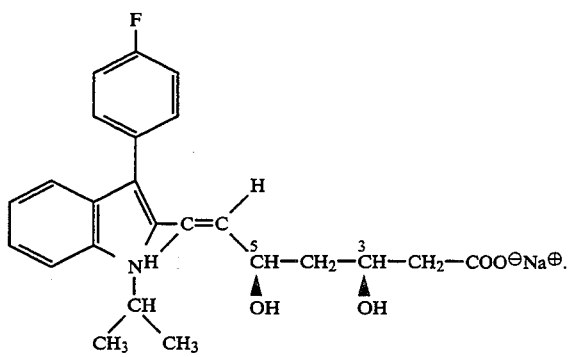

10. The compound according to claim 9 having the 3R,5S configuration.

11. The compound of the formula

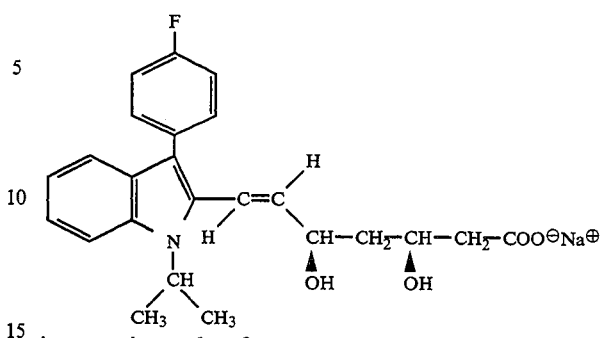

in racemic erythro form.

12. A compound according to claim 2 having the formula

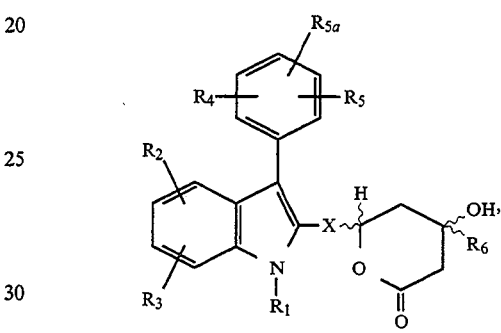

wherein

R₁ is primary or secondary C₁₋₆alkyl not containing an asymmetric carbon atom, C₃₋₆cycloalkyl or phenyl-(CH₂)ₘ—, wherein m is 1, 2 or 3, R₂ is hydrogen, C₁₋₃alkyl, n-butyl, i-butyl, t-butyl, C₃₋₆cycloalkyl, C₁₋₃alkoxy, n-butoxy, i-butoxy, trifluoromethyl, fluoro, chloro, phenoxy or benzyloxy, R₃ is hydrogen, C₁₋₃alkyl, C₁₋₃alkoxy, trifluoromethyl, fluoro, chloro, phenoxy or benzyloxy, with the provisos that R₃ must be hydrogen when R₂ is hydrogen, not more than one of R₂ and R₃ is trifluoromethyl, not more than one of R₂ and R₃ is phenoxy, and not more than one of R₂ and R₃ is benzyloxy, R₄ is hydrogen, C₁₋₃alkyl, n-butyl, i-butyl, t-butyl, C₁₋₃alkoxy, n-butoxy, i-butoxy, trifluoromethyl, fluoro, chloro, phenoxy or benzyloxy, R₅ is hydrogen, C₁₋₃alkyl, C₁₋₃alkoxy, trifluoromethyl, fluoro, chloro, phenoxy or benzyloxy, R₅ₐ is hydrogen, C₁₋₂alkyl, C₁₋₂alkoxy, fluoro or chloro, with the provisos that both R₅ and R₅ₐ must be hydrogen when R₄ is hydrogen, R₅ₐ must be hydrogen when R₅ is hydrogen, not more than one of R₄ and R₅ is trifluoromethyl, not more than one of R₄ and R₅ is phenoxy, and not more than one of R₄ and R₅ is benzyloxy, R₆ is hydrogen or C₁₋₃alkyl, and X is —(CH₂)ₙ— or —CH=CH—, wherein n is 0, 1, 2 or 3.

13. A compound according to claim 12 wherein

R₁ is primary or secondary C₁₋₆alkyl not containing an asymmetric carbon atom,

R₂ is hydrogen, C₁₋₃alkyl, C₁₋₃alkoxy, trifluoromethyl, fluoro, chloro, phenoxy or benzyloxy, $R_3$ is hydrogen, $C_{1-3}$alkyl, $C_{1-2}$alkoxy, fluoro or chloro, with the proviso that $R_3$ must be hydrogen when $R_2$ is hydrogen, $R_4$ is hydrogen, $C_{1-3}$alkyl, $C_{1-3}$alkoxy, trifluoromethyl, fluoro, chloro, phenoxy or benzyloxy, $R_5$ is hydrogen, $C_{1-2}$alkyl, $C_{1-2}$alkoxy, fluoro or chloro, $R_{5a}$ is hydrogen or methyl, with the provisos that both $R_5$ and $R_{5a}$ must be hydrogen when $R_4$ is hydrogen and $R_{5a}$ must be hydrogen when $R_5$ is hydrogen, $R_6$ is hydrogen or $C_{1-2}$alkyl, and X is

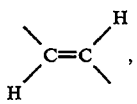

wherein m is 1, 2 or 3.

14. A compound according to claim 2 having the formula

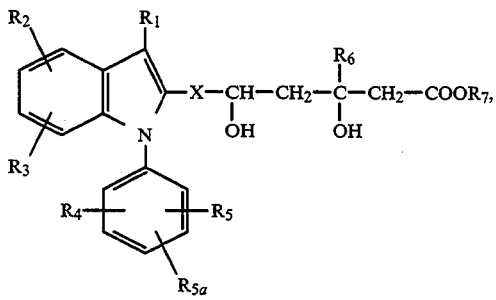

wherein $R_1$ is primary or secondary $C_{1-6}$alkyl not containing an asymmetric carbon atom, $C_{3-6}$cycloalkyl or phenyl-$(CH_2)_m$—, wherein m is 1, 2 or 3, $R_2$ is hydrogen, $C_{1-3}$alkyl, n-butyl, i-butyl, t-butyl, $C_{3-6}$cycloalkyl, $C_{1-3}$alkoxy, n-butoxy, i-butoxy, trifluoromethyl, fluoro, chloro, phenoxy or benzyloxy, $R_3$ is hydrogen, $C_{1-3}$alkyl, $C_{1-3}$alkoxy, trifluoromethyl, fluoro, chloro, phenoxy or benzyloxy, with the provisos that $R_3$ must be hydrogen when $R_2$ is hydrogen, not more than one of $R_2$ and $R_3$ is trifluoromethyl, not more than one of $R_2$ and $R_3$ is phenoxy, and not more than one of $R_2$ and $R_3$ is benzyloxy, $R_4$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy, $R_5$ is hydrogen, $C_{1-3}$alkyl, $C_{1-3}$alkoxy, trifluoromethyl, fluoro, chloro, phenoxy or benzyloxy, $R_{5a}$ is hydrogen, $C_{1-2}$alkyl, $C_{1-2}$alkoxy, fluoro or chloro, with the provisos that both $R_5$ and $R_{5a}$ must be hydrogen when $R_4$ is hydrogen, $R_{5a}$ must be hydrogen when $R_5$ is hydrogen, not more than one of $R_4$ and $R_5$ is trifluoromethyl, not more than one of $R_4$ and $R_5$ is phenoxy, and not more than one of $R_4$ and $R_5$ is benzyloxy, $R_6$ is hydrogen or $C_{1-3}$alkyl, $R_7$ is hydrogen, $C_{1-3}$alkyl, n-butyl, i-butyl, t-butyl, benzyl or M, wherein M is a pharmaceutically acceptable cation, and X is —$(CH_2)_n$— or —CH=CH—, wherein n is 0, 1, 2 or 3.

15. A compound according to claim 14 wherein $R_1$ is primary or secondary $C_{1-6}$alkyl not containing an asymmetric carbon atom, $R_2$ is hydrogen, $C_{1-3}$alkyl, $C_{1-3}$alkoxy, trifluoromethyl, fluoro, chloro, phenoxy or benzyloxy, $R_3$ is hydrogen, $C_{1-3}$alkyl, $C_{1-2}$alkoxy, fluoro or chloro, with the proviso that $R_3$ must be hydrogen when $R_2$ is hydrogen, $R_4$ is hydrogen, $C_{1-3}$alkyl, $C_{1-3}$alkoxy, trifluoromethyl, fluoro, chloro, phenoxy or benzyloxy, $R_5$ is hydrogen, $C_{1-2}$alkyl, $C_{1-2}$alkoxy, fluoro or chloro, $R_{5a}$ is hydrogen or methyl, with the provisos that both $R_5$ and $R_{5a}$ must be hydrogen when $R_4$ is hydrogen and $R_{5a}$ must be hydrogen when $R_5$ is hydrogen, $R_6$ is hydrogen or $C_{1-2}$alkyl, $R_7$ is hydrogen, $C_{1-3}$alkyl or M, wherein M is a pharmaceutically acceptable cation, and X is

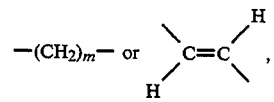

wherein m is 1, 2 or 3.

16. A compound according to claim 2 having the formula

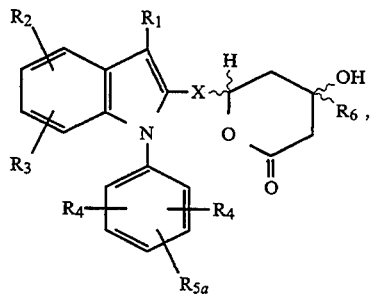

wherein $R_1$ is primary or secondary $C_{1-6}$alkyl not containing an asymmetric carbon atom, $C_{3-6}$cycloalkyl or phenyl-$(CH_2)_m$—, wherein m is 1, 2 or 3, $R_2$ is hydrogen, $C_{1-3}$alkyl, n-butyl, i-butyl, t-butyl, $C_{3-6}$cycloalkyl, $C_{1-3}$alkoxy, n-butoxy, i-butoxy, trifluoromethyl, fluoro, chloro, phenoxy or benzyloxy, $R_3$ is hydrogen, $C_{1-3}$alkyl $C_{1-3}$alkoxy, trifluoromethyl, fluoro, chloro, phenoxy or benzyloxy, with the provisos that $R_3$ must be hydrogen when $R_2$ is hydrogen, not more than one of $R_2$ and $R_3$ is trifluoromethyl, not more than one of $R_2$ and $R_3$ is phenoxy, and not more than one of $R_2$ and $R_3$ is benzyloxy, $R_4$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy, $R_5$ is hydrogen, $C_{1-3}$alkyl, $C_{1-3}$alkoxy, trifluoromethyl, fluoro, chloro, phenoxy or benzyloxy, $R_{5a}$ is hydrogen, $C_{1-2}$alkyl, $C_{1-2}$alkoxy, fluoro or chloro, with the provisos that both $R_5$ and $R_{5a}$ must be hydrogen when $R_4$ is hydrogen, $R_{5a}$ must be hydrogen when $R_5$ is hydrogen, not more than one of $R_4$ and $R_5$ is trifluoromethyl, not more than one of $R_4$ and $R_5$ is phenoxy, and not more than one of $R_4$ and $R_5$ is benzyloxy, $R_6$ is hydrogen or $C_{1-3}$ alkyl, and X is —$(CH_2)_n$— or —CH=CH—, wherein n is 0, 1, 2 or 3.

17. A compound according to claim 16 wherein $R_1$ is primary or secondary $C_{1-6}$alkyl not containing an asymmetric carbon atom, $R_2$ is hydrogen, $C_{1-3}$alkyl, $C_{1-3}$alkoxy, trifluoromethyl, fluoro, chloro, phenoxy or benzyloxy, $R_3$ is hydrogen, $C_{1-3}$alkyl, $C_{1-2}$alkoxy, fluoro or chloro, with the proviso that $R_3$ must be hydrogen when $R_2$ is hydrogen, $R_4$ is hydrogen, $C_{1-3}$alkyl, $C_{1-3}$alkoxy, trifluoromethyl, fluoro, chloro, phenoxy or benzyloxy, $R_5$ is hydrogen, $C_{1-2}$alkyl, $C_{1-2}$alkoxy, fluoro or chloro, $R_{5a}$ is hydrogen or methyl, with the provisos that both $R_5$ and $R_{5a}$ a must be hydrogen when $R_4$ is hydrogen and $R_{5a}$ must be hydrogen when $R_5$ is hydrogen, $R_6$ is hydrogen or $C_{1-2}$alkyl, and X is —$(CH_2)_m$— or $\overset{H}{\underset{H}{\diagdown}}C=C\overset{}{\underset{}{\diagup}}$ , wherein m is 1, 2 or 3.

18. A pharmaceutical composition comprising an effective amount of a compound according to claim 2 and a pharmaceutically acceptable carrier, said effective amount being an amount sufficient to inhibit cholesterol biosynthesis in a mammal.

19. A pharmaceutical composition according to claim 18 wherein the compound is a compound of the formula

[structure with 4-fluorophenyl-indole, C=C, CH(OH)—CH₂—CH(OH)—CH₂—COO⁻M⁺, N-CH(CH₃)₂]

wherein M⊕ is a pharmaceutically acceptable cation.

20. A pharmaceutical composition according to claim 19 wherein the compound is a compound of the formula

[structure with 4-fluorophenyl-indole, C=C, CH(OH)—CH₂—CH(OH)—CH₂—COO⁻M⁺, N-CH(CH₃)₂]

wherein M⊕ is a pharmaceutically acceptable cation, in racemic erythro form.

21. A pharmaceutical composition according to claim 20 wherein the compound is the compound of the formula

[structure with 4-fluorophenyl-indole, C=C, CH(OH)—CH₂—CH(OH)—CH₂—COO⁻Na⁺, N-CH(CH₃)₂]

in racemic erythro form.

22. A method of inhibiting cholesterol biosynthesis comprising administering to a mammal in need of such treatment an effective amount of a compound according to claim 2, said effective amount being an amount effective for inhibiting cholesterol biosynthesis.

23. A method of inhibiting cholesterol biosynthesis according to claim 22 wherein the compound is a compound of the formula

[structure with 4-fluorophenyl-indole, C=C, CH(OH)—CH₂—CH(OH)—CH₂—COO⁻M⁺, N-CH(CH₃)₂]

wherein M⊕ is a pharmaceutically acceptable cation.

24. A method of inhibiting cholesterol biosynthesis according to claim 23 wherein the compound is a compound of the formula

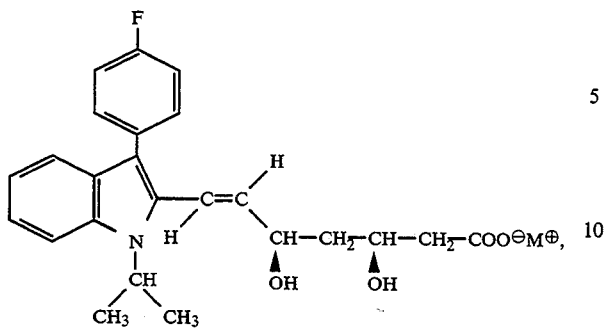

wherein M⊕ is a pharmaceutically acceptable cation, in racemic erythro form.

25. A method of inhibiting cholesterol biosynthesis according to claim 24 wherein the compound is the compound of the formula

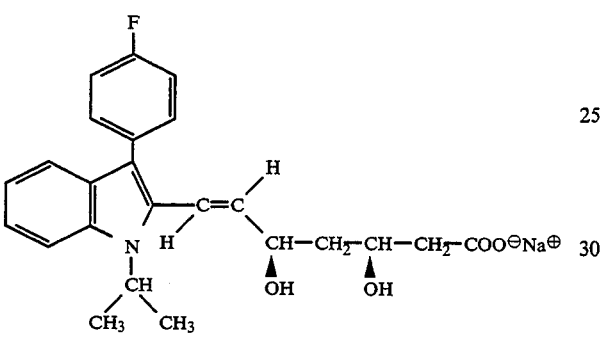

in racemic erythro form.

26. A method of treating atherosclerosis comprising administering to a mammal in need of such treatment an effective amount of a compound according to claim 2, said effective amount being an amount effective for the treatment of atherosclerosis.

27. A method of treating atherosclerosis according to claim 26 wherein the compound is a compound of the formula

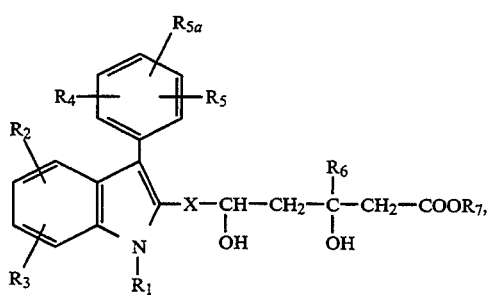

wherein
$R_1$ is primary or secondary $C_{1-6}$alkyl not containing an asymmetric carbon atom, $C_{3-6}$cycloalkyl or phenyl-$(CH_2)_m$—, wherein m is 1, 2 or 3,
$R_2$ is hydrogen, $C_{1-3}$alkyl, n-butyl, i-butyl, t-butyl, $C_{3-6}$cycloalkyl, $C_{1-3}$alkoxy, n-butoxy, i-butoxy, trifluoromethyl, fluoro, chloro, phenoxy or benzyloxy,
$R_3$ is hydrogen, $C_{1-3}$alkyl, $C_{1-3}$alkoxy, trifluoromethyl, fluoro, chloro, phenoxy or benzyloxy, with the provisos that $R_3$ must be hydrogen when $R_2$ is hydrogen, not more than one of $R_2$ and $R_3$ is trifluoromethyl, not more than one of $R_2$ and $R_3$ is phenoxy, and not more than one of $R_2$ and $R_3$ is benzyloxy,
$R_4$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy,
$R_5$ is hydrogen, $C_{1-3}$alkyl, $C_{1-3}$alkoxy, trifluoromethyl, fluoro, chloro, phenoxy or benzyloxy,
$R_{5a}$ is hydrogen, $C_{1-2}$alkyl, $C_{1-2}$alkoxy, fluoro or chloro, with the provisos that both $R_5$ and $R_{5a}$ must be hydrogen when $R_4$ is hydrogen, $R_{5a}$ must be hydrogen when $R_5$ is hydrogen, not more than one of $R_4$ and $R_5$ is trifluoromethyl, not more than one of $R_4$ and $R_5$ is phenoxy, and not more than one of $R_4$ and $R_5$ is benzyloxy,
$R_6$ is hydrogen or $C_{1-3}$alkyl,
$R_7$ is hydrogen, $C_{1-3}$alkyl, n-butyl, i-butyl, t-butyl, benzyl or M, wherein M is a pharmaceutically acceptable cation, and
X is —$(CH_2)_n$— or —CH=CH— wherein n is 0, 1, 2 or 3.

28. A method of treating atherosclerosis according to claim 27 wherein the compound is a compound of the formula

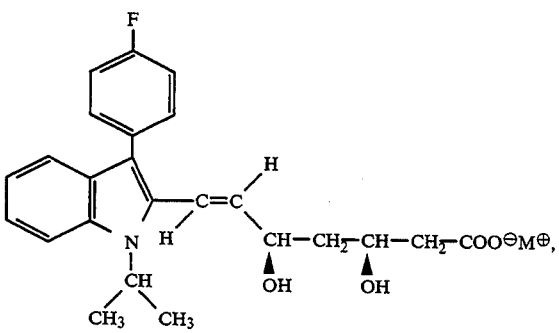

wherein M⊕ is a pharmaceutically acceptable cation.

29. A method of treating atherosclerosis according to claim 28 wherein the compound is a compound of the formula

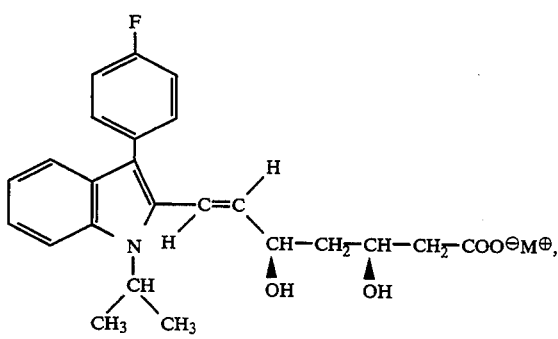

wherein M⊕ is a pharmaceutically acceptable cation, in racemic erythro form.

30. A method of treating atherosclerosis according to claim 29 wherein the compound is the compound of the formula

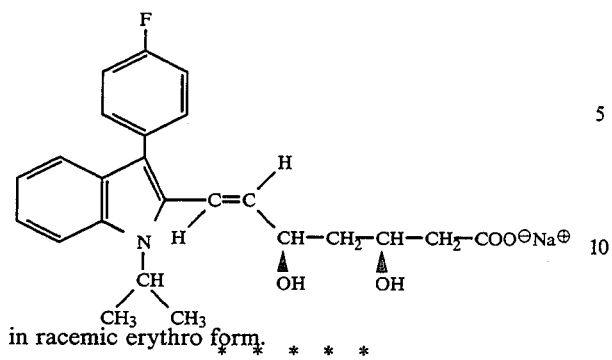
in racemic erythro form.
* * * * *